(12) United States Patent
Caplan et al.

(10) Patent No.: US 11,986,235 B2
(45) Date of Patent: May 21, 2024

(54) SYSTEMS, METHODS AND DEVICES FOR TREATMENT OF TARGET TISSUE

(71) Applicant: Fractyl Health, Inc., Lexington, MA (US)

(72) Inventors: Jay Caplan, Belmont, MA (US); Philip S. Levin, Storrs, CT (US); R. Maxwell Flaherty, Auburndale, FL (US); J. Christopher Flaherty, Auburndale, FL (US)

(73) Assignee: Fractyl Health, Inc., Lexington, MA (US)

( * ) Notice: Subject to any disclaimer, the term of this patent is extended or adjusted under 35 U.S.C. 154(b) by 0 days.

(21) Appl. No.: 14/917,243

(22) PCT Filed: Sep. 12, 2014

(86) PCT No.: PCT/US2014/055514
§ 371 (c)(1),
(2) Date: Jul. 12, 2016

(87) PCT Pub. No.: WO2015/038973
PCT Pub. Date: Mar. 19, 2015

(65) Prior Publication Data
US 2016/0354144 A1 Dec. 8, 2016

Related U.S. Application Data

(60) Provisional application No. 61/877,083, filed on Sep. 12, 2013.

(51) Int. Cl.
*A61B 18/14* (2006.01)
*A61B 8/12* (2006.01)
*A61B 18/00* (2006.01)

(52) U.S. Cl.
CPC ............ *A61B 18/1492* (2013.01); *A61B 8/12* (2013.01); *A61B 2018/00023* (2013.01);
(Continued)

(58) Field of Classification Search
CPC ...... A61B 18/1492; A61B 2018/00494; A61B 8/12; A61B 2018/00714;
(Continued)

(56) References Cited

U.S. PATENT DOCUMENTS 5,084,044 A * 1/1992 Quint ..................... A61B 18/00
606/191
5,190,540 A * 3/1993 Lee ......................... A61B 17/22
606/192
(Continued)

FOREIGN PATENT DOCUMENTS

| CA | 2666661 C | 1/2015 |
|---|---|---|
| CN | 1771888 A | 5/2006 |

(Continued)

OTHER PUBLICATIONS

Co-pending U.S. Appl. No. 15/683,713, filed Aug. 22, 2017.
(Continued)

*Primary Examiner* — Jaymi E Della
(74) *Attorney, Agent, or Firm* — WILSON SONSINI GOODRICH & ROSATI

(57) ABSTRACT

A system for treating a patient comprises an elongate shaft, an expandable reservoir and a fluid delivery assembly. The elongate shaft comprises a distal portion and is constructed and arranged to be introduced into a gastrointestinal lumen. The expandable reservoir is positioned on the elongate shaft distal portion and is constructed and arranged to receive a first fixed amount of ablative fluid and to deliver a first thermal dose of energy to a first portion of target tissue. The fluid delivery assembly is in fluid communication with the
(Continued)

expandable reservoir and is constructed and arranged to deliver the first fixed amount of ablative fluid to the expandable reservoir. Devices and methods for treating tissue of a patient are also provided.

23 Claims, 12 Drawing Sheets

(52) U.S. Cl.
CPC .............. *A61B 2018/00041* (2013.01); *A61B 2018/00166* (2013.01); *A61B 2018/0022* (2013.01); *A61B 2018/00482* (2013.01); *A61B 2018/00494* (2013.01); *A61B 2018/00577* (2013.01); *A61B 2018/00714* (2013.01)

(58) Field of Classification Search
CPC .. A61B 2018/00577; A61B 2018/0022; A61B 2018/00166; A61B 2018/00041; A61B 2018/00023; A61B 2018/00482; A61B 2018/00005; A61B 2018/00011; A61B 18/02; A61B 2018/0212; A61F 2007/0091; A61F 2007/0092; A61F 7/123
See application file for complete search history.

(56) References Cited

U.S. PATENT DOCUMENTS

| | | |
|---|---|---|
| 5,423,754 A | 6/1995 | Cornelius et al. |
| 5,471,982 A | 12/1995 | Edwards et al. |
| 5,496,311 A | 3/1996 | Abele et al. |
| 5,515,100 A | 5/1996 | Nogo |
| 5,542,928 A | 8/1996 | Evans et al. |
| 5,549,559 A | 8/1996 | Eshel |
| 5,575,772 A | 11/1996 | Lennox |
| 5,704,934 A | 1/1998 | Neuwirth et al. |
| 5,730,719 A | 3/1998 | Edwards |
| 5,800,484 A | 9/1998 | Gough et al. |
| 5,827,269 A | 10/1998 | Saadat |
| 5,859,037 A | 1/1999 | Whitcomb et al. |
| 5,869,037 A | 2/1999 | Crystal et al. |
| 5,871,525 A | 2/1999 | Edwards et al. |
| 5,879,347 A * | 3/1999 | Saadat ................. A61B 17/42 604/113 |
| 5,957,962 A | 9/1999 | Wallsten, I et al. |
| 5,964,753 A | 10/1999 | Edwards |
| 6,009,877 A | 1/2000 | Edwards |
| 6,053,937 A | 4/2000 | Edwards et al. |
| 6,056,744 A | 5/2000 | Edwards |
| 6,066,132 A | 5/2000 | Chen et al. |
| 6,077,257 A | 6/2000 | Edwards et al. |
| 6,112,123 A | 8/2000 | Kelleher et al. |
| 6,293,909 B1 | 9/2001 | Chu et al. |
| 6,325,777 B1 | 12/2001 | Zadno-Azizi et al. |
| 6,325,798 B1 | 12/2001 | Edwards et al. |
| 6,338,726 B1 | 1/2002 | Edwards et al. |
| 6,358,245 B1 | 3/2002 | Edwards et al. |
| 6,402,744 B2 | 6/2002 | Edwards et al. |
| 6,405,732 B1 | 6/2002 | Edwards et al. |
| 6,409,723 B1 | 6/2002 | Edwards |
| 6,425,887 B1 | 7/2002 | McGuckin et al. |
| 6,443,947 B1 | 9/2002 | Marko et al. |
| 6,544,226 B1 | 4/2003 | Gaiser et al. |
| 6,673,070 B2 | 1/2004 | Edwards et al. |
| 6,712,814 B2 | 3/2004 | Edwards et al. |
| 6,802,841 B2 | 10/2004 | Utley et al. |
| 6,905,496 B1 | 6/2005 | Ellman et al. |
| 6,962,587 B2 | 11/2005 | Johnson et al. |
| 6,974,456 B2 | 12/2005 | Edwards et al. |
| 7,077,841 B2 | 7/2006 | Gaiser et al. |
| 7,111,627 B2 | 9/2006 | Stack et al. |
| 7,122,031 B2 | 10/2006 | Edwards et al. |
| 7,125,407 B2 | 10/2006 | Edwards et al. |
| 7,156,860 B2 | 1/2007 | Wallsten |
| 7,165,551 B2 | 1/2007 | Edwards et al. |
| 7,241,295 B2 | 7/2007 | Maguire |
| 7,326,207 B2 | 2/2008 | Edwards |
| 7,371,215 B2 | 5/2008 | Colliou et al. |
| 7,387,626 B2 | 6/2008 | Edwards et al. |
| 7,422,587 B2 | 9/2008 | Bek et al. |
| 7,507,234 B2 | 3/2009 | Utley et al. |
| 7,507,238 B2 | 3/2009 | Utley et al. |
| 7,530,979 B2 | 5/2009 | Ganz et al. |
| 7,556,628 B2 | 7/2009 | Utley et al. |
| 7,585,296 B2 | 9/2009 | Edward et al. |
| 7,632,268 B2 | 12/2009 | Utley et al. |
| 7,632,291 B2 | 12/2009 | Stephens et al. |
| 7,648,500 B2 | 1/2010 | Edwards et al. |
| 7,758,623 B2 | 7/2010 | Dzeng et al. |
| 7,762,977 B2 | 7/2010 | Porter et al. |
| 7,947,038 B2 | 5/2011 | Edwards |
| 7,959,627 B2 | 6/2011 | Utley et al. |
| 7,993,336 B2 | 8/2011 | Jackson et al. |
| 7,997,278 B2 | 8/2011 | Utley et al. |
| 8,012,149 B2 | 9/2011 | Jackson et al. |
| 8,066,689 B2 | 11/2011 | Mitelberg et al. |
| 8,152,803 B2 | 4/2012 | Edwards et al. |
| 8,177,853 B2 | 5/2012 | Stack et al. |
| 8,192,426 B2 | 6/2012 | Stern et al. |
| 8,251,992 B2 | 8/2012 | Utley et al. |
| 8,273,012 B2 | 9/2012 | Wallace et al. |
| 8,323,229 B2 | 12/2012 | Shin et al. |
| 8,364,237 B2 | 1/2013 | Stone et al. |
| 8,377,055 B2 | 2/2013 | Jackson et al. |
| 8,641,711 B2 | 2/2014 | Kelly et al. |
| 8,740,894 B2 | 6/2014 | Edwards |
| 8,790,705 B2 | 7/2014 | Geigle et al. |
| 9,364,283 B2 | 6/2016 | Utley et al. |
| 9,555,020 B2 | 1/2017 | Pasricha et al. |
| 9,615,880 B2 | 4/2017 | Gittard et al. |
| 9,844,641 B2 | 12/2017 | Rajagopalan et al. |
| 10,610,663 B2 | 4/2020 | Rajagopalan et al. |
| 10,765,474 B2 | 9/2020 | Kadamus et al. |
| 10,864,352 B2 | 12/2020 | Rajagopalan et al. |
| 10,869,718 B2 | 12/2020 | Rajagopalan et al. |
| 2002/0013581 A1 | 1/2002 | Edwards et al. |
| 2002/0077594 A1 | 6/2002 | Chien et al. |
| 2002/0115992 A1 | 8/2002 | Utley et al. |
| 2002/0169473 A1* | 11/2002 | Sepetka ............ A61B 17/12022 606/200 |
| 2002/0192162 A1 | 12/2002 | Green |
| 2003/0040804 A1 | 2/2003 | Stack et al. |
| 2003/0093072 A1 | 5/2003 | Friedman |
| 2003/0153905 A1 | 8/2003 | Edwards et al. |
| 2003/0233065 A1 | 12/2003 | Steward et al. |
| 2004/0082859 A1 | 4/2004 | Schaer |
| 2004/0087936 A1 | 5/2004 | Stern et al. |
| 2004/0133256 A1* | 7/2004 | Callister ................. A61F 7/123 607/105 |
| 2004/0148034 A1 | 7/2004 | Kagan et al. |
| 2004/0204768 A1 | 10/2004 | Geitz |
| 2004/0215180 A1 | 10/2004 | Starkebaum et al. |
| 2004/0215296 A1 | 10/2004 | Ganz et al. |
| 2004/0220559 A1 | 11/2004 | Kramer et al. |
| 2005/0096638 A1 | 5/2005 | Starkebaum et al. |
| 2005/0154386 A1 | 7/2005 | West et al. |
| 2005/0165437 A1 | 7/2005 | Takimoto |
| 2005/0171524 A1 | 8/2005 | Stern et al. |
| 2005/0192652 A1 | 9/2005 | Cioanta et al. |
| 2005/0203489 A1 | 9/2005 | Saadat et al. |
| 2005/0222558 A1 | 10/2005 | Baxter et al. |
| 2005/0245943 A1* | 11/2005 | Zvuloni ................. F25B 9/02 606/121 |
| 2005/0251116 A1 | 11/2005 | Steinke et al. |
| 2005/0273090 A1 | 12/2005 | Nieman et al. |
| 2006/0070631 A1 | 4/2006 | Scopton et al. |
| 2006/0118127 A1 | 6/2006 | Chinn |
| 2006/0135963 A1 | 6/2006 | Kick et al. |
| 2006/0155261 A1 | 7/2006 | Bek et al. |
| 2006/0205992 A1 | 9/2006 | Lubock et al. |
| 2006/0247683 A1 | 11/2006 | Danek et al. |
| 2006/0259030 A1 | 11/2006 | Utley et al. |

(56) References Cited

U.S. PATENT DOCUMENTS

| | | |
|---|---|---|
| 2006/0293742 A1 | 12/2006 | Dann et al. |
| 2007/0016262 A1 | 1/2007 | Gross et al. |
| 2007/0032788 A1 | 2/2007 | Edwards et al. |
| 2007/0100355 A1 | 5/2007 | Bonde et al. |
| 2008/0045785 A1 | 2/2008 | Oyatsu |
| 2008/0107744 A1 | 5/2008 | Chu |
| 2008/0119788 A1 | 5/2008 | Winter |
| 2008/0125760 A1 | 5/2008 | Gilboa |
| 2008/0125803 A1 | 5/2008 | Sadamasa et al. |
| 2008/0147056 A1 | 6/2008 | Van et al. |
| 2008/0207994 A1 | 8/2008 | Gonon |
| 2008/0243112 A1 | 10/2008 | De Neve |
| 2008/0275445 A1 | 11/2008 | Kelly et al. |
| 2008/0319504 A1 | 12/2008 | Loushin et al. |
| 2009/0012469 A1 | 1/2009 | Nita |
| 2009/0012512 A1 | 1/2009 | Utley et al. |
| 2009/0012518 A1 | 1/2009 | Utley et al. |
| 2009/0018533 A1 | 1/2009 | Perkins et al. |
| 2009/0018604 A1 | 1/2009 | Mitelberg et al. |
| 2009/0048593 A1 | 2/2009 | Ganz et al. |
| 2009/0069805 A1 | 3/2009 | Fischer et al. |
| 2009/0270851 A1 | 10/2009 | Babkin et al. |
| 2010/0022891 A1 | 1/2010 | Zuluaga et al. |
| 2010/0030190 A1 | 2/2010 | Singh |
| 2010/0114087 A1 | 5/2010 | Edwards et al. |
| 2010/0114325 A1 | 5/2010 | Yang et al. |
| 2010/0168561 A1 | 7/2010 | Anderson |
| 2010/0168624 A1 | 7/2010 | Sliwa |
| 2010/0204673 A1 | 8/2010 | Miller |
| 2010/0204688 A1 | 8/2010 | Hoey et al. |
| 2010/0217151 A1 | 8/2010 | Gostout et al. |
| 2010/0234840 A1 | 9/2010 | Jackson et al. |
| 2010/0256775 A1 | 10/2010 | Belhe et al. |
| 2010/0260703 A1 | 10/2010 | Yankelson et al. |
| 2011/0046537 A1 | 2/2011 | Errico et al. |
| 2011/0091564 A1 | 4/2011 | Chu |
| 2011/0106273 A1 | 5/2011 | Belhe et al. |
| 2011/0160648 A1 | 6/2011 | Hoey |
| 2011/0172659 A1 | 7/2011 | Brannan |
| 2011/0184401 A1* | 7/2011 | Iwata .................. A61B 18/02 606/23 |
| 2011/0319809 A1 | 12/2011 | Smith |
| 2012/0004654 A1 | 1/2012 | Jackson et al. |
| 2012/0016364 A1 | 1/2012 | Mayse et al. |
| 2012/0059364 A1 | 3/2012 | Baust et al. |
| 2012/0197245 A1 | 8/2012 | Burnett et al. |
| 2012/0271277 A1 | 10/2012 | Fischell et al. |
| 2012/0271301 A1 | 10/2012 | Fischell et al. |
| 2012/0289952 A1 | 11/2012 | Utley et al. |
| 2013/0071466 A1 | 3/2013 | Chancellor et al. |
| 2013/0178910 A1 | 7/2013 | Azamian et al. |
| 2013/0345670 A1 | 12/2013 | Rajagopalan et al. |
| 2014/0031773 A1 | 1/2014 | Mikkaichi |
| 2014/0074077 A1 | 3/2014 | Lane |
| 2014/0088529 A1 | 3/2014 | Bengtson |
| 2014/0121646 A1 | 5/2014 | Lodin et al. |
| 2014/0135661 A1 | 5/2014 | Garrison et al. |
| 2014/0163664 A1 | 6/2014 | Goldsmith |
| 2014/0187619 A1 | 7/2014 | Pasricha et al. |
| 2014/0255458 A1 | 9/2014 | Li et al. |
| 2014/0324037 A1 | 10/2014 | Hoey et al. |
| 2014/0371736 A1* | 12/2014 | Levin .................. A61B 18/04 606/28 |
| 2015/0045825 A1* | 2/2015 | Caplan ................ A61M 29/00 606/191 |
| 2015/0141987 A1 | 5/2015 | Caplan et al. |
| 2015/0148738 A1 | 5/2015 | Caplan et al. |
| 2015/0359594 A1 | 12/2015 | Ben-Oren et al. |
| 2016/0008050 A1 | 1/2016 | Rajagopalan et al. |
| 2016/0081745 A1 | 3/2016 | Rajagopalan et al. |
| 2016/0256663 A1 | 9/2016 | Rajagopalan et al. |
| 2016/0310200 A1 | 10/2016 | Wang |
| 2017/0007310 A1 | 1/2017 | Rajagopalan et al. |
| 2017/0007324 A1 | 1/2017 | Kadamus et al. |
| 2017/0014596 A1 | 1/2017 | Rajagopalan et al. |
| 2017/0191035 A1 | 7/2017 | Sia et al. |

FOREIGN PATENT DOCUMENTS

| | | | |
|---|---|---|---|
| CN | 101212932 A | 7/2008 | |
| EP | 1698296 A1 | 9/2006 | |
| EP | 1886634 A1 | 2/2008 | |
| EP | 3071286 A1 | 9/2016 | |
| JP | 2002503512 A | 2/2002 | |
| JP | 2003520068 A | 7/2003 | |
| JP | 2004500184 A | 1/2004 | |
| JP | 2004180934 A | 7/2004 | |
| JP | 2006509536 A | 3/2006 | |
| JP | 2006136726 A | 6/2006 | |
| JP | 2007502690 A | 2/2007 | |
| JP | 2008515464 A | 5/2008 | |
| JP | 2010142661 A | 7/2010 | |
| JP | 2010533036 A | 10/2010 | |
| JP | 2011517599 A | 6/2011 | |
| JP | 2013543423 A | 12/2013 | |
| JP | 2014503256 A | 2/2014 | |
| KR | 20080013945 A | 2/2008 | |
| WO | WO-9418896 A1 | 9/1994 | |
| WO | WO-9912489 A2 | 3/1999 | |
| WO | WO-0207628 A2 | 1/2002 | |
| WO | WO-02058577 A1 | 8/2002 | |
| WO | WO-02096327 A2 | 12/2002 | |
| WO | WO-02102453 A2 | 12/2002 | |
| WO | WO-03033045 A2 | 4/2003 | |
| WO | WO-03092609 A2 | 11/2003 | |
| WO | WO-2004064600 A2 | 8/2004 | |
| WO | WO-2006020370 A2 | 2/2006 | |
| WO | WO-2007044244 A2 | 4/2007 | |
| WO | WO-2007067919 A2 | 6/2007 | |
| WO | WO-2008002654 A2 | 1/2008 | |
| WO | WO-2010042461 A1 | 4/2010 | |
| WO | WO-2010125570 A1 | 11/2010 | |
| WO | WO-2011060301 A1 | 5/2011 | |
| WO | WO-2012009486 A2 | 1/2012 | |
| WO | WO-2012099974 A2 | 7/2012 | |
| WO | WO2013/130655 * | 9/2013 | ............. A61B 18/04 |
| WO | WO-2013130655 A1 | 9/2013 | |
| WO | WO-2013134541 A2 | 9/2013 | |
| WO | WO-2013159066 A1 | 10/2013 | |
| WO | WO-2014022436 A1 | 2/2014 | |
| WO | WO-2014026055 A1 | 2/2014 | |
| WO | WO-2014055997 A1 | 4/2014 | |
| WO | WO-2014070136 A1 | 5/2014 | |
| WO | WO-2015038973 A1 | 3/2015 | |
| WO | WO-2015077571 A1 | 5/2015 | |
| WO | WO-2015148541 A1 | 10/2015 | |
| WO | WO-2016011269 A1 | 1/2016 | |
| WO | WO-2017004432 A1 | 1/2017 | |
| WO | WO-2018089773 | 5/2018 | |
| WO | WO-2018089773 A1 | 5/2018 | |
| WO | WO-2019018362 A1 | 1/2019 | |
| WO | WO-2019136240 A1 | 7/2019 | |

OTHER PUBLICATIONS

Co-pending U.S. Appl. No. 15/812,969, filed Nov. 14, 2017.
Co-pending U.S. Appl. No. 15/917,480, filed Mar. 8, 2018.
European Search Report and Search Opinion dated Aug. 7, 2017 for European Patent Application No. EP14864511.2.
European Search Report and Search Opinion dated Aug. 7, 2017 for European Patent Application No. EP15768945.6.
European search report with written opinion dated Feb. 1, 2018 for EP Application No. 15822378.
European search report with written opinion dated Dec. 2, 2016 for EP Application No. 14807116.
International search report with written opinion dated Jan. 9, 2018 for PCT/US2017/061074.
Notice of Allowance dated Sep. 14, 2017 for U.S. Appl. No. 15/274,809.
Office action dated Jan. 8, 2018 for U.S. Appl. No. 14/609,334.

(56) References Cited

OTHER PUBLICATIONS

Office action dated Mar. 19, 2018 for U.S. Appl. No. 14/470,503.
Office action dated Apr. 4, 2018 for U.S. Appl. No. 15/156,585.
Office action dated May 18, 2018 for U.S. Appl. No. 14/956,710.
Office Action dated Nov. 2, 2017 for U.S. Appl. No. 15/156,585.
Office action dated Nov. 16, 2017 for U.S. Appl. No. 14/609,332.
Office action dated Nov. 30, 2017 for U.S. Appl. No. 14/673,565.
Office action dated Dec. 18, 2017 for U.S. Appl. No. 14/515,324.
Office action dated Dec. 19, 2017 for U.S. Appl. No. 13/945,138.
Adams, et al. Theoretical design and evaluation of endoluminal ultrasound applicators for thermal therapy of pancreatic cancer under image guidance. AIP Conference Proceedings 1821, 110002 (2017); doi: http://dx.doi.org/10.1063/1.4977640.
Chathadi, et al. The role of endoscopy in ampullary and duodenal adenomas. Gastrointest Endosc. Nov. 2015;82(5):773-81. doi: 10.1016/j.gie.2015.06.027. Epub Aug. 7, 2015.
Cherrington, et al. Hydrothermal Duodenal Mucosal Resurfacing: Role in the Treatment of Metabolic Disease. Gastrointest Endosc Clin N Am. Apr. 2017;27(2):299-311. doi: 10.1016/j.giec.2016.12.002.
Co-pending U.S. Appl. No. 15/406,572, filed Jan. 13, 2017.
European search report and search opinion dated Mar. 8, 2016 for EP Application No. 13825257.2.
European search report and search opinion dated Mar. 17, 2016 for EP Application No. 13827149.9.
European search report and search opinion dated Aug. 4, 2015 for EP Application No. 13755156.0.
European search report and search opinion dated Nov. 25, 2015 for EP Application No. 13777572.2.
Galvao Neto, et al. Endoscopic Duodenal Mucosal Resurfacing Improves Glycemic and Hepatic Parameters in Patients With Type 2 Diabetes: Data From a First-in-Human Study. Gastroenterology. 829. Apr. 2016, vol. 150, Issue 4, Supplement 1, p. S174. 1 page. DOI: http://dx.doi.org/10.1016/S0016-5085(16)30672-2.
International search report and written opinion dated Feb. 20, 2015 for PCT Application No. US2014/711601.
International search report and written opinion dated Jun. 21, 2013 for PCT Application No. US2013/028082.
International search report and written opinion dated Jun. 26, 2015 for PCT Application No. US2015/022293.
International search report and written opinion dated Jul. 13, 2012 for PCT Application No. US2012/021739.
International search report and written opinion dated Aug. 8, 2013 for PCT Application No. US2013/037485.
International Search Report and Written Opinion dated Sep. 22, 2016 for International PCT Patent Application No. PCT/US2016/040512.
International search report and written opinion dated Oct. 23, 2015 for PCT/US2015/040775.
International search report and written opinion dated Nov. 8, 2013 for PCT Application No. US2013/052786.
International search report and written opinion dated Nov. 11, 2013 for PCT Application No. US2013/054219.
International search report and written opinion dated Dec. 24, 2014 for PCT Application No. US2014/055514.
International search report and written opinion dated Dec. 30, 2013 for PCT Application No. US2013/063753.
International search report dated Dec. 3, 2014 for PCT Application No. US2014/040957.
Miyawaki, et al. Inhibition of gastric inhibitory polypeptide signaling prevents obesity. Nat Med. Jul. 2002;8(7):738-42. Epub Jun. 17, 2002.
Notice of Allowance dated Jul. 7, 2017 for U.S. Appl. No. 15/274,764.
Office Action dated Jan. 13, 2017 for U.S. Appl. No. 14/609,332.
Office Action dated Feb. 29, 2016 for U.S. Appl. No. 14/609,334.
Office Action dated Mar. 7, 2017 for U.S. Appl. No. 15/274,764.
Office Action dated Mar. 7, 2017 for U.S. Appl. No. 15/274,809.
Office Action dated Mar. 12, 2015 for U.S. Appl. No. 13/945,138.
Office Action dated Mar. 23, 2017 for U.S. Appl. No. 13/945,138.
Office Action dated Mar. 28, 2016 for U.S. Appl. No. 14/673,565.

Office Action dated May 31, 2017 for U.S. Appl. No. 15/274,764.
Office Action dated Jun. 21, 2017 for U.S. Appl. No. 14/515,324.
Office Action dated Jun. 21, 2017 for U.S. Appl. No. 14/609,334.
Office Action dated Jun. 30, 2017 for U.S. Appl. No. 14/470,503.
Office Action dated Aug. 5, 2015 for U.S. Appl. No. 13/945,138.
Office Action dated Sep. 23, 2016 for U.S. Appl. No. 14/515,324.
Office Action dated Oct. 7, 2016 for U.S. Appl. No. 13/945,138.
Office Action dated Nov. 15, 2016 for U.S. Appl. No. 14/609,334.
Office Action dated Nov. 30, 2015 for U.S. Appl. No. 13/945,138.
Office Action dated Dec. 17, 2015 for U.S. Appl. No. 14/515,324.
Rajagopalan, et al. Endoscopic Duodenal Mucosal Resurfacing for the Treatment of Type 2 Diabetes: 6-Month Interim Analysis From the First-in-Human Proof-of-Concept Study. Diabetes Care Dec. 2016; 39(12): 2254-2261. https://doi.org/10.2337/dc16-0383.
Rubino, et al. Potential of surgery for curing type 2 diabetes mellitus. Ann Surg. Nov. 2002;236(5):554-9.
Sarriá, et al. Morphometric study of the layers of the canine small intestine at five sampling sites. Vet J. Jun. 2012;192(3):498-502. doi: 10.1016/j.tvjl.2011.06.041. Epub Nov. 3, 2011.
Tomizawa, et al. Clinical Outcome of Endoscopic Mucosal Resection (EMR) of Sporadic, Non-Ampullary Duodenal Adenoma (SNADA) : Predictor Analysis of Safety and Efficacy From a High Volume U.S. Tertiary Referral Center. Gastrointestinal Endoscopy. 377. May 2017, vol. 85, Issue 5, Supplement, p. AB72. DOI: http://dx.doi.org/10.1016/j.gie.2017.03.089.
Van Baar, et al. Single Catheter for Duodenal Mucosal Resurfacing Demonstrates Similar Safety Profile with Improved Procedure Time when Compared to Original Dual Catheter: Multicenter Study of Subjects with Type 2 Diabetes. Gastroenterology. Apr. 2017vol. 152, Issue 5, Supplement 1, p. S825. DOI: http://dx.doi.org/10.1016/S0016-5085(17)32851-2.
"Office action dated Dec. 18, 2018 for U.S. Appl. No. 14/470,503."
"Office Action dated Aug. 9, 2018 for U.S. Appl. No. 14/673,565."
"Office action dated Sep. 7, 2018 for U.S. Appl. No. 14/609,332."
"Office action dated Oct. 4, 2018 for U.S. Appl. No. 14/515,324."
"Office action dated Nov. 2, 2018 for U.S. Appl. No. 14/609,334".
Co-pending U.S. Appl. No. 16/379,554, filed Apr. 9, 2019.
Co-pending U.S. Appl. No. 16/400,491, filed May 1, 2019.
Co-pending U.S. Appl. No. 16/438,362, filed Jun. 11, 2019.
Co-pending U.S. Appl. No. 16/267,771, filed Feb. 5, 2019.
EP12736438.8 The Extended European Search Report dated Nov. 22, 2016.
EP14844285.8 The Extended European Search Report dated Apr. 25, 2017.
Final Office action dated Apr. 5, 2019 for U.S. Appl. No. 14/609,334.
Final Office action dated Jun. 17, 2019 for U.S. Appl. No. 14/609,332.
Final Office action dated Jul. 10, 2019 for U.S. Appl. No. 15/274,948.
Grikscheit, et al. Tissue-engineered small intestine improves recovery after massive small bowel resection. Ann Surg., 2004, 240:748-754.
Office action dated Mar. 7, 2019 for U.S. Appl. No. 13/945,138.
Office action dated Mar. 7, 2019 for U.S. Appl. No. 14/673,565.
Office action dated May 16, 2019 for U.S. Appl. No. 14/515,324.
Office action dated Jun. 6, 2019 for U.S. Appl. No. 15/683,713.
PCT/US14/66829 International Search Report dated Feb. 20, 2015.
PCT/US2019/012338 International Search Report dated Apr. 15, 2019.
Semkova, et al. Autologous transplantation of genetically modified iris pigment epithelial cells: A promising concept for the treatment of age-related macular degeneration and other disorders of the eye. Proc Natl Acad Sci U S A. Oct. 1, 2002; 99(20): 13090-13095.
Sen, et al. Autologous transplantation of endothelial progenitor cells genetically modified by adeno-associated viral vector delivering insulin-like growth factor-1 gene after myocardial infarction. Hum Gene Ther. Oct. 2010;21(10): 1327-34.
Tolman, et al. Spectrum of liver disease in type 2 diabetes and management of patients with diabetes and liver disease. Diabetes care 30.3 (2007): 734-743.
U.S. Appl. No. 15/274,948 Office Action dated Nov. 20, 2018.
U.S. Appl. No. 15/406,572 Office Action dated Feb. 7, 2019.
U.S. Appl. No. 15/683,713 Office Action dated Oct. 10, 2019.
U.S. Appl. No. 15/406,572 Office Action dated Nov. 15, 2019.

(56) References Cited

OTHER PUBLICATIONS

U.S. Appl. No. 15/683,713 Notice of Allowance dated Nov. 27, 2019.
U.S. Appl. No. 14/470,503 Notice of Allowance dated Feb. 27, 2019.
U.S. Appl. No. 14/956,710 Notice of Allowance dated Jan. 9, 2019.
Co-pending U.S. Appl. No. 16/711,236, filed Dec. 11, 2019.
Co-pending U.S. Appl. No. 16/742,645, filed Jan. 14, 2020.
U.S. Appl. No. 14/609,334 Office Action dated Jan. 8, 2020.
U.S. Appl. No. 15/917,480 Office Action dated Jan. 10, 2020.
Co-pending U.S. Appl. No. 16/798,117, filed Feb. 21, 2020.
U.S. Appl. No. 15/406,572 Office Action dated Apr. 14, 2020.
U.S. Appl. No. 14/515,324 Office Action dated Mar. 31, 2020.
U.S. Appl. No. 15/683,713 Notice of Allowance dated Mar. 10, 2020.
U.S. Appl. No. 13/945,138 Office Action dated Dec. 10, 2019.
U.S. Appl. No. 16/267,771 Office Action dated Feb. 6, 2020.
Co-pending U.S. Appl. No. 16/900,563, filed Jun. 12, 2020 by Kadamus; Christopher J. et al.
Co-pending U.S. Appl. No. 16/905,274, filed Jun. 18, 2020 by Rajagopalan; Harith et al.
Co-pending U.S. Appl. No. 17/021,798, filed Sep. 15, 2020 by Rajagopalan; Harith et al.
EP20150391.9 The Extended European Search Report dated Aug. 20, 2020.
PCT/US2018/042438 International Search Report dated Sep. 14, 2018.
U.S. Appl. No. 14/673,565 Office Action dated Jun. 12, 2020.
U.S. Appl. No. 15/274,948 Notice of Allowance dated May 14, 2020.
U.S. Appl. No. 16/267,771 Notice of Allowance dated Aug. 10, 2020.
EP20159816.6 The Extended European Search Report dated Aug. 17, 2020.
Co-pending U.S. Appl. No. 17/095,108, inventors Rajagopalan; Harith et al., filed Nov. 11, 2020.
Co-pending U.S. Appl. No. 17/096,855, inventors Rajagopalan; Harith et al., filed Nov. 12, 2020.
Co-pending U.S. Appl. No. 17/110,720, inventors J.; Kadamus Christopher J. et al., filed Dec. 3, 2020.
U.S. Appl. No. 13/945,138 Notice of Allowance dated Dec. 22, 2020.
U.S. Appl. No. 14/515,324 Office Action dated Dec. 4, 2020.
U.S. Appl. No. 14/609,334 Notice of Allowance dated Dec. 10, 2020.
U.S. Appl. No. 14/609,334 Office Action dated Oct. 29, 2020.
U.S. Appl. No. 15/406,572 Notice of Allowance dated Oct. 28, 2020.
U.S. Appl. No. 15/917,480 Notice of Allowance dated Dec. 17, 2020.
U.S. Appl. No. 15/917,480 Office Action dated Nov. 20, 2020.
U.S. Appl. No. 16/711,236 Office Action dated Dec. 10, 2020.
U.S. Appl. No. 16/900,563 Notice of Allowance dated Dec. 17, 2020.
U.S. Appl. No. 16/900,563 Office Action dated Nov. 9, 2020.
U.S. Appl. No. 14/673,565 Office Action dated Dec. 24, 2020.

* cited by examiner

SYSTEMS, METHODS AND DEVICES FOR TREATMENT OF TARGET TISSUE

CROSS-REFERENCE TO RELATED APPLICATIONS

This application is a national stage under 371 filing of International Patent Application No. PCT/US2014/055514, filed Sep. 12, 2014, which claims priority to U.S. Provisional Application No. 61/877,083, filed Sep. 12, 2013, the entire contents of which are incorporated herein by reference.

This application is related to: U.S. patent application Ser. No. 13/945,138, entitled "Devices and Methods for the Treatment of Tissue", filed Jul. 18, 2013; International Patent Application Serial Number PCT/US2013/28082, entitled "Heat Ablation Systems, Devices and Methods for the Treatment of Tissue", filed Feb. 27, 2013; International PCT Application Serial Number PCT/US2013/37485, entitled "Tissue Expansion Devices, Systems and Methods", filed Apr. 19, 2013; International Patent Application Serial Number PCT/US2013/063753, entitled "Methods, Systems and Devices for Performing Multiple Treatments on a Patient", filed Oct. 7, 2013; and International Patent Application Serial Number PCT/US2014/040957, entitled "Methods, Systems and Devices for Reducing the Luminal Surface Area of the Gastrointestinal Tract", filed Jun. 4, 2014; the contents of which are each incorporated herein by reference in its entirety.

TECHNICAL FIELD

The embodiments disclosed herein relate generally to systems, devices and methods for treating tissue, particularly gastrointestinal tissue.

BACKGROUND OF THE INVENTION

A number of systemic diseases are currently treated with medicines that provide amelioration of symptoms or complications of the illnesses but which do not specifically target the pathologic basis of disease. These illnesses are characterized as "chronic diseases" for no reason other than the fact that, for the majority of patients, the diseases are chronically managed rather than acutely treated.

The reasons that chronic diseases are not treated definitively differ based on the specific diseases in question. In some cases, the diseases are not understood well enough as of yet for definitive therapies to have been developed to solve them. In other cases, the definitive therapy, if it does exist, is too unattractive (e.g. high morbidity or mortality, high risk of complications, inaccessible) for the majority of patients to achieve therapeutic relief. In either case, chronic management of the illness burdens the patient with the need for ongoing medical attention and burdens the healthcare provider and system to continue to deliver episodic (and expensive) care of chronic diseases and their complications.

Diabetes is a metabolic disease in which a person develops high blood sugar because the person's body does not produce enough insulin or the cells of the body are incapable of effectively responding to the produced insulin. Primarily, diabetes is of two types: Type 1 and Type 2. Type 1 diabetes results from the body's autoimmune destruction of pancreatic beta cells and, consequently, the body's failure to produce enough insulin. Type 2 diabetes is a complex metabolic derangement related to obesity that causes hyperglycemia through insulin resistance (in which the body's cells fail to properly utilize the produced insulin) and eventually inadequate insulin production to meet the body's needs.

Currently, there are several procedures aimed at treating diabetes based on the above concept. The procedures require major surgery, removal of portions of the gastrointestinal (GI) tract, and/or long-term implants. As with any major surgery, gastric bypass surgery carries a risk of complications.

Devices have been developed to delivery energy to the body. For example, cardiac ablation devices have been designed to delivery ablative energy to coronary tissue. Additionally, urethral resection devices have been designed to burn or cut away portions of a prostate. Each of these technologies has been modified and adapted toward effective usage in the particular portion of the body to be treated as well as the particular disease to be treated.

New inventions that can harness novel physiologic understanding of diseases and deliver therapies that are therapeutically beneficial, accessible to patients, and reduce healthcare costs are needed. Specifically, there is a need to provide a therapeutic treatment of patient diseases and disorders such as diabetes, with a procedure in the GI tract that is simple, and minimally invasive, and has other advantages for patients.

SUMMARY OF THE INVENTION

In one aspect of the present inventive concepts, provided is a system for treating a patient comprising an elongate shaft, an expandable reservoir and a fluid delivery assembly. The elongate shaft comprises a distal portion, and the elongate shaft is constructed and arranged to be introduced into a gastrointestinal lumen. The expandable reservoir is positioned on the elongate shaft distal portion, and the expandable reservoir is constructed and arranged to receive a first fixed amount of ablative fluid and to deliver a first thermal dose of energy to a first portion of target tissue. The fluid delivery assembly is in fluid communication with the expandable reservoir, and the fluid delivery assembly is constructed and arranged to deliver the first fixed amount of ablative fluid to the expandable reservoir.

In some embodiments, the first thermal dose comprises heat energy delivered to the first portion of target tissue from the first fixed amount of ablative fluid. Alternatively or additionally, the first thermal dose can comprise heat energy removed from the first portion of target tissue by the first fixed amount of ablative fluid.

In some embodiments, the first fixed amount of ablative fluid comprises a fixed volume of fluid. The fixed volume of fluid can comprise a volume between approximately 10 ml and 100 ml. The fixed volume of fluid can comprise a volume less than 50 ml.

In some embodiments, the first fixed amount of ablative fluid comprises a fixed mass of fluid. The fixed mass of fluid can comprise a mass between approximately 10 g and 100 g. The fixed mass of fluid can comprise a mass less than or equal to 50 g.

In some embodiments, the first fixed amount of ablative fluid comprises fluid delivered to the expandable reservoir at a temperature above 37° C., such as fluid delivered at a temperature above 80° C., above 85° C., or above 90° C.

In some embodiments, the first fixed amount of ablative fluid comprises a fluid selected from the group consisting of: water; saline; glycerin; oil; dye such as methylene blue or indigo carmine; and combinations thereof.

In some embodiments, the system is constructed and arranged to deliver the first thermal dose while maintaining the expandable reservoir at a pressure below 4.0 psi. The system can be constructed and arranged to deliver the first thermal dose while maintaining the expandable reservoir at a pressure below 3.2 psi, such as at a pressure below 2.4 psi, below 1.6 psi or below 1.0 psi. In these embodiments, the system can be further constructed and arranged to deliver the first thermal dose while maintaining the expandable reservoir at a pressure of at least 0.2 psi, such as at a pressure of at least 0.3 psi, 0.35 psi, 0.6 psi or 0.7 psi, such as to maintain the expandable reservoir in sufficient contact with tissue during delivery of the first thermal dose of energy.

In some embodiments, the system can be constructed and arranged to deliver the first thermal dose while maintaining the expandable reservoir at a pressure of at least 0.2 psi, such as at a pressure of at least 0.3 psi, 0.35 psi, 0.6 psi or 0.7 psi, such as to maintain the expandable reservoir in sufficient contact with tissue during delivery of the first thermal dose of energy.

In some embodiments, the system is constructed and arranged to maintain the expandable reservoir in contact with the target tissue for a minimum time period while the first fixed amount of ablative fluid is maintained within the expandable reservoir. The minimum time period can comprise a time period of at least 0.5 seconds, such as a time period of at least 1 second or at least 3 seconds.

In some embodiments, the system is constructed and arranged to maintain the expandable reservoir in contact with the target tissue for less than a maximum time period while the first fixed amount of ablative fluid is maintained within the expandable reservoir. The minimum time period can comprise a time period of at least 0.5 seconds, or at least 1 second, or at least 3 seconds.

In some embodiments, the system is constructed and arranged to maintain the expandable reservoir in contact with the target tissue for less than a maximum time period while the first fixed amount of ablative fluid is maintained within the expandable reservoir. The maximum time period can comprise a time period less than or equal to 10 seconds, or less than or equal to 6 seconds.

In some embodiments, the system is constructed and arranged to stop the delivery of energy at least one of to or from the expandable reservoir. The system can be constructed and arranged to radially contract the expandable reservoir to stop energy delivery. The system can be constructed and arranged to remove fluid from the expandable reservoir to stop energy delivery. The system can be constructed and arranged to deliver a neutralizing fluid into the expandable reservoir to reduce the effects of the first thermal dose. The system can be constructed and arranged to remove a majority of the first fixed amount of ablative fluid prior to delivering the neutralizing fluid into the expandable reservoir. The system can be constructed and arranged to remove the majority of the first fixed amount of ablative fluid in less than or equal to 5 seconds. The system can be constructed and arranged to deliver the neutralizing fluid into the expandable reservoir in less than or equal to 5 seconds. The neutralizing fluid can comprise a cooling fluid constructed and arranged to stop a heat ablation of the target tissue. Alternatively or additionally, the neutralizing fluid can comprise a warming fluid constructed and arranged to stop a cryogenic ablation of the target tissue.

In some embodiments, the system is constructed and arranged to treat the first portion of target tissue in a time period less than or equal to 90 seconds, such as in a time period less than or equal to 60 seconds or in a time period between 20 seconds and 60 seconds. The time period can comprise a time period in which a single thermal dose is delivered or multiple thermal doses are delivered.

In some embodiments, the expandable reservoir is further constructed and arranged to receive a second fixed amount of ablative fluid and to deliver a second thermal dose of energy to a second portion of target tissue. The first portion of target tissue can comprise a first tissue segment and the second portion of target tissue can comprise the first tissue segment. The first portion of target tissue can comprise a second tissue segment wherein the second portion of target tissue does not include the second tissue segment. The first thermal dose can comprise a delivery time period of less than 30 seconds and the second thermal dose can comprise a delivery time period of less than 30 seconds. The first thermal dose can comprise a delivery time period of less than 20 seconds and the second thermal dose can comprise a delivery time period of less than 20 seconds. The system can be constructed and arranged to deliver the second thermal dose to a second portion of target tissue comprising different tissue than the first target tissue portion.

In some embodiments, the system is constructed and arranged to deliver multiple thermal doses of energy to the first portion of target tissue, wherein the multiple thermal doses of energy comprises the first thermal dose of energy and at least a second thermal dose of energy. The system can be constructed and arranged to deliver the multiple thermal doses within a pre-determined time period. The system can be constructed and arranged to deliver a neutralizing fluid to the expandable reservoir between the two thermal dose deliveries. The pre-determined time period can comprise a time period less than or equal to 20 seconds, such as a time period less than or equal to 10 seconds or less than or equal to 6 seconds. The multiple doses can comprise at least three thermal doses of energy. The at least three thermal doses of energy can be delivered by at least three fixed amounts of ablative fluid. The at least three thermal doses of energy can comprise similar or dissimilar doses of energy.

In some embodiments, the system is constructed and arranged to deliver at least a second thermal dose of energy to target tissue and a third dose of energy to target tissue. The first, second and third thermal doses of energy can each comprise delivery time periods less than 45 seconds, such as time periods less than 30 seconds.

In some embodiments, the system is constructed and arranged to fill the expandable reservoir with the first fixed amount of ablative fluid in less than or equal to 5 seconds, such as a fluid filling of the expandable reservoir that occurs in less than or equal to 2 seconds, 1 second or 0.5 seconds.

In some embodiments, the system is constructed and arranged to remove a majority of the first fixed amount of ablative fluid from the expandable reservoir in less than or equal to 5 seconds, such as a removal of the majority of fluids from the expandable reservoir that occurs in less than or equal to 2 seconds, 1 second or 0.5 seconds.

In some embodiments, the system is constructed and arranged to deliver a cooling fluid to cool tissue after the first thermal dose of energy is delivered. The cooling fluid can be delivered to the expandable reservoir. The cooling fluid can comprise a fixed amount of cooling fluid. The cooling fluid can comprise a fluid at a temperature less than 37° C., such as a fluid at a temperature less than 7° C., less than 4° C. or less than 0° C. The system can be constructed and arranged to deliver a second thermal dose after the delivery of the cooling fluid.

In some embodiments, the system is constructed and arranged to deliver a warming fluid to warm tissue after the first thermal dose of energy is delivered. The warming fluid can be delivered to the expandable reservoir. The warming fluid can comprise a fixed volume of warming fluid. The warming fluid can comprise a fluid at a temperature greater than 37° C., such as fluid at a temperature greater than 41° C., or 45° C. The system can be constructed and arranged to deliver a second thermal dose after the delivery of the warming fluid.

In some embodiments, the elongate shaft comprises a length of at least 100 cm, such as a shaft with a length of approximately 135 cm. In some embodiments, the elongate shaft comprises a maximum diameter less than or equal to 13 mm, or less than or equal to 6 mm, or 3 mm. In some embodiments, the elongate shaft is constructed and arranged to pass through a working channel of an endoscope. In some embodiments, the elongate shaft is constructed and arranged to be advanced through a body lumen over a guidewire. The elongate shaft can comprise a distal portion with a sidecar constructed and arranged to slidingly receive the guidewire. In some embodiments, the elongate shaft comprises a braided shaft. In some embodiments, the elongate shaft comprises a multiple layer shaft. In some embodiments, the elongate shaft comprises a steerable shaft.

In some embodiments, the elongate shaft comprises an insulating element. The insulating element can comprise a lumen filled with circulating fluid constructed and arranged to tend the elongate shaft toward body temperature. The circulating fluid can comprise a fluid selected from the group consisting of: a liquid; a gas; and combinations thereof. The circulating fluid can comprise a cooling fluid and/or a warming fluid.

In some embodiments, the system further comprises a fluid delivery passage in fluid communication with the fluid delivery assembly and the expandable reservoir. The system can be constructed and arranged to remove fluids from the expandable reservoir through the fluid delivery passage. The removed fluids can comprise a removed gas and/or a removed liquid. The fluid delivery passage can comprise a lumen of the elongate shaft. The fluid delivery passage can be constructed and arranged to be radially compacted. The system can be constructed and arranged to radially compact the passage by applying a negative pressure within the passage. The passage can be constructed and arranged to transition from a compacted state to an expanded state when the pressure within the passage exceeds a threshold pressure. The system can be constructed and arranged to radially compact the passage by applying a force at one or more locations positioned outside the passage. The elongate shaft comprises a single fluid delivery passage. The fluid delivery passage can be constructed and arranged to deliver fluid to the expandable reservoir and extract fluid from the expandable reservoir. The fluid delivery passage can comprise a diameter of approximately 0.10", such as a diameter of approximately 0.10" when the fluid delivery passage is in a radially expanded (e.g. non-compacted) state. The fluid delivery passage diameter can comprise a diameter of approximately 0.10" when in a radially expanded state. The fluid delivery passage can comprise a diameter of at least 0.050", such as a diameter of at least 0.075" or at least 0.100". The elongate shaft can further comprise an insulator surrounding at least a portion of the fluid delivery passage. The elongate shaft can further comprise a coil surrounding at least a portion of the fluid delivery passage. The coil can be constructed and arranged to be radially compacted. The coil can comprise a distal portion and a proximal portion, and the distal portion can be constructed and arranged to compress at a lower force than the proximal portion. The elongate shaft can comprise a first elongate shaft, and the system can further comprise a second elongate shaft surrounding at least a portion of the first elongate shaft. The second elongate shaft can comprise an outer surface, and the fluid delivery passage can comprise a first fluid delivery passage, and the system can further comprise a second fluid delivery passage positioned between the first shaft and the second shaft outer surface. The second fluid delivery passage can comprise a sealed end positioned proximate the expandable reservoir. The system can be constructed and arranged to deliver fluid into the second fluid delivery passage to radially compact the first elongate shaft and/or first fluid delivery passage. The second fluid delivery passage can be constructed and arranged to modify the temperature of at least a portion of the first elongate shaft and/or the first fluid delivery passage. The second fluid delivery passage can be constructed and arranged to receive a fluid to thermally prime the first elongate shaft and/or the first fluid delivery passage. The second fluid delivery passage can be constructed and arranged to receive a thermally insulating fluid. The first elongate shaft can be constructed and arranged to be translatable within the second elongate shaft. The first elongate shaft can comprise a compliant tube and/or a non-compliant tube. The first elongate shaft can comprise a material selected from the group consisting of: polyether block amide (PEBAX); nylon; polyethylene terephthalate (PET); silicone; and combinations thereof. The fluid delivery passage can comprise a valve. The valve can be constructed and arranged to prevent fluid from entering the expandable reservoir when fluid in the passage is below a first threshold pressure. The valve can be constructed and arranged to allow fluid to enter the expandable reservoir when the fluid is above a second threshold pressure. The valve can comprise a duck-bill valve. The system can further comprise an advanceable control rod and the valve can be constructed and arranged to be opened by the translatable control rod. The system can further comprise an advanceable control rod and the valve can be constructed and arranged to be closed by the translatable control rod. The system can further comprise an insulator surrounding at least a portion of the fluid delivery tube. The insulator can comprise a second tube. The insulator can comprise fluid.

In some embodiments, the expandable reservoir comprises a balloon. The balloon can comprise a compliant balloon, a non-compliant balloon or a balloon with both compliant and non-compliant portions.

In some embodiments, the expandable reservoir comprises a wall thickness of less than or equal to 0.002", such as a wall thickness less than or equal to 0.001".

In some embodiments, the expandable reservoir comprises a material selected from the group consisting of: polyether block amide (PEBAX); nylon; polyethylene terephthalate (PET); silicone; latex; and combinations thereof.

In some embodiments, the expandable reservoir comprises an expanded volume between 10 ml and 50 ml.

In some embodiments, the expandable reservoir comprises an expanded diameter of at least 17 mm, such as an expanded diameter of at least 17 mm, at least 20 mm at least 22 mm or at least 25 mm.

In some embodiments, the expandable reservoir comprises a cylindrical portion with a relatively uniform diameter. The cylindrical portion can comprise a length of at least 10 mm, such as a length of at least 20 mm or at least 25 mm. Alternatively or additionally, the cylindrical portion can comprise a length of less than or equal to 60 mm, such as a length of less than or equal to 45 mm or less than or equal to 30 mm. The expandable reservoir can further comprise a first end portion and a second end portion, and the first and second end portions can comprise tapered profiles.

In some embodiments, the expandable reservoir comprises a first expandable reservoir and the system further comprises at least a second expandable reservoir. The elongate shaft can comprise a first elongate shaft, and the system can comprise a second elongate shaft with a distal portion, and the second expandable reservoir can be positioned on the second elongate shaft distal portion. The first expandable reservoir can comprise a first expanded diameter and the second expandable reservoir can comprise a second expanded diameter different than the first expanded diameter. The first expandable reservoir can comprise a first length and the second expandable reservoir can comprise a second length different than the first length.

In some embodiments, the fluid delivery assembly is constructed and arranged to provide the first fixed amount of ablative fluid at a pre-determined starting temperature. The fluid delivery assembly can comprise a user interface constructed and arranged to allow an operator to adjust the pre-determined starting temperature. The pre-determined temperature can comprise a temperature of at least 80° C., such as a temperature of at least 85° C., or at least 90° C. Alternatively or additionally, the pre-determined temperature can comprise a temperature less than 105° C. such as a temperature less than 101° C. The pre-determined temperature can comprise a temperature less than 0° C.

In some embodiments, the fluid delivery assembly is constructed and arranged to provide fluid to the expandable reservoir at a flow rate of at least 2000 ml/min, such as fluid provided at a flow rate of at least 2500 ml/min.

In some embodiments, the fluid delivery assembly is further constructed and arranged to deliver a thermal priming fluid to at least one of the elongate shaft or the expandable reservoir. The first fixed amount of ablative fluid can comprise a first temperature, and the thermal priming fluid delivered can comprise a second temperature similar or dissimilar to the first temperature.

In some embodiments, the system further comprises a second fluid delivery assembly. The second fluid delivery assembly can be constructed and arranged to deliver a thermal priming fluid. Alternatively or additionally, the second fluid delivery assembly can be constructed and arranged to deliver a neutralizing fluid.

In some embodiments, the system further comprises a fluid evacuation assembly constructed and arranged to remove fluid from at least one of the elongate shaft or the expandable reservoir. The fluid delivery assembly can comprise the fluid evacuation assembly. The fluid evacuation assembly can be constructed and arranged to provide approximately 1 atmosphere of pressure differential between the fluid extraction assembly and the expandable reservoir. The fluid extraction assembly can be constructed and arranged to extract fluid at a flow rate of at least 750 ml/min, such as at a flow rate of at least 1000 ml/min.

In some embodiments, the system further comprises at least one temperature sensor. The at least one temperature sensor can comprise a sensor selected from the group consisting of: thermocouple; thermistor; resistance temperature detector; and combinations thereof. The expandable reservoir can comprise a wall with an inner surface and an outer surface, and the at least one temperature sensor can be positioned at a location selected from the group consisting of: inner surface of the expandable reservoir; outer surface of the expandable reservoir; within the wall of the expandable reservoir; and combinations thereof.

In some embodiments, the system further comprises a heating element. The heating element can be positioned proximate at least one of the elongate shaft or the expandable reservoir. The heating element can be positioned proximate the expandable reservoir. The heating element can comprise an element selected from the group consisting of: linear heating element; coiled heating element; and combinations thereof. The heating element can be constructed and arranged to produce heat when exposed to electromagnetic energy. The electromagnetic energy can comprise energy selected from the group consisting of: microwave energy; laser energy such as 2 micron CW laser energy; and combinations thereof. The heating element can comprise at least one ultrasonic receiver element constructed and arranged to produce heat when exposed to ultrasonic waves. The heating element can be positioned in the expandable reservoir and can be constructed and arranged to absorb sound energy to heat fluid in the expandable reservoir.

In some embodiments, the system further comprises a fluid mixing element constructed and arranged to mix fluid in the expandable reservoir. The fluid mixing element is constructed and arranged to cause the fluid in the expandable reservoir to tend to a similar temperature. The fluid mixing element can comprise an element selected from the group consisting of: propeller; blade; stirring rod; rotary stirring rod; cable attached to expandable reservoir to cause mixing; and combinations of these. The fluid mixing element can be positioned in the expandable reservoir. The fluid mixing element can comprise a rod with a distal end and an agitating element on the distal end. The agitating element can be constructed and arranged to be advanced in the expandable reservoir and rotated. The fluid mixing element can be positioned proximal to the elongate shaft. The fluid mixing element can be constructed and arranged to provide fluid pulsing to agitate fluid in the expandable reservoir. The fluid mixing element can comprise an ultrasonic receiver in the expandable reservoir, and an ultrasound generator proximal to the expandable reservoir.

In some embodiments, the system further comprises a luminal sizing assembly constructed and arranged to obtain luminal geometry information. The expandable reservoir can comprise the luminal sizing assembly.

According to another aspect of the present inventive concepts, a method for treating a patient comprises delivering a first fixed amount of ablative fluid to an expandable reservoir; and maintaining the expandable reservoir in contact with a first portion of target tissue and delivering a thermal dose to the first portion of target tissue.

In some embodiments, the first fixed amount of ablative fluid is provided by a system as described hereabove.

In some embodiments, the method further comprises delivering a second fixed amount of ablative fluid to the expandable reservoir; and maintaining the expandable reservoir in contact with a second portion of target tissue and delivering a thermal dose to the second portion of target tissue. The second portion of target tissue can comprise tissue not included in the first portion of target tissue. The method can further comprise delivering a third fixed amount of ablative fluid to the expandable reservoir; and maintaining the expandable reservoir in contact with a third portion of target tissue and delivering a thermal dose to the third portion of target tissue. The third portion of target tissue can comprise tissue not included in the first portion of target tissue, and the third portion of target tissue can comprise tissue not included in the second portion of target tissue.

In some embodiments, the expandable reservoir is maintained in contact with target tissue for a minimum time period.

In some embodiments, the expandable reservoir is maintained in contact with target tissue for a target time period. The expandable reservoir can be radially compacted after the target time period has been reached. The target time period can comprise a time period between approximately 0.5 seconds and 120 seconds.

In some embodiments, the method further comprises performing a sizing procedure of the target tissue. The method can further comprise selecting an expandable reservoir size based on the sizing procedure.

In some embodiments, the method can further comprise performing a thermal priming procedure. The thermal priming procedure can be performed with fluid at a temperature similar and/or dissimilar to the fluid of the first fixed amount of ablative fluid.

In some embodiments, the method further comprises performing a tissue expansion procedure proximate the first portion of target tissue. The tissue expansion procedure can be constructed and arranged to expand submucosal tissue. The tissue expansion procedure can be performed with a device constructed and arranged to deliver a pre-determined volume of fluid of at least 1 ml, or at least 5 ml. The tissue expansion procedure can comprise injecting fluid at three locations along a circumference of tissue. The tissue expansion procedure can comprise injecting fluid at a first circumferential site and a second circumferential site approximately 1 cm from the first circumferential site, or between 0.5 cm and 5.0 cm. The tissue expansion procedure can comprise injecting fluid at a first circumferential site and a second circumferential site, and the second circumferential site can be between 0.5 cm and 5.0 cm from the first circumferential site, such as between 1 cm and 3 cm from the first circumferential site, or between 1 cm and 2 cm from the first circumferential site. The tissue expansion procedure can comprise performing multiple injections that are at least one of axially or radially spaced apart. The multiple injections can be performed in tubular tissue, and the injections can be spaced at a distance based on luminal diameter of the tubular tissue. The tissue expansion procedure can comprise applying negative pressure to tissue proximate the injection site. The tissue expansion procedure can comprise injecting material selected from the group consisting of: water; saline; gel; and combinations thereof. The injected material can comprise a protein hydrogel.

In some embodiments, the method further comprises controlling at least one system parameter. The controlled system parameter can comprise a parameter selected from the group consisting of: a priming procedure parameter such as priming temperature or priming duration; a target tissue treatment parameter such as target tissue temperature or target tissue treatment duration; a fluid flow rate such as treatment fluid flow rate; a pressure parameter such as a treatment element pressure maintained during treatment of target tissue; a treatment element diameter such as a treatment element diameter maintained during treatment of target tissue; and combinations thereof.

In some embodiments, the method further comprises at least one of selecting or controlling the expandable reservoir size. The method can further comprise at least one of selecting or controlling the expandable reservoir diameter.

In some embodiments, the method further comprises advancing the expandable reservoir over a guidewire.

BRIEF DESCRIPTION OF THE DRAWINGS

The foregoing and other objects, features and advantages of embodiments of the present inventive concepts will be apparent from the more particular description of preferred embodiments, as illustrated in the accompanying drawings in which like reference characters refer to the same or like elements. The drawings are not necessarily to scale, emphasis instead being placed upon illustrating the principles of the preferred embodiments.

DETAILED DESCRIPTION OF THE INVENTION

Figure 1:
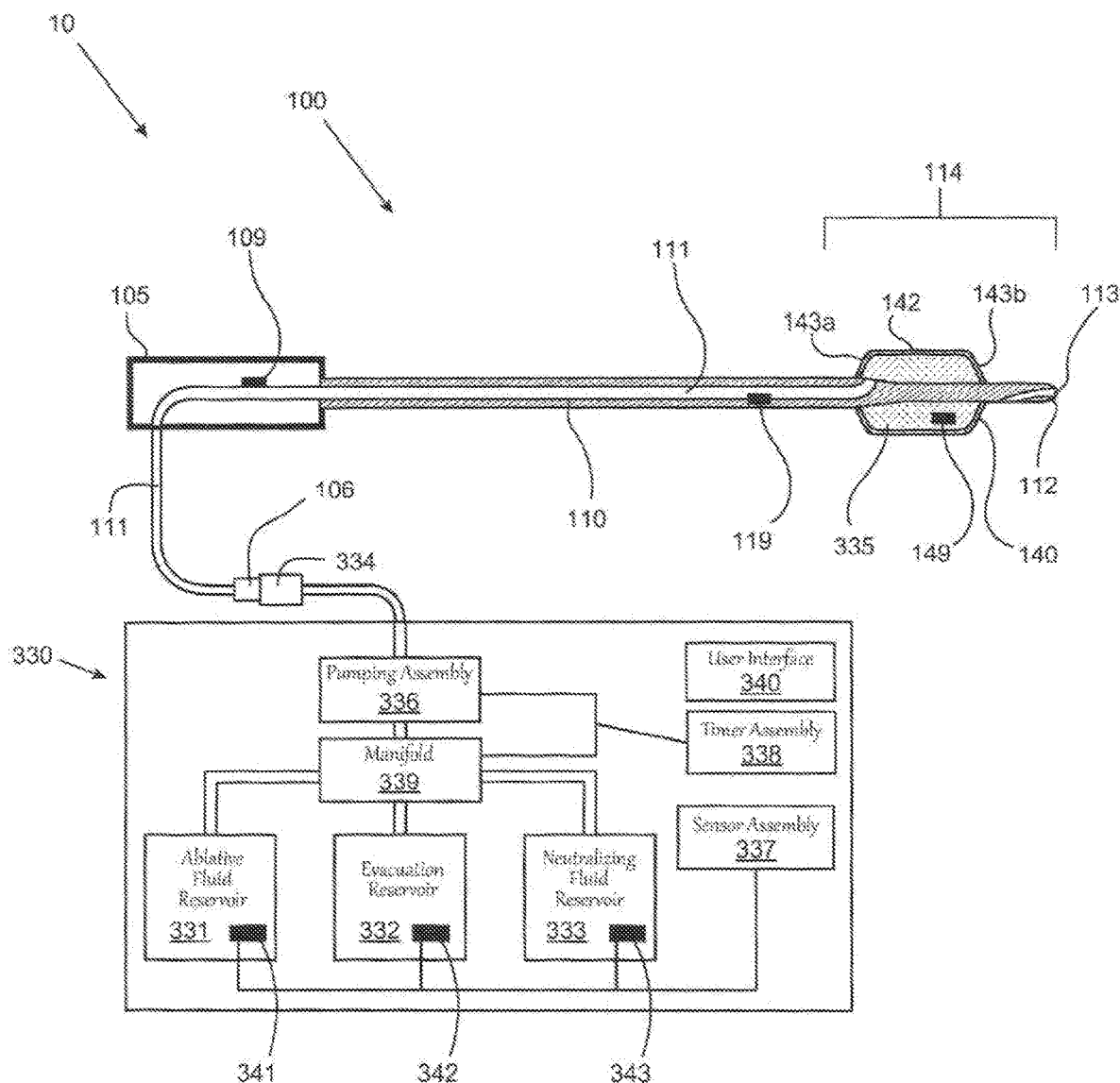
FIG. 1 is a schematic view of a tissue treatment system, consistent with the present inventive concepts.

The terminology used herein is for the purpose of describing particular embodiments and is not intended to be limiting of the inventive concepts. Furthermore, embodiments of the present inventive concepts may include several novel features, no single one of which is solely responsible for its desirable attributes or which is essential to practicing an inventive concept described herein. As used herein, the singular forms "a," "an" and "the" are intended to include the plural forms as well, unless the context clearly indicates otherwise.

It will be further understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be understood that, although the terms first, second, third etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on", "attached", "connected" or "coupled" to another element, it can be directly on or above, or connected or coupled to, the other element or intervening elements can be present. In contrast, when an element is referred to as being "directly on", "directly attached", "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

Spatially relative terms, such as "beneath," "below," "lower," "above," "upper" and the like may be used to describe an element and/or feature's relationship to another element(s) and/or feature(s) as, for example, illustrated in the figures. It will be understood that the spatially relative terms are intended to encompass different orientations of the device in use and/or operation in addition to the orientation depicted in the figures. For example, if the device in a figure is turned over, elements described as "below" and/or "beneath" other elements or features would then be oriented "above" the other elements or features. The device can be otherwise oriented (e.g., rotated 90 degrees or at other orientations) and the spatially relative descriptors used herein interpreted accordingly.

The term "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination. For example, it will be appreciated that all features set out in any of the claims (whether independent or dependent) can be combined in any given way.

As described herein, room pressure shall mean pressure of the environment surrounding the systems and devices of the present inventive concepts. Positive pressure includes pressure above room pressure or a pressure that is greater than another pressure, such as a positive differential pressure across a fluid pathway component such as a valve. Negative pressure includes pressure below room pressure or a pressure that is less than another pressure, such as a negative differential pressure across a fluid component pathway such as a valve. Negative pressure can include a vacuum but does not imply a pressure below a vacuum. As used herein, the term "vacuum" can be used to refer to a full or partial vacuum, or any negative pressure as described hereabove.

As used herein, the term "ablative fluid" refers to one or more fluids whose thermal properties (at sufficiently high or low temperatures) cause tissue necrosis or another desired tissue modification. Alternatively or additionally, "ablative fluid" refers to one or more fluids whose chemical properties (at room temperature, body temperature or otherwise) cause tissue necrosis or another desired tissue treatment.

It is an object of the present inventive concepts to provide systems, methods and devices for safely and effectively treating a volume of tissue (the "target tissue"), such as to treat a patient disease or disorder. Target tissue can comprise one or more target tissue segments or other target tissue portions. The target tissue can comprise one or more layers of a portion of tubular or non-tubular tissue, such as tissue of an organ or tissue of the gastrointestinal (GI) tract of a patient. The systems and devices of the present inventive concepts include one or more treatment devices configured to treat the target tissue, such as one or more devices including one or more treatment assemblies and/or treatment elements. The treatment assemblies and/or treatment elements can be configured to deliver energy to tissue, such as to cause a reduction in the surface area of tissue (e.g. the luminal surface area of tubular tissue) at or proximate to the tissue where the energy was delivered. The luminal or other tissue surface area reduction can occur acutely and/or it can take place over time such as days, weeks or months. The tissue surface area reduction can correspond to a reduction in mucosal surface area available to function in an absorptive and/or a secretory capacity. The tissue surface area reduction can provide a therapeutic benefit to the patient, such as to treat one or more disease or disorder of the patient, as described in detail herebelow.

Each treatment assembly can comprise at least one tissue treatment element such as a balloon or other expandable reservoir configured to receive ablative fluid. In some embodiments, the treatment element can further comprise one or more electrodes configured to deliver RF energy, one or more light delivery elements configured to deliver laser or other light energy, and/or one or more fluid delivery elements configured to deliver an ablative fluid directly to tissue. Numerous forms of treatment assemblies and/or treatment elements can be included. In some embodiments, the treatment assemblies and/or the one or more treatment elements contained therein are configured as described in: applicant's co-pending U.S. patent application Ser. No. 13/945,138, entitled "Devices and Methods for the Treatment of Tissue", filed Jul. 18, 2013; applicant's co-pending International PCT Application Serial Number PCT/US2013/28082, entitled "Heat Ablation Systems, Devices and Methods for the Treatment of Tissue", filed Feb. 27, 2013; applicant's co-pending International PCT Application Serial Number PCT/US2013/052786, entitled "Electrical Energy Ablation Systems, Devices and Methods for the Treatment of Tissue", filed Jul. 30, 2013; applicant's co-pending International PCT Application Serial Number PCT/US2013/54219, entitled "Ablation Systems, Devices and Methods for the Treatment of Tissue", filed Aug. 8, 2013; the contents of each of which is incorporated herein by reference in its entirety.

The treatment assemblies and treatment elements of the present inventive concepts can deliver energy to a particular area of tissue, the "energy delivery zone". During a single energy delivery, a treatment element can be constructed and arranged to deliver energy to a relatively continuous surface of tissue. In these continuous-surface energy delivery embodiments, the energy delivery zone comprises the continuous surface of tissue. Alternatively, a treatment element can be constructed and arranged to deliver energy to multiple discrete portions of tissue surface, with one or more tissue portions in-between that do not receive energy from the treatment element. In these segmented-surface energy delivery embodiments, the energy delivery zone is defined by a periphery of the multiple tissue surface area portions receiving energy, similar to a "convex hull" or "convex envelope" used in mathematics to define an area including a number of discrete locations that define a periphery. An energy delivery zone can comprise one or more energy delivery zones.

For example, in embodiments where the treatment element is a balloon filled with hot fluid (e.g. at a sufficiently high temperature to cause tissue necrosis), the energy delivery zone comprises all tissue surfaces contacted by the balloon that directly receive thermal energy from the balloon. In embodiments, where the treatment element is a balloon filled with cold fluid (e.g. at a sufficiently low temperature to cause tissue necrosis), the energy delivery zone comprises all tissue surfaces contacted by the balloon that have heat extracted from them by the cold fluid. In embodiments where the treatment element is an array of electrodes configured to deliver RF energy, the energy delivery zone comprises an area defined by the electrodes on the periphery of the array (e.g. a convex hull as described above). In embodiments where the treatment element comprises one or more fluid delivery elements delivering ablative fluid directly to tissue (e.g. an ablative fluid whose chemical nature modifies tissue, at body temperature or otherwise), the energy delivery zone comprises a surface defined by the periphery of tissue locations receiving the ablative fluid. In embodiments where the treatment element comprises one or more light delivery elements such as those that deliver laser energy to tissue, the energy delivery zone comprises a surface area defined by the periphery of tissue locations receiving the light energy. In embodiments in which the treatment element comprises a mechanical cutter, the energy delivery zone can comprise a surface defined by all tissue dissected or otherwise cut during a single cutting step of the mechanical cutter.

An energy delivery zone can comprise a cumulative set of energy delivery zones that receive energy simultaneously or sequentially, by one or more tissue treatment elements, such as those described immediately hereabove. An energy delivery zone can comprise a first energy delivery zone defined when a treatment element treats target tissue in a first energy delivery, plus a second energy delivery zone defined when the treatment element treats target tissue in a second energy delivery, and so on. In these embodiments, the treatment element can be translated or otherwise repositioned between energy deliveries, and each energy delivery zone associated with the position of the treatment element during the delivery of energy. Multiple energy delivery zones can receive energy in a single procedure, such as within a period of less than twenty-four hours. An energy delivery zone can comprise a similar cumulative set of multiple energy delivery zones delivered by two or more treatment elements.

In some embodiments, two or more clinical procedures are performed in which one or more volumes of target tissue are treated in each clinical procedure, such as is described in applicant's co-pending International Patent Application Serial Number PCT/US2013/063753, entitled "Methods, Systems and Devices for Performing Multiple Treatments on a Patient", filed Oct. 7, 2013. For example, a second clinical procedure can be performed at least twenty-four hours after the first clinical procedure, such as a second clinical procedure performed within 6 months of a first clinical procedure or a clinical procedure performed after at least 6 months from the first clinical procedure. The first and second clinical procedures can be performed using similar or dissimilar methods, and they can be performed using similar or dissimilar devices (e.g. performed with similar or dissimilar treatment elements). The first and second clinical procedures can treat similar or dissimilar volumes of target tissue (e.g. similar or dissimilar amounts of tissue treated and/or locations of tissue treated), and they can deliver energy to similar or dissimilar sets of multiple energy delivery zones. In some embodiments, the first and second clinical procedures can include treating and/or delivering energy to contiguous and/or overlapping regions of the GI tract either in the circumferential and/or axial dimensions. In other embodiments, the first and second clinical procedures can include the treatment of disparate regions of the GI tract (such as disparate regions of the duodenum, jejunum, ileum, and/or stomach). The first and second clinical procedures can be performed using similar or dissimilar treatment devices. The first and second clinical procedures can comprise similar or dissimilar deliveries of energy to treat the target tissue. The first and second clinical procedures can be performed at similar or dissimilar temperatures. The second clinical procedure can be performed based on diagnostic results collected after the first clinical procedure has been performed. In some embodiments, a similar or dissimilar third clinical procedure is performed.

Each treatment assembly and/or treatment element of the present inventive concepts can be configured to treat target tissue in one or more locations of the patient, such as one or more contiguous or discontiguous tissue locations treated in one or more discrete steps. The target tissue comprises a three dimensional volume of tissue, and can include a first portion, a treatment portion, whose treatment has a therapeutic benefit to a patient; as well as a second portion, a "safety-margin" portion, whose treatment has minimal or no adverse effects to the patient. "Non-target tissue" can be identified (e.g. prior to and/or during the medical procedure), wherein the non-target tissue comprises tissue whose treatment by the treatment assembly and/or treatment element should be reduced or avoided such as to reduce or prevent an undesired effect (e.g. an undesired clinical effect).

The target tissue treatment can cause one or more modifications of the target tissue such as a modification selected from the group consisting of: modification of cellular function; modification of one or more secretions of the target tissue; modification of one or more absorptions of the target tissue; cell death; apoptosis; instant cell death; cell necrosis; denaturing of cells; removal of cells; and combinations of these. In some embodiments, the target tissue treatment is configured to create scar tissue. Target tissue can be selected such that after treatment the treated target tissue and/or the tissue that replaces the target tissue functions differently than the pre-treated target tissue, such as to have a therapeutic benefit. The modified and/or replacement tissue can have different secretions and/or quantities of secretions than the pre-treated target tissue, such as to treat diabetes and/or obesity. The modified and/or replacement tissue can have different absorptive properties than the target tissue, such as to treat diabetes, obesity and/or hypercholesterolemia. The modified and/or replacement tissue can have a different surface topography than the target tissue, such as a modification of the topography of the inner wall of the GI tract that includes a smoothing or flattening of its inner surface, such as a modification in which the luminal surface area of one or more segments of the GI tract is reduced after treatment. The effect of the treatment can occur acutely, such as within twenty-four hours, or after longer periods of time such as greater than twenty-four hours or greater than one week.

Target tissue to be treated can comprise two or more discrete tissue segments, such as two or more axial segments of the GI tract. Each target tissue segment can comprise a full or partial circumferential segment of an axial segment of tissue. Multiple target tissue segments can be treated with the same or different treatment elements, and they can be treated simultaneously or in sequential steps (e.g. sequential energy delivery steps that deliver energy to multiple energy delivery zones). Multiple target tissue segments can be treated in the same or different clinical procedures (e.g. procedures performed on different days). In some embodiments, a series of target tissue segments comprising a series of axial segments of the GI tract are treated in a single clinical procedure. First and second target tissue segments can be directly adjacent and they can contain overlapping portions of tissue. Dissimilarities in treatment elements used to treat one or more target tissue segments can include type and/or amount of energy to be delivered by an energy delivery based treatment element. Dissimilarities in target tissue treatments can include: target tissue area treated; target tissue volume treated; target tissue length treated; target tissue depth treated; target tissue circumferential portion treated; ablative fluid type, volume and/or temperature delivered to a reservoir such as a balloon; ablative fluid type, volume and/or temperature delivered directly to tissue; energy delivery type; energy delivery rate and/or amount; peak energy delivered; average temperature of target tissue achieved during target tissue treatment; maximum temperature achieved during target tissue treatment; temperature profile of target tissue treatment; duration of target tissue treatment; surface area reduction achieved by target tissue treatment; and combinations of these.

Target tissue can include tissue of the duodenum, such as tissue including substantially all or a portion of the mucosal layer of one or more axial segments of the duodenum (e.g. including all or a portion of the plicae circulares), such as to treat diabetes and/or obesity while leaving the duodenum anatomically connected after treatment. Target tissue can include one or more portions of a tissue layer selected from the group consisting of: mucosa; mucosa through superficial submucosa; mucosa through mid-submucosa; mucosa through deep-submucosa; and combinations of these. Replacement tissue can comprise cells that have migrated from one or more of: gastric mucosa; jejunal mucosa; an untreated portion of the duodenum such as untreated duodenal mucosa whose mucosal tissue functions differently than the treated mucosal tissue functions prior to treatment; and combinations of these. Replacement tissue can include one or more tissue types selected from the group consisting of: scar tissue; normal intestinal mucosa; gastric mucosa; and combinations of these. In some embodiments, target tissue includes a treatment portion comprising the mucosal layer of the duodenum, and a safety-margin portion comprising a near-full or partial layer of the submucosal layer of the duodenum. In some embodiments, the target tissue comprises nearly the entire mucosal layer of the duodenum, and can include a portion of the pylorus contiguous with the duodenal mucosa and/or a portion of the jejunum contiguous with the duodenal mucosa. In other embodiments, the target tissue comprises up to 50% or up to 75% of the mucosal layer, such as when up to 50% or up to 75%, respectively, of the length of the duodenum is treated by an tissue treatment element delivering energy to full circumferential axial segment of the duodenum. In some embodiments, at least 6 cm, or at least 9 cm of length of duodenal mucosa is treated, such as with two or three treatments, respectively.

Treatment of duodenal tissue can be performed to treat a disease and/or disorder selected from the group consisting of: diabetes; pre-diabetes; impaired glucose tolerance; insulin resistance; obesity or otherwise being overweight; a metabolic disorder and/or disease; and combinations of these. A near full circumferential portion (e.g. approximately) 360° of the mucosal layer of one or more axial segments of GI tissue can be treated. In some embodiments, less than 360° of one or more axial segments of tubular tissue is treated, such as one or more circumferential portions less than 350°, or between 300° and 350°, such as to prevent a full circumferential scar from being created at the one or more axial segment locations.

Target tissue can be selected to treat two or more patient diseases or disorders, such as two or more patient diseases or disorders as described herein.

Target tissue can comprise tissue of the terminal ileum, such as to treat hypercholesterolemia and/or diabetes. In these embodiments, the target tissue can extend into the proximal ileum and/or the colon.

Target tissue can comprise gastric mucosal tissue, such as tissue regions that produce ghrelin and/or other appetite regulating hormones, such as to treat obesity and/or an appetite disorder.

Target tissue can comprise bladder wall tissue, such as to treat a disease and/or disorder selected from the group consisting of: interstitial cystitis; bladder cancer; bladder polyps; pre-cancerous lesions of the bladder; and combinations of these.

Target tissue can comprise tissue selected from the group consisting of: large and/or flat colonic polyps; margin tissue remaining after a polypectomy; and combinations of these. These tissue locations can be treated to treat residual cancer cells.

Target tissue can comprise esophageal tissue and/or gastric tissue. In some embodiments, target tissue comprises cancerous or precancerous tissue treated with a single or multiple energy deliveries, in single or multiple clinical procedures. In some embodiments, target tissue is treated as a treatment of Barrett's esophagus.

Target tissue can comprise airway lining tissue, such as to treat a disease and/or disorder selected from the group consisting of: bronchioalveolar carcinoma; other lung cancers; pre-cancerous lung lesions; and combinations of these.

Target tissue can comprise at least a portion of the intestinal tract afflicted with inflammatory bowel disease, such that Crohn's disease and/or ulcerative colitis can be treated.

Target tissue can comprise tissue of the oral cavity, such as to treat one or more of: oral cancers and a pre-cancerous lesion of the oral cavity.

Target tissue can comprise tissue of the nasopharynx, such as to treat nasal polyps.

Target tissue can comprise GI tissue selected to treat Celiac disease and/or to improve intestinal barrier function.

The treatment assemblies, treatment elements, systems, devices and methods of the present inventive concepts can be configured to avoid ablating or otherwise adversely affecting certain tissue, termed "non-target tissue" herein. Depending on the location of tissue intended for treatment (i.e. target tissue), different non-target tissue can be applicable. In certain embodiments, non-target tissue can comprise tissue selected from the group consisting of: gastrointestinal adventitia; duodenal adventitia; the tunica serosa; the tunica muscularis; the outermost partial layer of the submucosa; ampulla of Vater; pancreas; bile duct; pylorus; and combinations of these.

The treatment assemblies, treatment elements and other functional elements of the present inventive concepts can be configured to automatically and/or manually expand in at least a radial direction. Typical expandable elements include but are not limited to: an inflatable balloon; a radially expandable cage or stent; one or more radially deployable arms; an expandable helix; an unfurlable compacted coiled structure; an unfurlable sheet; an unfoldable compacted structure; and combinations of these. In some embodiments, the expandable elements can comprise a radially expandable tube, such as a sheet of material resiliently biased in a radially expanded condition that can be compacted through a furling operation, or a sheet of material resiliently biased in a radially compact condition that can be expanded through an unfurling operation. The expandable elements can comprise a foldable sheet, such as a sheet configured to be folded to be radially compacted and/or to be unfolded to radially expand. In some embodiments, the expandable elements expand to contact tissue, such as to expand to a diameter similar to the diameter of the luminal wall tissue into which the expandable element has been placed. In some embodiments, the expandable elements expand to be closer to wall tissue, but remain at a distance (e.g. a fixed or pre-determined distance) from the tissue surface. In some embodiments, the expandable elements expand to be larger than the diameter of the luminal wall tissue into which the expandable element has been placed, such as to improve the quality of the apposition of the expandable element against the uneven surface of the tissue. In these embodiments, the fully expanded diameter of the expandable elements would be configured to avoid a diameter large enough to cause lasting mechanical damage to the apposed tissue and/or to tissue proximate the apposed tissue.

Any device of the present inventive concepts can include one or more treatment elements configured to deliver energy to one or more energy delivery zones, to treat at least a portion of target tissue. Any device can include one or more fluid delivery elements, such as one or more nozzles or needles configured to deliver fluid toward and/or into tissue. The fluid delivery elements can be constructed and arranged to deliver fluid to perform a function selected from the group consisting of: expanding one or more tissue layers; warming or cooling tissue; removing debris or other substance from a tissue surface; delivering energy to an energy delivery zone comprising a continuous or segmented surface; treating target tissue; and combinations of these. Any of the expandable assemblies of the present inventive concepts can include one or more other functional elements (e.g. one or more sensors and/or transducers), such as are described in reference to the figures herebelow. The treatment elements, fluid delivery elements, and/or other functional elements can be mounted on, within (e.g. within the wall) and/or inside of an expandable element such as a balloon or expandable cage. In some embodiments, one or more functional elements is mounted on or within a different component of the treatment device (e.g. not mounted on ore within an expandable element), such as a functional element attached to a shaft or other non-expandable treatment device component.

In some embodiments, the treatment device comprises at least one treatment element configured to deliver energy to an energy delivery zone such as an ablation element configured to ablate target tissue. Examples of ablation elements include but are not limited to: an expandable reservoir such as a balloon configured to receive fluid at a temperature sufficient to ablate tissue; one or more fluid delivery elements configured to deliver ablative fluid directly to target tissue; a radiofrequency (RF) energy delivery element such as one or more electrodes; an ultrasonic transducer such as one or more piezo crystals configured to deliver ultrasound energy ablate tissue; a laser energy delivery element such as one or more optical fibers and/or laser diodes configured to deliver light energy to ablate tissue; a rotating ablation element; a circumferential array of ablation elements; and combinations of these.

The expandable elements of the present inventive concepts comprising balloons can be divided into two general categories: those that are composed of a substantially elastic material, such as silicone, latex, low-durometer polyurethane, and the like; and those that are composed of a substantially inelastic material, such as polyethylene terephthalate (PET), nylon, high-durometer polyurethane and the like. A third category includes balloons which include both elastic and inelastic portions. Within the category of elastic balloons, two subcategories exist: a first sub-category wherein a combination of material properties and/or wall thickness can be combined to produce a balloon that exhibits a measurable pressure-threshold for inflation (i.e. the balloon becomes inflated only after a minimum fluidic pressure is applied to the interior of the balloon); and a second sub-category, wherein the balloon expands elastically until an elastic limit is reached which effectively restricts the balloon diameter to a maximum value. The individual properties of the balloons in each of these categories can be applied to one or more advantages in the specific embodiments disclosed herein, these properties integrated singly or in combination. By way of example only, one or more of the following configurations can be employed: a highly elastic balloon can be used to achieve a wide range of operating diameters during treatment (e.g. during operation a desired balloon diameter can be achieved by adjustment of a combination of fluid temperature and pressure); a substantially inelastic balloon or a balloon that reaches its elastic limit within a diameter approximating a target tissue diameter (e.g. a duodenal mucosal diameter) can be used to achieve a relatively constant operating diameter that will be substantially independent of operating pressure and temperature; a balloon with a pressure-threshold for inflation can be used to maintain an uninflated diameter during relatively low pressure conditions of fluid flow and then achieve a larger operating diameter at higher pressure conditions of flow. Pressure-thresholded balloons can be configured in numerous ways. In one embodiment, a balloon is configured to have a relatively thick wall in its uninflated state, such as to maximize an electrically and/or thermally insulating effect while the balloon is maintained in this uninflated state. The balloon can be further configured such that its wall thickness decreases during radial expansion (e.g. to decrease an electrically and/or thermally insulating effect). In another embodiment, a balloon is configured to have a relatively small diameter in its uninflated state (e.g. a diameter that is small relative to the inner diameter of tubular target tissue such as the diameter of the mucosal layer of duodenal wall tissue), such as to minimize or completely eliminate apposition between the balloon and the surrounding tissue to minimize heat, RF and/or other energy transfer into the surrounding tissue until the balloon is fully inflated. In another embodiment, a balloon and an ablation system or device are configured to circulate a flow of fluid through the balloon (e.g. an elastic balloon or an inelastic balloon) at a sufficiently low enough pressure to prevent apposition of the balloon or other device component with target tissue, such as to pre-heat one or more surfaces of the ablation system or ablation device that are in fluid communication with the balloon. In this configuration, when the balloon or other ablation element is positioned to deliver energy to target tissue, the temperature of the balloon or other ablation element will be at a desired level or it will rapidly and efficiently reach the desired level for treatment (i.e. minimal heat loss to the fluid path components due to the pre-heating or pre-cooling). These configurations provide a method of delivering energy to tissue with an ablative fluid filled balloon. A "thermal priming" procedure can be performed prior to one or more target tissue treatments, such as to improve thermal response time of one or more portions of the treatment device. Ablative fluid filled balloon treatment devices as well as thermal priming devices and methods can be configured as is described in applicant's co-pending International PCT Application Serial Number PCT/US2013/28082, entitled "Heat Ablation Systems, Devices and Methods for the Treatment of Tissue", filed Feb. 27, 2013, the contents of which is incorporated herein by reference in its entirety.

A fluid evacuation procedure can be performed on one or more internal locations of the treatment devices and/or treatment elements of the present inventive concepts, such as when a negative pressure is applied to purge or otherwise evacuate fluid from one or more locations. A fluid evacuation procedure can be performed prior to a thermal priming procedure, prior to delivering ablative fluid to a treatment element, and/or prior to deliver a neutralizing fluid to a treatment element (e.g. a cold fluid to remove ablative heat from tissue or a warm fluid to bring tissue closer to body temperature after a cryogenic ablation procedure has been performed).

At times during target tissue treatment when it is desirable to initiate, increase and/or otherwise modify the treatment of tissue by one or more tissue treatment elements (e.g. a fluid delivery element delivering ablative fluid, a mechanically abrasive element, a hot or cold fluid balloon delivering a thermal energy to tissue and/or an electrode delivering RF energy), the diameter of the treatment assembly and/or treatment element (e.g. the diameter of a balloon, deployable cage, expandable tube or other expandable assembly) can be increased in situ to move a treatment element closer to target tissue and/or to change the contact force between the treatment element and the target tissue. At times during treatment when it is desirable to stop or otherwise decrease the amount of tissue treatment, the diameter of the treatment assembly and/or treatment element can be reduced in situ, such as to prevent or reduce delivery of energy or other treatment to the target tissue by eliminating or reducing tissue contact of one or more treatment elements (e.g. electrodes, abrasive surfaces or ablative fluid-filled balloons). For those cases where the native diameter of the target tissue varies substantially within an energy delivery zone, then a highly elastic or compliant balloon or other expandable element can be employed, such as a balloon or deployable cage which can be adjusted to achieve a wide range of operating diameters.

Alternatively or additionally, to initiate, increase and/or otherwise modify the treatment of tissue by one or more treatment elements (e.g. a fluid delivery element delivering ablative fluid, a mechanically abrasive element, a hot or cold fluid balloon delivering thermal energy to or from tissue and/or an electrode delivering RF energy), the diameter of the target tissue can be decreased in situ to move target tissue closer to a treatment element and/or to change the contact force between the target tissue and the treatment element. To stop or otherwise decrease ablation of tissue, the diameter of tissue neighboring a treatment element can be increased in situ, such as to prevent or reduce delivery of energy or other treatment to the target tissue by eliminating or reducing tissue contact of one or more treatment elements (e.g. electrodes, abrasive surfaces or ablative fluid filled balloons). The diameter of the tissue proximate a treatment element can be increased or decreased, independent of the treatment assembly diameter, by means of delivering and/or withdrawing a fluid, to and/or from a lumen surrounded by target tissue, such as by using standard GI insufflation and desufflation techniques (hereinafter insufflation). Typical insufflation fluids include but are not limited to: gases such as carbon dioxide or air; liquids such as water or saline solution; and combinations of these. The insufflation fluids can be introduced through a treatment device of the present inventive concepts, through an endoscope such as an endoscope through which the treatment device is inserted, and/or via another device placed proximate the target tissue. Delivery of insufflation fluids can be performed to move target tissue away from one or more treatment elements, such as to stop transfer of energy to target tissue at the end of a treatment of target tissue as described hereabove. Alternatively or additionally, delivery of insufflation fluids can be performed to manipulate tissue, such as to distend and/or elongate tissue. Removal of these insufflation fluids and/or the application of a vacuum or other negative pressure can be used to decrease the diameter of the target tissue, such as to bring the target tissue in closer proximity to one or more treatment elements and/or to increase the contact force between target tissue and one or more treatment elements, also as described hereabove. In this tissue diameter controlled approach, a treatment assembly including a balloon that can be maintained at a substantially constant diameter can be desirable, such as a substantially inelastic balloon such as a balloon with an elastic-limit.

Referring now to FIG. 1, a schematic view of a tissue treatment system is illustrated, consistent with the present inventive concepts. System 10 comprises treatment device 100 which can be configured to be inserted into an internal body location of a patient, such as into a gastrointestinal lumen of the patient via the mouth of the patient. Device 100 is shown in a side sectional view. System 10 further includes a fluid delivery assembly, energy delivery unit (EDU) 330, which is constructed and arranged to provide one or more fluids to device 100. Device 100 includes an elongate shaft, shaft 110 which includes distal portion 114. On the proximal end of shaft 110 is handle 105. Mounted to distal portion 114 is a treatment element, expandable reservoir 140, shown in an expanded state. Distal to expandable reservoir 140 is tip portion 112. Tip portion 112 can comprise a smaller diameter than the diameter of shaft 110 proximal to expandable reservoir 140, as shown. Expandable reservoir 140 can comprise a balloon constructed of compliant and/or non-compliant materials as described hereabove. In some embodiments, expandable reservoir 140 comprises a compliant balloon. In some embodiments, expandable reservoir 140 comprises a balloon with a compliant portion and a non-compliant portion or a non-compliant balloon. One or more fluids are provided to and/or removed from expandable reservoir 140 by a fluid delivery passage of the present inventive concepts, lumen 111. Expandable reservoir 140 is fluidly attached to lumen 111, which travels proximally through shaft 110 to an internal location of handle 105 and an attachment port, port 106. System 10 can be constructed and arranged to treat target tissue by delivery of hot and/or cold fluid to expandable reservoir 140 such that tissue in contact with expandable reservoir is ablated and/or otherwise modified as described hereabove. System 10 can be constructed and arranged to neutralize the target tissue treatment by further delivery of a cold and/or warm fluid to expandable reservoir 140, to minimize and/or reduce the effects of delivery of an ablative hot and/or cold ablative fluid, respectively. In some embodiments, a neutralizing cold fluid is delivered to reservoir 140 prior to and/or after delivery of a sufficiently hot ablative fluid, such as to pre-cool and/or post-cool, respectively, the target tissue and tissue proximate the target tissue. In some embodiments, a neutralizing warm fluid is delivered to reservoir 140 prior to and/or after delivery of a sufficiently cold ablative fluid, such as to pre-warm and/or post-warm, respectively, the target tissue and tissue proximate the target tissue.

Expandable reservoir 140 can comprise a balloon or other expandable membrane with a wall thickness of less than or equal to 0.002", or less than or equal to 0.001". Expandable reservoir 140 can comprise a material selected from the group consisting of: polyether block amide (PEBAX); nylon; polyethylene terephthalate (PET); silicone; latex; and combinations of these. In some embodiments, expandable reservoir 140 comprises an expanded volume between 10 ml and 50 ml. In some embodiments, expandable reservoir 140 comprises an expanded diameter of at least 17 mm, such as at least 20 mm, at least 22 mm or at least 25 mm. Expandable reservoir 140 can comprise a cylindrical portion, cylindrical portion 142, and two tapered portions 143a and 143b as shown in FIG. 1. Cylindrical portion 142 (e.g. a tissue contacting portion) can comprise a length of at least 10 mm, such as at least 20 mm or at least 25 mm. Cylindrical portion 142 can comprise a length of less than or equal to 60 mm, such as less than or equal to 45 mm or 30 mm. Positioned on each end of cylindrical portion 142 can be first end portion 143a and second end portion 143b. First end portion 143a and/or second end portion 143b can comprise tapered profiles, such as similar or dissimilar tapered profiles (similar tapered profiles shown).

Shaft 110 can be a flexible shaft, a rigid shaft, or a shaft with both flexible and rigid portions. Shaft 110 can be configured for insertion through and/or alongside an endoscope, such as described in reference to FIG. 12 herebelow. Shaft 110 can comprise a length of at least 100 cm, such as a length of approximately 135 cm. Shaft 110 can comprise a diameter less than or equal to 13 mm, such as a diameter less than or equal to 6 mm or less than or equal to 3 mm. Shaft 110 can comprise one or more of a braided shaft, a multiple layer shaft and/or a steerable shaft, such as is known to those of skill in the art. Shaft 110 can comprise an insulating element configured to reduce heat transfer to or from lumen 111 of shaft 110. In some embodiments, shaft 110 is surrounded by a second shaft, such as is described in reference to device 100 of FIGS. 5, 6 and 8 herebelow. One or more circulating fluids can be positioned between the surrounding shaft and shaft 110, such as one or more liquids or gases used to cool and/or warm shaft 110, such as to prevent undesired energy transfer from shaft 110 to neighboring tissue and/or a separate device, and/or to thermally prime shaft 110.

In some embodiments, shaft 110 comprises a relatively non-compliant tube and/or is otherwise configured to prevent collapse of one or more internal lumens such as lumen 111. In other embodiments, shaft 110 can comprise a compliant tube configured to be radially compacted (e.g. fully or partially radially compacted), such as via application of an internal negative pressure and/or an external pressure, as is described in detail herebelow in reference to FIGS. 4, 7 and 8 herebelow. Shaft 110 can comprise a material selected from the group consisting of: polyether block amide (PEBAX); nylon; polyethylene terephthalate (PET); silicone; and combinations of these. In some embodiments, a mechanism within and/or outside lumen 111 is used to cause lumen 111 and/or shaft 110 to be radially compacted.

In some embodiments, device 100 comprises a single fluid delivery passage, such as lumen 111, configured to provide fluids to expandable reservoir 140 and withdraw fluids from expandable reservoir 140. These single fluid passage embodiments allow a reduced diameter of device 100. In these embodiments, lumen 111 may comprise a diameter of at least 0.050" in an uncompacted state, such as an uncompacted diameter of at least 0.050" or at least 0.075", or an uncompacted diameter of approximately 0.100".

Figure 7:
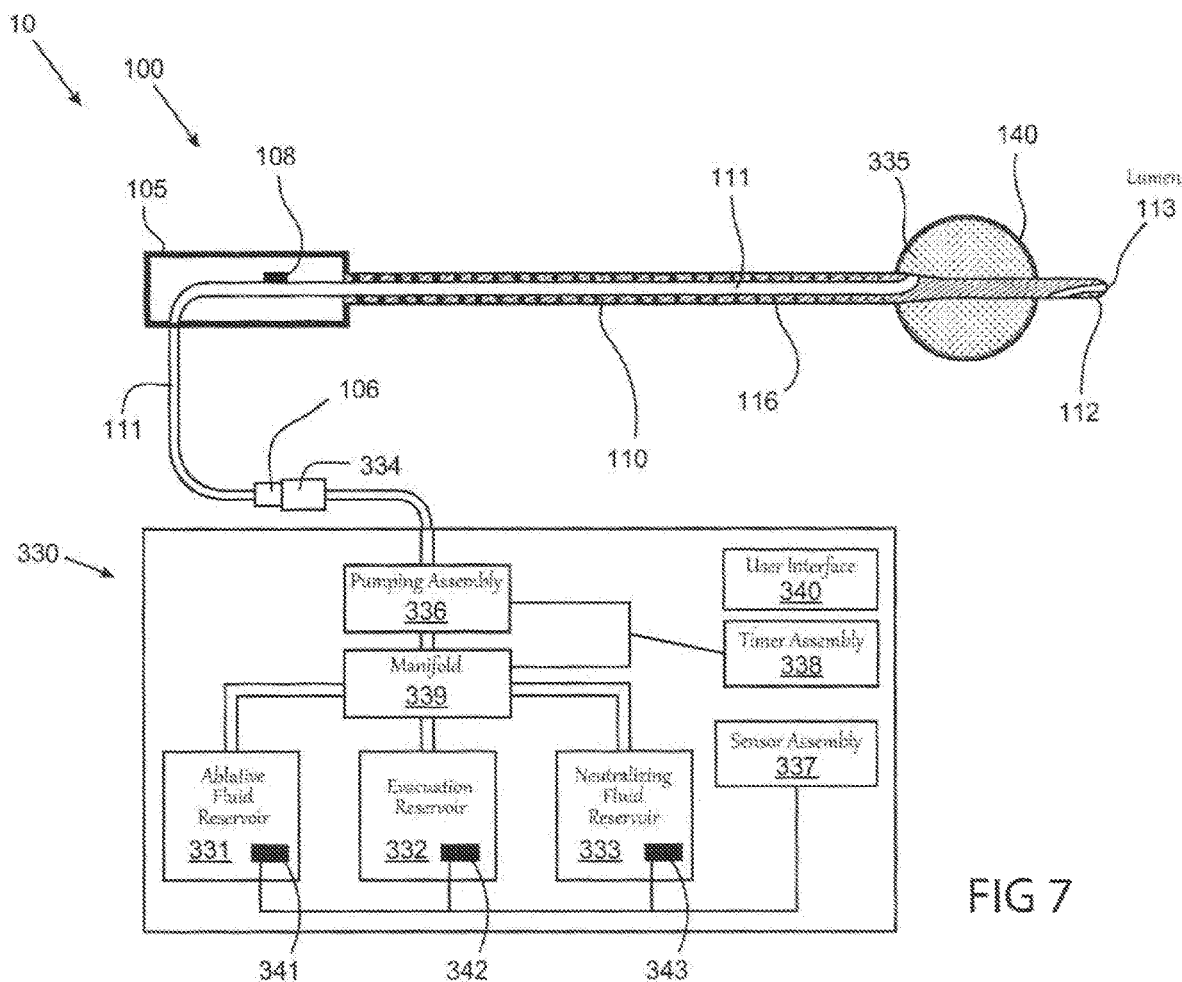
FIG. 7 is a schematic view of a tissue treatment system including a treatment device comprising a shaft with an internal coil, consistent with the present inventive concepts.

In some embodiments, shaft 110 is surrounded by a coil, such as is described in reference to FIG. 7 herebelow. In some embodiments, shaft 110 is surrounded by an insulator, such as is described in reference to FIG. 5 herebelow. In some embodiments, a second fluid passage of the present inventive concepts surrounds or is otherwise positioned outside of shaft 110, such as is described in reference to FIG. 8 herebelow. In some embodiments, device 100 comprises a heating element, not shown but such as is a heating element positioned in expandable reservoir 140 and/or shaft 110 as described in reference to FIG. 9 herebelow. In some embodiments, device 100 comprises a fluid mixing element, not shown but such as a mixing element positioned in expandable reservoir 140, shaft 110 and/or a location proximate to shaft 110 as is described in reference to FIG. 10 herebelow. In some embodiments, device 100 comprises a tissue expansion assembly, such as tissue expansion assembly 170 of FIG. 11 described herebelow. In some embodiments, device 100 and/or system 10 comprise a luminal sizing assembly, such as expandable reservoir 140 and/or a separate device as described in reference to FIG. 12 herebelow.

Device 100 can be configured for insertion over a guidewire, such as a guidewire inserted through one or more lumens of device 100, such as lumen 113 which has a proximal end that enters through a side wall of tip portion 112 and a distal end that exits the distal end of tip portion 112, as shown. Lumen 113 is configured for rapid exchange delivery and removal of device 100 over a guidewire, as is well known to those of skill in the art. Alternatively, lumen 113 can travel to a proximal portion of shaft 110.

EDU 330 is constructed and arranged to provide one or more fixed amounts of ablative fluid 335 to device 100. Each fixed amount of ablative fluid 335 is provided at an ablative temperature (e.g. a sufficiently hot or cold temperature) to device 100. EDU 330 includes an attachment port 334, configured to fluidly attach to port 106 such that EDU 330 can deliver one or more fluids to lumen 111 and expandable reservoir 140.

EDU 330 includes a source of fluid at an ablative temperature, ablative fluid reservoir 331, which is configured to warm, cool and/or maintain one or more fluids at a predetermined ablative temperature or range of ablative temperatures. In some embodiments, EDU 330 is configured to provide one or more fluids at an ablation neutralizing temperature, as has been described hereabove, such as to cool or warm tissue prior to and/or after a heat ablation or a cryogenic ablation, respectively. Ablative fluid reservoir 331 can be fluidly connected to a first input of a fluid control assembly, manifold 339. An output of manifold 339 can be fluid attached to a pump, pumping assembly 336, such that liquid provided by ablative fluid reservoir 331 can be directed through manifold 339 into pumping assembly 336, and propelled by pumping assembly 336 in a forward direction into device 100 via port 334. Fluid introduced into device 100 travels via port 106 into lumen 111 and/or into expandable reservoir 140.

EDU 330 can include a fluid evacuation assembly comprising at least a portion of pumping assembly 336 and a fluid storage chamber, evacuation reservoir 332. Evacuation reservoir 332 can be fluidly connected to a second input of manifold 339. Manifold 339 can be configured to selectively connect evacuation reservoir 332 to pumping assembly 336, such that pumping assembly 336 can propel fluid in a reverse direction from device 100, via port 334, into evacuation reservoir 332, such as to remove ablative fluid, neutralizing fluid, and/or other fluid from device 100 (e.g. remove fluid via port 106 from lumen 111 and/or expandable reservoir 140). System 10 can be constructed and arranged to perform a fluid evacuation procedure, such as to evacuate fluid from one or more internal locations of treatment device 100, such as by removing liquid or gas from expandable reservoir 140 and/or lumen 111 by applying a negative pressure via pumping assembly 336 or another device (e.g. a syringe) to lumen 111. In these fluid evacuation procedures, the captured fluid can be propelled into evacuation reservoir 332 or another temporary storage location. During fluid evacuation, EDU 330 can be constructed and arranged to create a pressure differential between EDU 330 (e.g. at pumping assembly 336) and expandable reservoir 140 of approximately 1 atmosphere. EDU 330 can be constructed and arranged to perform fluid evacuation of device 100 at a flow rate of at least 750 ml/min, or at least 1000 ml/min.

As described hereabove, EDU 330 can comprise a second source of fluid, neutralizing fluid reservoir 333. Neutralizing fluid reservoir 333 can be fluidly connected to a third input of manifold 339. Manifold 339 can be configured to selectively connect neutralizing fluid reservoir 333 to pumping assembly 336, such that liquid provided by neutralizing fluid reservoir 333 can be directed through manifold 339 into pumping assembly 336, and propelled by pumping assembly 336 in a forward direction into device 100 via port 334. Fluid introduced into device 100 travels via port 106 into lumen 111 and/or into expandable reservoir 140. Neutralizing fluid from neutralizing fluid reservoir 333 can be delivered to lumen 111 and/or expandable reservoir 140 prior to and/or after delivery of ablative fluid to expandable reservoir 140.

EDU 330 can comprise one or more sensors such as sensor 341 positioned to measure a temperature related to ablative fluid reservoir 331, sensor 342 positioned to measure a temperature related to neutralizing fluid reservoir 333 and/or sensor 343 positioned to measure a temperature related to evacuation reservoir 332. Sensors 341, 342 and/or 343 can be attached to a sensor interface assembly, sensor interface 337.

Device 100 can comprise one or more sensors, such as one or more sensors 149 positioned proximate expandable reservoir 140, such as to provide a signal representing the temperature of at least a portion of expandable reservoir 140 and/or a fluid residing within expandable reservoir 140. Sensor 149 can be positioned on the inner surface of, on the outer surface of and/or within the wall of expandable reservoir 140. Alternatively or additionally, device 100 can comprise one or more sensors 119 positioned in, within, on and/or proximate shaft 110, such as to measure the temperature of the outer surface of shaft and/or of fluid within lumen 111. Alternatively or additionally, device 100 can comprise one or more sensors 109 positioned proximate handle 105, such as to measure the temperature of a portion of handle 105 and/or fluid residing within handle 105. Sensors 109, 119 and/or 149 can be operably connected to one or more wires or other conduits, not shown but traveling proximally to port 106 and operably connecting to sensor interface 337 of EDU 330.

Sensor interface 337 can monitor the temperature from one or more of sensors 109, 119, 149, 341, 342 and/or 343 and adjust one or more operating parameters of EDU 330 and/or other component of system 10. In some embodiments, the one or more operating parameters adjusted are selected from the group consisting of: temperature of ablative fluid in ablative fluid reservoir 331; temperature of neutralizing fluid in neutralizing fluid reservoir 333; flow rate of pumping assembly 336; on time of pumping assembly 336; volume of fluid delivered by pumping assembly 336 into expandable reservoir 140; volume of fluid extracted from device 100 and propelled into evacuation reservoir 332; and combinations thereof. One or more of sensors 109, 119, 149, 341, 342 and 343 can comprise a sensor selected from the group consisting of: thermocouple; thermistor; resistance temperature detector; and combinations of these.

EDU 330 can further comprise an electronic timer module, timer assembly 338 constructed and arranged to turn on, turn off and/or regulate one or more functions of pumping assembly 336 and/or manifold 339. Manifold 339 can comprise one or more valves, such as one or more valves controlled by timer assembly 338 and used to selectively connect one or more of ablative fluid reservoir 331, neutralizing fluid reservoir 333 and/or evacuation reservoir 332 to pumping assembly 336. Pumping assembly 336 can comprise one or more pumping mechanisms, such as one or more positive pressure pumps, peristaltic pumps, rotary pumps, displacement pumps, manual pumps (e.g. a syringe) or other pumping mechanisms. The one or more pumping mechanisms can be controlled by timer assembly 338, such as to turn on or off, or to regulate the fluid flow rate through pumping assembly 336.

EDU 330 is constructed and arranged to deliver the fixed amount of ablative fluid 335 into expandable reservoir 140, such as a fixed amount of ablative fluid extracted from ablative fluid reservoir 331 through manifold 339 and propelled by pumping assembly 336 into expandable reservoir 140 via port 106 and lumen 111. The fixed amount of ablative fluid 335 can comprise a fixed mass or a fixed volume of fluid. The fixed amount of fluid 335 can be provided at a pre-determined temperature or at a temperature within a pre-determined temperature range. The fixed amount of ablative fluid 335 is configured to apply a thermal dose of energy (e.g. a first thermal dose of energy) to target tissue (e.g. a first portion of target tissue). In some embodiments, multiple fixed volumes of ablative fluid 335 are each delivered sequentially to one or more target tissue portions (e.g. a series of unique target tissue portions), such as is described in reference to FIGS. 2 and 3 hereinbelow. The target tissue can include tissue of gastrointestinal tract, such as mucosal tissue of the duodenum or other tissue as has been described in detail hereinabove.

The fixed amount of fluid 335 can be configured to deliver a thermal dose of heat energy to a portion of target tissue, such as when the fixed amount of ablative fluid 335 is provided to expandable reservoir 140 at a temperature above body temperature (e.g. above 37° C.). Alternatively, the fixed amount of fluid 335 can be configured to remove heat energy from a portion of target tissue, such as when the fixed amount of fluid 335 comprising a fixed amount of neutralizing fluid provided to expandable reservoir 140 at a temperature below body temperature (e.g. below 37° C.). The fixed amount of fluid 335 can comprise a fixed volume of fluid, such as a volume of fluid between approximately 10 ml and 100 ml, or a volume of less than or equal to 50 ml. The fixed amount of fluid 335 can comprise a fixed mass of fluid, such as a mass of fluid between approximately 10 g and 100 g, or a mass less than or equal to 50 g. In hot fluid embodiments, the fixed amount of ablative fluid 335 can be delivered to expandable reservoir at a temperature above 80° C., such as at a temperature above 85° C. or above 90° C. The fixed amount of ablative fluid 335 can be delivered at a temperature sufficiently low to prevent an undesired effect, such as tissue desiccation and/or steam formation. In these embodiments, the fixed amount of ablative fluid 335 can be delivered at a temperature less than 105° C., or less than 101° C. In cryogenic embodiments, the fixed amount of ablative fluid 335 can be delivered to expandable reservoir at a temperature less than or equal to 0° C. EDU 330 can comprise a user interface 340 configured to allow a clinician or other operator to adjust one or more parameters of system 10, such as the temperature of the fixed amount of ablative fluid 335, or the duration in which ablative fluid 335 delivers energy to tissue.

The fixed amount of fluid 335 can comprise one or more liquids, gases or gels, such as a fluid selected from the group consisting of: water; saline; glycerin; oil; a dye such as methylene blue or indigo carmine; and combinations thereof.

Device 100 and/or EDU 330 can be constructed and arranged to maintain expandable reservoir 140 within a range or pressures and/or at or below a maximum pressure, such as when expandable reservoir 140 is in contact with tissue. In some embodiments, expandable reservoir 140 is maintained below a pressure of 4.0 psi, such as a pressure below 3.2 psi, below 2.4 psi, below 1.6 psi or below 1.0 psi.

In some embodiments, expandable reservoir 140 is maintained at or above a minimum pressure when a thermal dose is being delivered by expandable reservoir 140 to target tissue (e.g. to maintain sufficient apposition with tissue), such as a pressure of at least 0.2 psi, such as a pressure of at least 0.3 psi, 0.35 psi, 0.6 psi or at least 0.7 psi.

Expandable reservoir 140 can be maintained in contact with target tissue during the delivery of the thermal dose for a minimum time period, such as a time period selected such that all or a majority of the energy transfer takes place (e.g. additional contact time would have minimal or no effect). In these embodiments, the contact time of expandable reservoir 140 with target tissue can be at least 0.5 seconds, at least 1.0 seconds, at least 3.0 seconds. In some embodiments, system 10 is constructed and arranged to cause a minimum period of contact of expandable reservoir 140 with target tissue during delivery of the thermal dose. In some embodiments, expandable reservoir 140 can be removed from contact with target tissue prior to a maximum time period of contact, such as a maximum time period of less than or equal to 10 seconds or less than or equal to 6 seconds. In some embodiments, system 10 can be configured to deliver the thermal dose for a target time period, such as a time period between approximately 0.5 seconds and 120 seconds. System 10 can be configured to radially compact expandable reservoir 140 (e.g. by withdrawing fluid from expandable reservoir 140) after the target time period has been reached. In some embodiments, system 10 is constructed and arranged to stop (e.g. automatically or manually) the delivery of the energy to and/or from target tissue by removing contact of expandable reservoir 140 with target tissue prior to the maximum time period, such as by deflating expandable reservoir 140 (e.g. via pumping assembly 336) and/or radially expanding the contacted target tissue (e.g. via insufflation as described hereabove).

In some embodiments, system 10 is constructed and arranged to deliver a neutralizing fluid to slow down, stop and/or otherwise reduce the effects of the thermal dose delivered by the fixed amount of ablative fluid 335 provided to expandable reservoir 140. Alternatively or additionally, system 10 can be constructed and arranged to deliver a neutralizing fluid prior to delivery of the ablative fluid 335 to expandable reservoir 140. The neutralizing fluid can be delivered by pumping assembly 336 from neutralizing fluid reservoir 333, such as after pumping assembly 336 has pumped fluid (e.g. at least a portion of fixed amount of ablative fluid 335) from expandable reservoir 140 into evacuation reservoir 332. A majority of the fixed amount of ablative fluid 335 can be removed by pumping assembly 336 prior to providing neutralizing fluid. In some embodiments, the portion of fixed amount of ablative fluid 335 removed from expandable reservoir 140 is removed in a time period less than or equal to 5 seconds. In some embodiments, the neutralizing fluid provided to expandable reservoir 140 is delivered in a time period of less than or equal 5 seconds. The neutralizing fluid can be a cooling fluid configured to reduce the effects of heat ablation or a warming fluid configured to reduce the effect of cryogenic ablation.

In some embodiments, system 10 is constructed and arranged to deliver a fixed volume of neutralizing fluid, such as a fixed volume or a fixed mass of neutralizing fluid delivered by pumping assembly 336 from neutralizing fluid reservoir 333. Neutralizing fluid can be provided to cool tissue (e.g. between two hot fluid thermal dose treatments), such as when the neutralizing fluid comprises a fluid provided at a temperature of less than or equal to 37° C., such as less than or equal to 7° C., less than or equal to 4° C. or less than or equal to 0° C. Alternatively, neutralizing fluid can be provided to warm tissue (e.g. between two cryogenic thermal dose treatments), such as when the neutralizing fluid comprises a fluid provided at a temperature of more than or equal to 37° C., such as more than or equal to 41° C., or more than or equal to 45° C.

In some embodiments, system 10 is constructed and arranged to treat a first portion of target tissue in a time period of less than or equal to 90 seconds, such as a time period of less than or equal to 60 seconds, or a time period between 20 and 60 seconds. In some embodiments, multiple thermal doses are delivered to a first portion of target in less than 20 seconds, such as less than 10 seconds or less than 6 seconds. In some embodiments, a single thermal dose from a single fixed amount of ablative fluid 335 is delivered in the time period. In other embodiments, multiple thermal doses from multiple fixed amount of ablative fluid 335's are delivered in the time period. System 10 can be constructed and arranged to deliver multiple thermal doses to the same or different portions of target tissue, such as the same or different axial segments of GI mucosal tissue treated in a single step or multiple steps. Two thermal doses can each comprise a delivery time period of less than 30 seconds, or less than 20 seconds. Neutralizing fluid can be delivered to target tissue between a first thermal dose delivery and a second thermal dose delivery. Neutralizing fluid can be delivered before and/or after each thermal dose delivery. In some embodiments, at least three thermal doses are delivered to a first portion of target tissue, such as at least three thermal doses delivered by at least three fixed amounts of ablative fluid 335's. The at least three thermal doses of energy can comprise similar or dissimilar doses of energy delivered to the first portion of target tissue.

In some embodiments, at least three thermal doses of energy are delivered to at least three relatively different portions of target tissue, such as a first thermal dose delivered to a first portion of target tissue, a second thermal dose delivered to a second portion of target tissue, and a third thermal dose delivered to a third portion of target tissue. The three portions of target tissue can each comprise an axial length of at least 2 cm, such as at least 3 cm. The first, second and third portions of target tissue can comprise similar and/or overlapping boundaries, such as is described in reference to FIG. 3 herebelow. The at least three thermal doses of energy can be delivered to target tissue in less than 45 seconds, such as less than 30 seconds.

System 10 and/or pumping assembly 336 can be constructed and arranged to fill expandable reservoir 140 with the fixed amount of ablative fluid 335 in a time period of less than 5 seconds, such as less than 2 seconds, less than 1 second or less than 0.5 seconds. System 10 and/or pumping assembly 336 can be constructed and arranged to remove a majority of fluid from expandable reservoir 140 in a time period of less than 5 seconds, such as less than 2 seconds, less than 1 second or less than 0.5 seconds.

EDU 330 and pumping assembly 336 can be constructed and arranged to deliver one or more fluids to treatment device 100 at a pre-determined flow rate and/or an adjustable flow rate (e.g. a flow rate adjustable via user interface 340). In some embodiments, pumping assembly 336 is constructed and arranged to deliver ablative fluid and/or neutralizing fluid at a flow rate of at least 2000 ml/min, such as a flow rate of at least 2500 ml/min.

Figure 12:
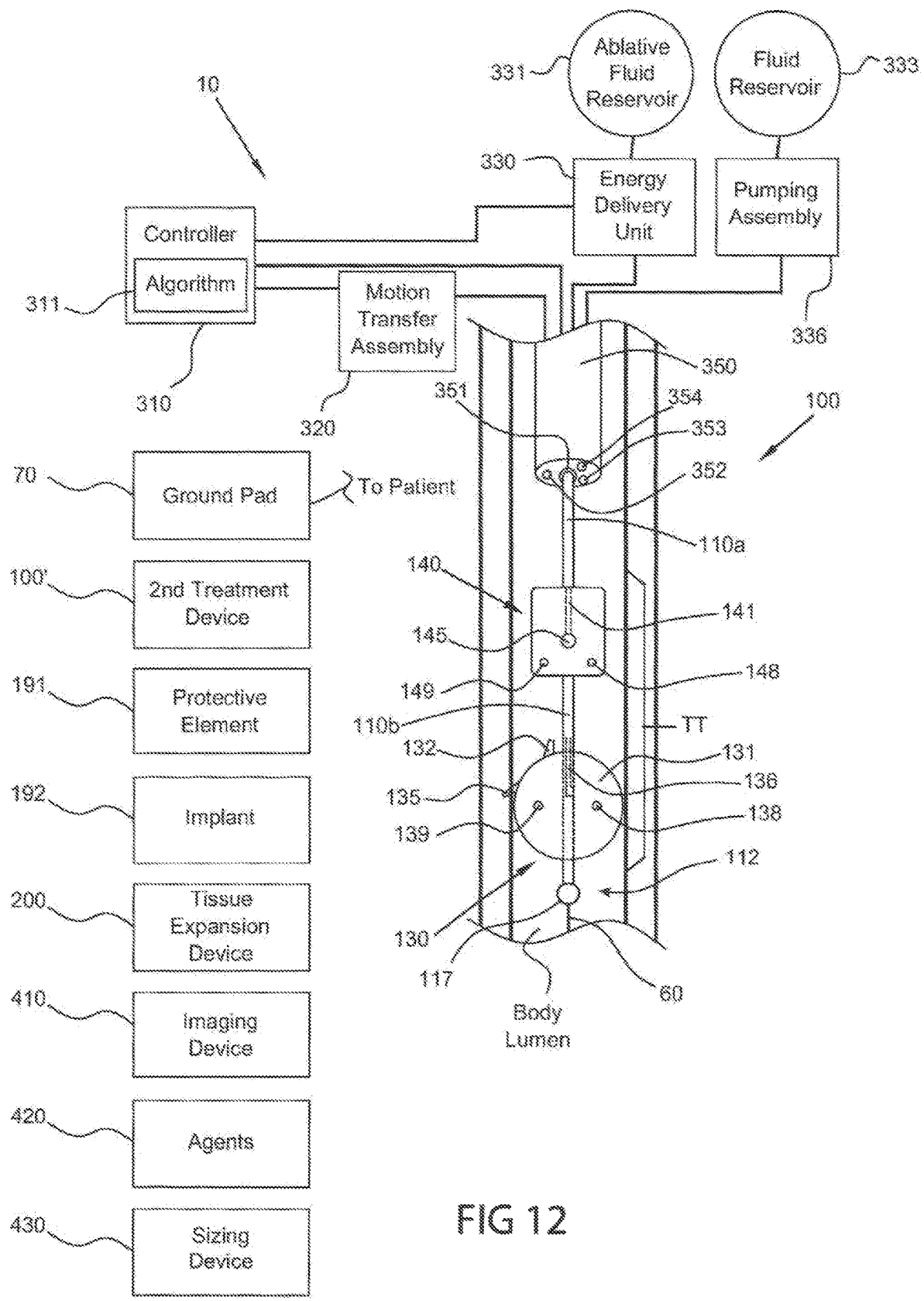
FIG. 12 is a schematic view of a system for ablating or otherwise treating target tissue, consistent with the present inventive concepts.

In some embodiments, system 10 comprises a second treatment device, such as described in reference to FIG. 12 herebelow. The second treatment device can comprise a component constructed and/or arranged in a different way than a similar component of device 100 of FIG. 1. For example, a second treatment device can comprise an expandable reservoir with a different diameter and/or length than expandable reservoir 140 of device 100 of FIG. 1.

Figure 2:
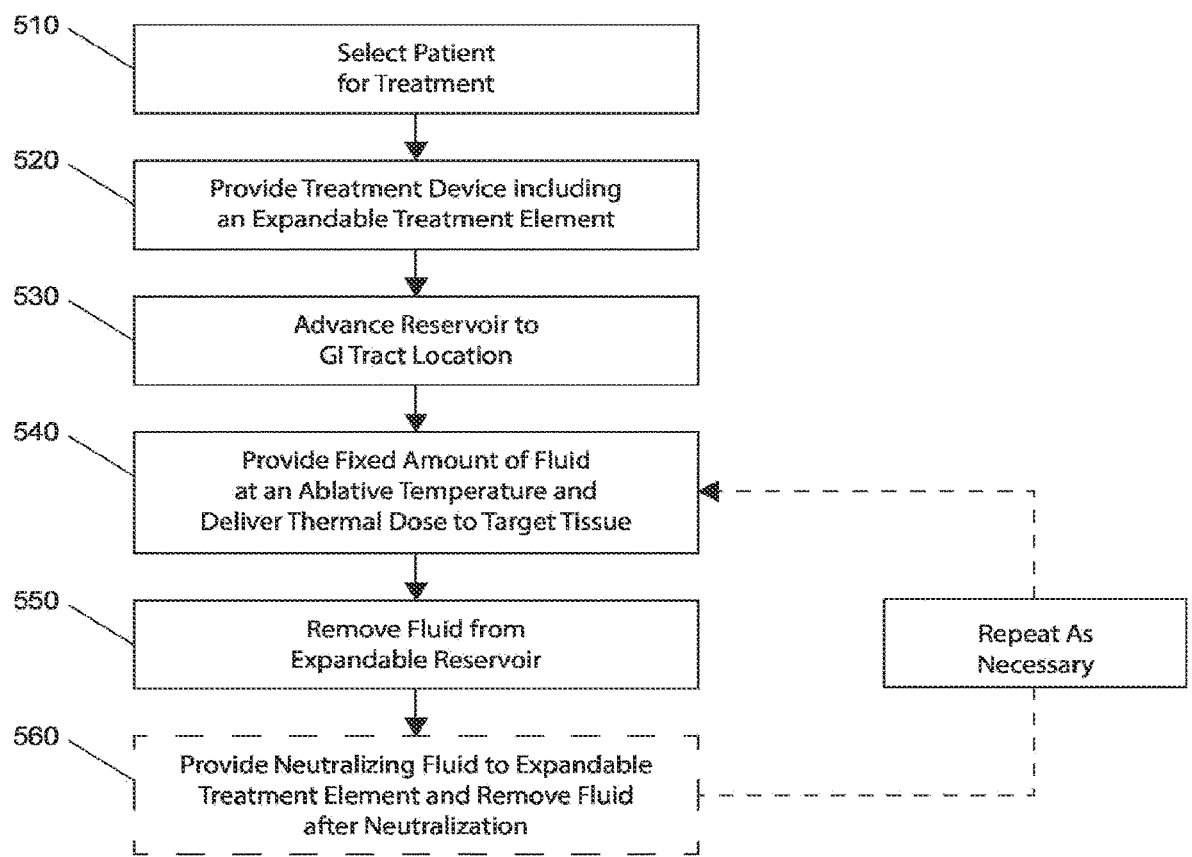
FIG. 2 is a flow chart of a method of delivering a fixed amount of fluid to deliver a thermal dose to target tissue of a patient, consistent with the present inventive concepts.

Referring now to FIG. 2, a flow chart of a method of delivering a fixed amount of fluid to deliver a thermal dose to target tissue of a patient is illustrated, consistent with the present inventive concepts. In STEP 510, a patient is selected for treatment. The patient may receive the treatment of the present inventive concepts to treat diabetes and/or another disease or disorder as listed and described in detail hereabove.

In STEP 520, a treatment device including an expandable treatment element is provided, such as device 100 including expandable reservoir 140, as described hereabove in reference to FIG. 1.

In STEP 530, the treatment element is advanced to a gastrointestinal tract or other location of body tissue (e.g. luminal body tissue) that includes target tissue or a portion of target tissue (hereinafter "target tissue") to be treated.

In STEP 540 a fixed amount of fluid is provided to the treatment element. The fixed amount of fluid can be provided to the treatment element at a predetermined temperature or range of temperatures as has been described hereabove (e.g. fluid at an ablative temperature sufficiently warm enough or cold enough to cause a modification to the tissue contacted by the treatment element). The fixed amount of fluid can be provided manually, such as via a syringe or simple fluid delivery system, or via a temperature modifying and/or pumping assembly such as EDU 330 of FIG. 1 described hereabove. In some embodiments, a thermal priming procedure, as described hereabove, is performed prior to the providing of the fixed amount of fluid to the treatment element. The priming procedure can be performed by delivering priming fluid at a temperature similar or dissimilar to the temperature of fixed amount of ablative fluid 335 provided by EDU 330. In some embodiments, a neutralizing fluid is delivered prior to and/or after delivery of the ablative fluid, such as to pre-cool or post-cool target tissue that is heat ablated. In some embodiments, pumping assembly 336 comprises two or more fluid delivery assemblies, such as fluid delivery assemblies configured to pump ablative fluid, thermal priming fluid and/or neutralizing fluid. In some embodiments, thermal priming fluid is provided from ablative fluid reservoir 331 and/or neutralizing fluid reservoir 333. In other embodiments, thermal priming fluid is provided from a separate reservoir of EDU 330, not shown. A vacuum or other negative pressure can be applied to withdraw fluid from the treatment device, such as prior to or after a thermal priming procedure. At least a portion of target tissue is treated by the heat transfer that takes place between the target tissue and the treatment element. In some embodiments, the providing of the fixed amount of fluid causes the treatment element to come into apposition with the target tissue. In other embodiments, the target tissue can be brought into contact with the treatment element, such as by using one or more insufflation techniques as described hereabove.

In some embodiments, prior to the target tissue treatment by the fixed amount of ablative fluid, a tissue expansion procedure is performed, such as a submucosal tissue expansion performed at one or more locations of the GI tract. The tissue expansion procedure can be performed by the treatment device, as is described in reference to FIGS. 11 and 12 herebelow, or by a separate device, such as is described in applicant's co-pending application International Patent Application Serial Number PCT/US2013/37485, entitled "Tissue Expansion Devices, System and Methods", filed Apr. 19, 2013, the contents of which is incorporated by reference in its entirety. Tissue expansion can be performed multiple times throughout the method of the present inventive concepts, typically prior to target tissue treatment in a similar area. In some embodiments, confirmation of successful tissue expansion is performed (e.g. visually via an endoscope) prior to treatment of the target tissue with the ablative fluid.

In STEP 550, some or all of the fluid is removed from the treatment element, such as manually via a syringe or other simple fluid extraction device, or via a pumping mechanism such as pumping assembly 336 of FIG. 1 described hereabove. A vacuum or other negative pressure may be applied to one or more lumens of the treatment device, such as to remove fluid from one or more lumens of the treatment device.

In some embodiments, STEP 560 is performed in which a neutralizing fluid is provided to the treatment element, such as a fluid at a temperature to cool previously heated tissue or warm previously cooled tissue to slow, stop and/or reverse any tissue modifying effects still in process from the ablative fluid treatment of STEP 540. Alternatively or additionally, STEP 560 can be performed prior to STEP 540, such as to pre-cool or pre-warm tissue, as has been described hereabove.

In some embodiments, STEPs 540 and 550, and potentially 560, are repeated, such as to provide a tissue treatment at the same or different location of target tissue. In some embodiments, a series of sequentially target tissue portions comprise a set of similar, proximate and/or overlapping boundaries (e.g. proximal and distal edges), as is described in reference to FIG. 3 herebelow. In some embodiments, at least 6 cm or at least 9 cm of axial length of target tissue is treated, such as in a single step, or in two, three or more discrete steps.

Figure 3:
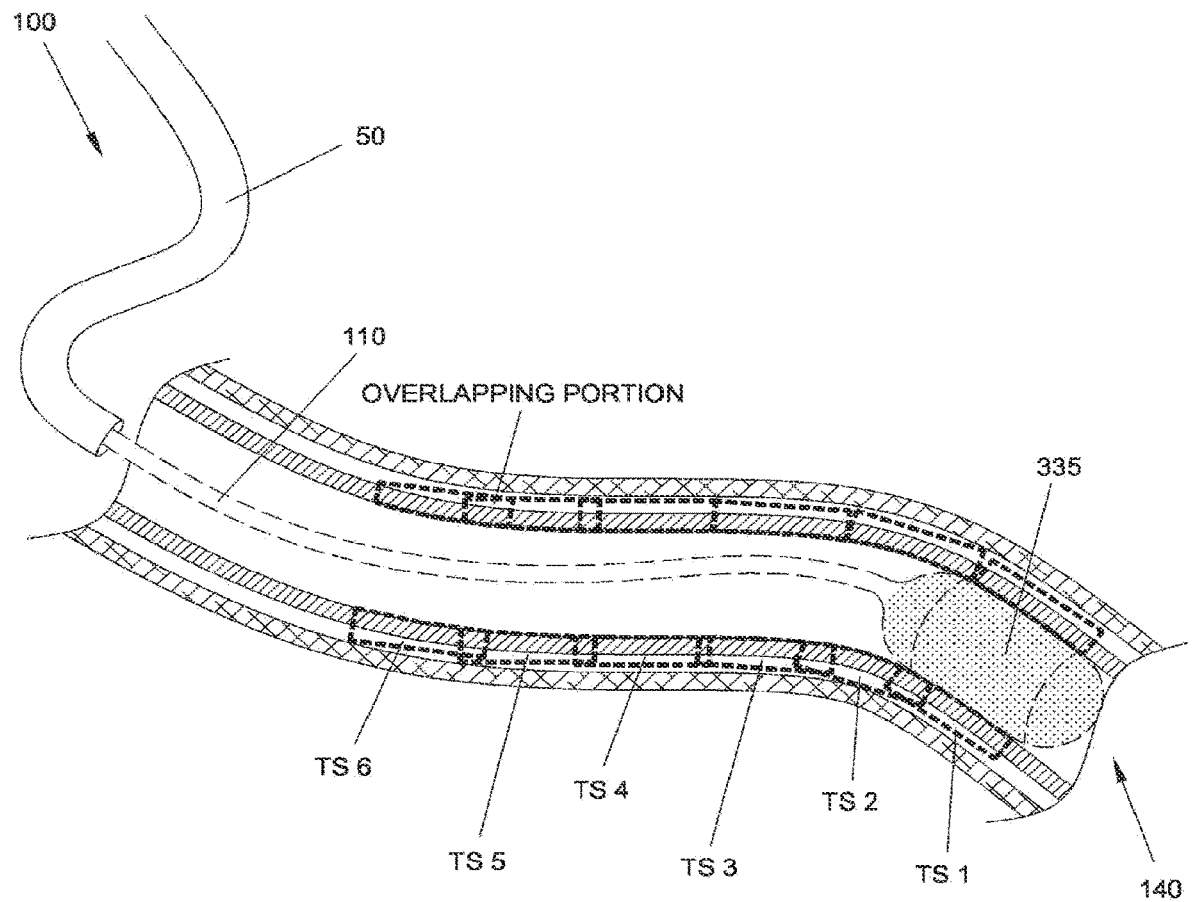
FIG. 3 is a side sectional view of the distal portion of a treatment device inserted into a curvilinear section of duodenum, consistent with the present inventive concepts.

Referring now to FIG. 3, a side sectional view of the distal portion of a treatment device inserted into a curvilinear section of duodenum is illustrated, consistent with the present inventive concepts. Treatment device 100 comprises shaft 110, a relatively flexible, biocompatible, elongate structure configured for insertion into a body lumen such as the duodenal tissue shown. Shaft 110 is typically connected to a handle on its proximal end, not shown but configured to allow an operator to advance, retract and otherwise manipulate and/or control treatment device 100, such as described in reference to FIG. 1 hereabove. Treatment device 100 can be configured for delivery over a guidewire, via a lumen from a proximal portion to a distal portion, or via a rapid exchange sidecar or other lumen in the distal portion of the device (guidewire lumen and sidecar not shown but known to those of skill in the art). Shaft 110 is shown inserted through introducer 50 which can comprise an endoscope, sheath, or other body introduction device.

Treatment device 100 further comprises a treatment element, expandable reservoir 140, which can be similar to expandable reservoir 140 of FIG. 1. A fixed amount of ablative fluid 335 has been delivered to expandable reservoir 140, as described hereabove, to deliver energy to one or more portions of an energy delivery zone and to treat one or more portions of target tissue.

Expandable reservoir 140 has been positioned in a distal portion of duodenal tissue, such as a section that includes a previously expanded segment of submucosal tissue (submucosal tissue expansion not shown). Expandable reservoir 140 has been radially expanded such as to contact the mucosal surface of the duodenum at a discrete tissue segment of target tissue, tissue segment TS1 as shown. Tissue segment TS1 is located distal to a series of sequential tissue segments of target tissue, tissue segments TS2 through TS6 as shown. Expandable reservoir 140 and fixed amount of ablative fluid 335 are shown in FIG. 3 positioned to ablate or otherwise treat tissue segment TS1. As described above, each of tissue segments TS1 through TS6 has a corresponding energy delivery zone (not shown) to which energy is delivered from expandable reservoir 140 to cause the appropriate treatment of target tissue.

Expandable reservoir 140 can be sized to allow positioning in curved segments of the GI tract with a minimum radius of curvature, such as a curved segment of the duodenum and/or jejunum with an average radius of curvature less than 5 cm over a 75° arc, or less than 3 cm over a 75° arc. In these curved segments (and straighter segments as well), expandable reservoir 140 can be expanded without exerting undesired force onto tissue (e.g. expanded to contact the tissue wall). In some embodiments, expandable reservoir 140 is constructed and arranged to treat curved segments of the GI tract and comprises a length less than or equal to 30 mm, such as less than or equal to 25 mm, less than or equal to 20 mm, less than or equal to 15 mm. After treatment of tissue segment TS1, expandable reservoir 140 can be repositioned to tissue segment TS2, just proximal to tissue segment TS1, with or without contracting expandable reservoir 140 prior to the repositioning. Subsequently, a second tissue treatment (e.g. a second energy delivery) can be performed. The steps of repositioning and treating portions of target tissue are repeated until tissue segments TS3, TS4, TS5, and TS6 have been treated. In a single clinical procedure, the combined length of target tissue segments TS1 through TS6 can represent between 25% and 100% of the length of the duodenal mucosa length, such as when between 2 and 50 axial segments of tissue receive between 2 and 50 energy deliveries from expandable reservoir 140 (e.g. 2 to 50 different fixed amounts of ablative fluid 335). In some embodiments, each of tissue segments TS1 through TS6 have a maximum axial duodenal length of less than 20 cm, less than 15 cm, less than 10 cm, less than 5 cm or less than 3 cm. In some embodiments, the cumulative axial length of duodenal tissue segments treated, (e.g. at least tissue segments TS1 through TS6) is less than 100 cm, or less than 50 cm. Alternatively or additionally, other tissue can be treated, such as has been described hereabove.

Target tissue segments TS1 through TS6 typically include common or overlapping tissue segments, such as is shown in FIG. 3. While the embodiment of FIG. 3 shows six target tissue segments being treated, more or fewer segments can be treated, such as a procedure in which two or three segments are treated, each segment between approximately 2 cm and 3 cm in length. Tissue treatments can be performed in a contiguous manner (e.g. 1st portion followed by 2nd portion, followed by 3rd portion, etc); however any order can be performed. In some embodiments, multiple contiguous or discontiguous tissue segments are treated simultaneously. In some embodiments, contiguous tissue segments are treated by device 100 continuously, as expandable reservoir 140 is relatively continuously translated proximally and/or distally, such as via a manual or automated retraction and/or advancement, respectively, as is described in reference to FIG. 12 herebelow. In some embodiments, treatment of target tissue is performed as expandable reservoir 140 translates at a rate of at least 10 cm per minute. In some embodiments, a segment of non-treated GI tissue is positioned between two segments of treated GI tissue, such as a non-treated segment of GI tissue in a sharp bend.

Figure 4:
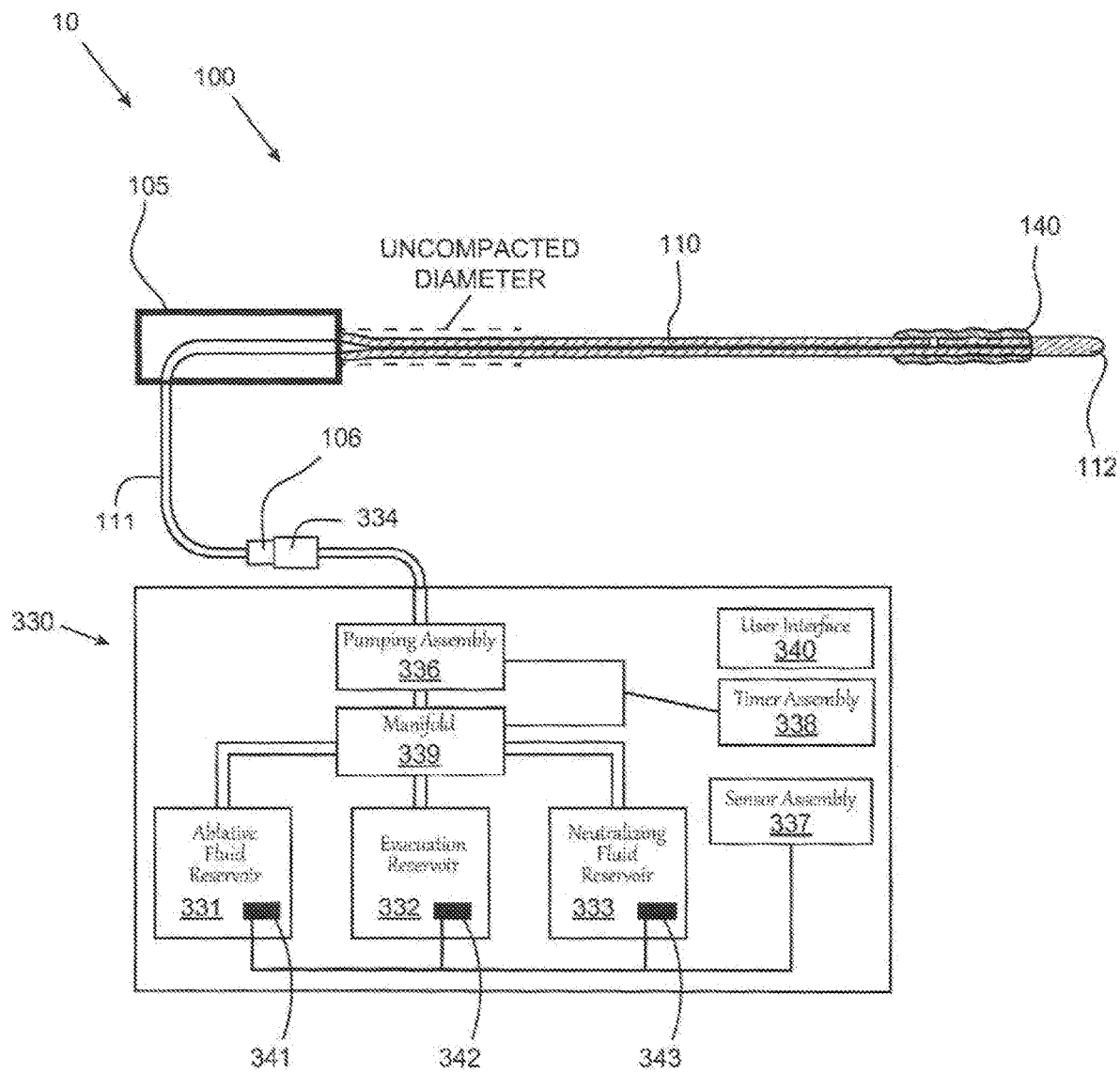
FIG. 4 is a schematic view of a tissue treatment system including a treatment device comprising a radially compactable shaft, consistent with the present inventive concepts.

Referring now to FIG. 4, a schematic view of a tissue treatment system including a treatment device comprising a radially compactable shaft is illustrated, consistent with the present inventive concepts. System 10 includes treatment device 100. Device 100 is shown in a side sectional view. Treatment device includes handle 105 and attachment port 106, which can be configured as described in reference to the similar components of FIG. 1 hereabove. System 10 includes EDU 330, which can be configured similar to EDU 330 of FIG. 1, and can include similar components, such as those shown in FIG. 4. A treatment element, expandable reservoir 140 is attached to the distal portion of shaft 110, and is fluidly connected to attachment port 106 via lumen 111. Expandable reservoir 140 is shown in its radially compacted condition. Shaft 110 includes a tip portion 112 distal to expandable reservoir 140, which can include a rapid exchange guidewire lumen, not shown but such as lumen 113 described in reference to FIG. 1 hereabove.

The portion of shaft 110 proximal to expandable reservoir 140 can be constructed and arranged to radially compact under negative pressure, such as in the radially compacted state as shown in FIG. 4. In some embodiments, pumping assembly 336 of EDU 330 is used to apply the negative pressure to lumen 111 of shaft 110 to cause shaft 110 and lumen 111 to radially compact, such as to reduce the volume of lumen 111 as shown. The diameter of the proximal radially compacted portion of shaft 110 can be configured to relatively match the diameter of tip portion 112, such that shaft 110 can be advanced through a smaller diameter working channel (e.g. of an endoscope) than shaft 110 could be advanced through if not in a radially compacted state. In some embodiments, tip portion 112 and the radially compacted portion of shaft 110 comprise a diameter less than 8 mm, less than 6 mm, or less than 4 mm.

Figure 5:
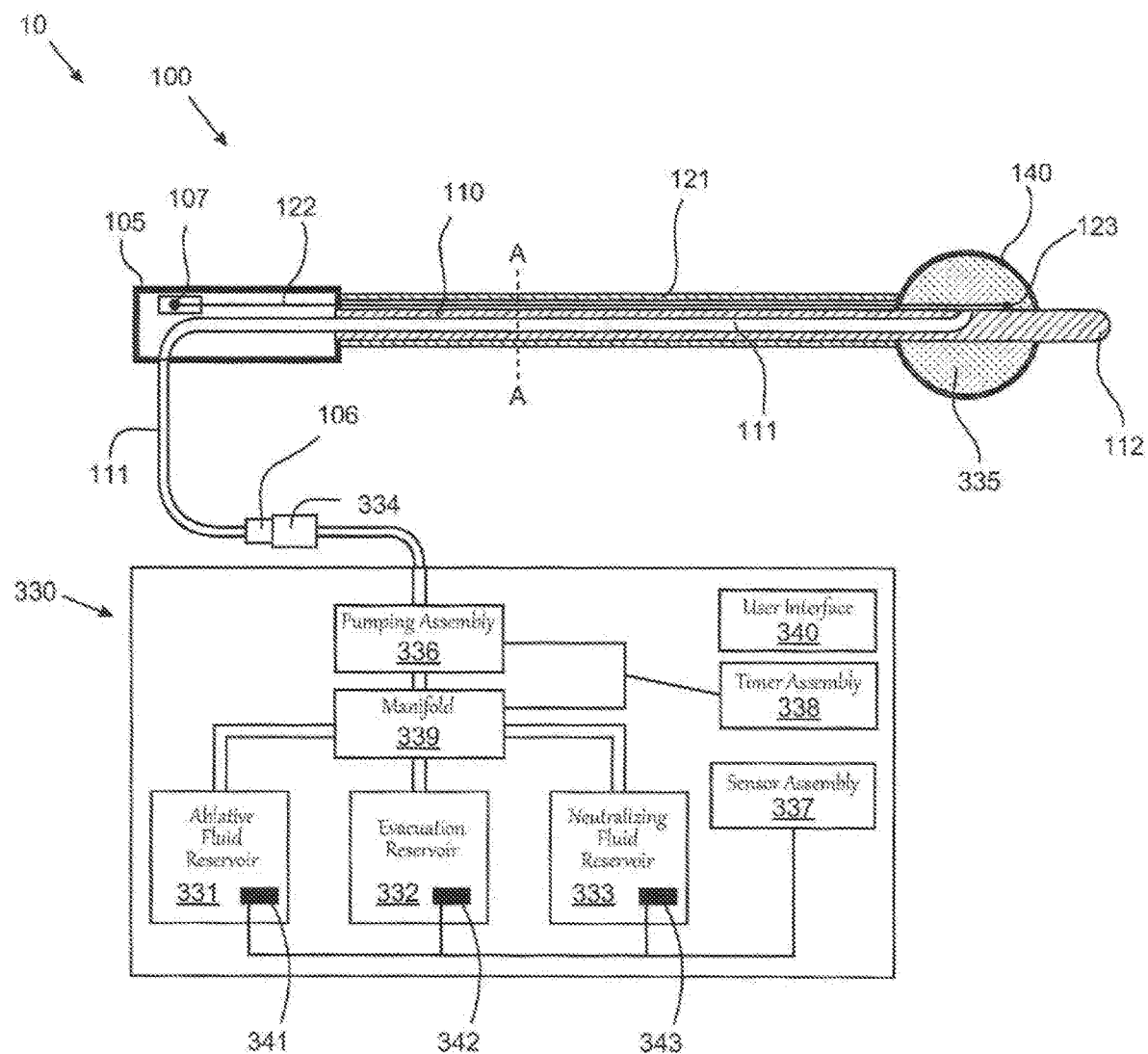
FIG. 5 is a schematic view of a tissue treatment system including a treatment device comprising a manipulatable expandable reservoir.

Referring now to FIG. 5, a schematic view of a tissue treatment system including a treatment device comprising a manipulatable expandable reservoir is illustrated, consistent with the present inventive concepts. System 10 includes treatment device 100. Device 100 is shown in a side sectional view. Treatment device 100 includes handle 105 and attachment port 106, which can be configured as described in reference to the similar components of FIG. 1 hereabove. System 10 includes EDU 330, which can be configured similar to EDU 300 of FIG. 1, and can include similar components, such as those shown in FIG. 5. A treatment element, expandable reservoir 140 is attached to the distal portion of shaft 110, and is fluidly connected to attachment port 106 via lumen 111. Expandable reservoir 140 is shown in its expanded condition, filled with fixed amount of ablative fluid 335. Shaft 110 includes a tip portion 112 distal to expandable reservoir 140, which can include a rapid exchange guidewire lumen, not shown but such as lumen 113 described in reference to FIG. 1 hereabove.

Treatment device 100 further includes an outer shaft 121 with an outer surface and surrounding the portion of shaft 110 proximal to expandable reservoir 140. In some embodiments, shaft 110 is constructed and arranged to be translatable within outer shaft 121. Passing between outer shaft 121 and shaft 110 is control wire 122. The distal end of control wire 122 is fixedly attached to expandable reservoir 140 at anchor 123, typically a glue or other mechanical fixation element. The proximal end of control wire 122 is operably connected to control 107 of handle 105, control 107 typically a control knob including a cam or other mechanism configured to allow an operator to cause control wire 122 to translate in forward and reverse directions. Translation of control wire 122 can be used to manipulate expandable reservoir 140, such as to cause expandable reservoir 140 to change shape and/or to exert force on fluid contained within expandable reservoir 140 (e.g. a fluid comprising a liquid and/or a gas). Manipulation of expandable reservoir 140 can be performed to cause fluid mixing within expandable reservoir 140, such as to create a uniform temperature profile of the fluid within expandable reservoir 140, such as the fixed amount of ablative fluid 335.

Figure 5A:
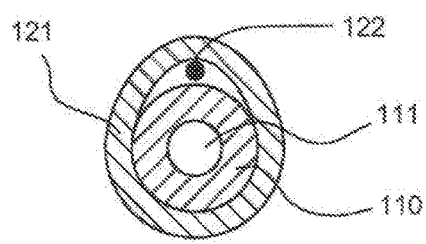
FIG. 5a is a cross sectional view of the shaft portion of the treatment device of FIG. 5, consistent with the present inventive concepts.

Referring additionally to FIG. 5A, a sectional view of the shafts 110 and 121 of FIG. 5 at line A-A are illustrated, consistent with the present inventive concepts. Control wire 122 is shown, slidingly positioned between shaft 110 and outer shaft 121. Lumen 111, residing within shaft 110, is configured to support both delivery and removal of ablative fluid and/or other fluids, to and from expandable reservoir 140.

In some embodiments, outer shaft 121 is configured to add pushability and/or trackability to device 100, such as by providing column and/or torsional strength to device 100. Alternatively or additionally, outer shaft 121 may be configured as an insulator, such as an insulator configured to reduce transfer of energy to or from shaft 110 and/or fluid within lumen 111 to tissue proximate outer shaft 121 (e.g. to prevent adversely modifying tissue at a location remote from expandable reservoir 140 due to energy transfer to or from cold or hot fluid within lumen 111).

Figure 6:
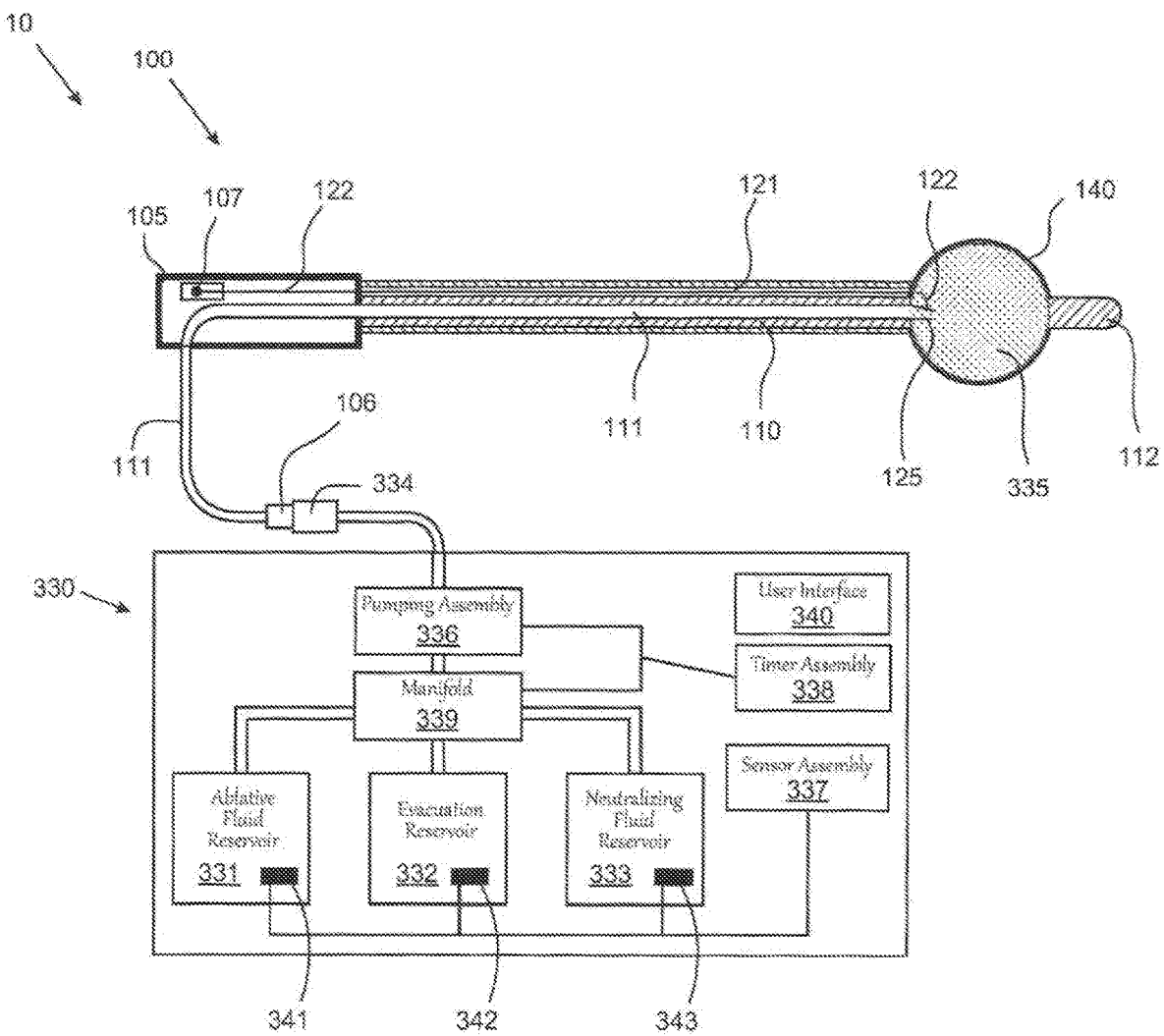
FIG. 6 is a schematic view of a tissue treatment system including a treatment device comprising a valved fluid delivery passage, consistent with the present inventive concepts.

Referring now to FIG. 6, a schematic view of a tissue treatment system including a treatment device comprising a valved fluid delivery passage is illustrated, consistent with the present inventive concepts. System 10 includes treatment device 100. Device 100 is shown in a side sectional view. Treatment device includes handle 105 and attachment port 106, which can be configured as described in reference to the similar components of FIG. 1 hereabove. System 10 includes EDU 330, which can be configured similar to EDU 300 of FIG. 1, and can include similar components, such as those shown in FIG. 6. A treatment element, expandable reservoir 140 is attached to the distal portion of shaft 110, and is fluidly connected to attachment port 106 via lumen 111. Expandable reservoir 140 is shown in its expanded condition, filled with fixed amount of ablative fluid 335. Shaft 110 includes a tip portion 112 distal to expandable reservoir 140, which can include a rapid exchange guidewire lumen, not shown but such as lumen 113 described in reference to FIG. 1 hereabove.

Treatment device 100 further includes valve 125, comprising one or more valves positioned at one or more locations along lumen 111, such as at the distal end of lumen 111 as shown in FIG. 6. Valve 125 can comprise one or more valves selected from the group consisting of: duck bill valve; slit valve; pressure controlled valve; electronically actuated valve; and combinations of these. In some embodiments, valve 125 comprises two or more valves, such as a first valve configured to regulate flow in a first direction, and a second valve configured to regulate flow in a second, opposite direction. Valve 125 is configured to cause flow from lumen 111 into expandable reservoir 140 (e.g. to fill expandable reservoir 140) when the pressure differential between lumen 111 and expandable reservoir 140 is above a threshold and/or to cause flow from expandable reservoir 140 into lumen 111 (e.g. to evacuate expandable reservoir 140) when the pressure differential between lumen 111 and expandable reservoir 140 is below a threshold.

In some embodiments, treatment device 100 further includes an outer shaft 121 with an outer surface and surrounding the portion of shaft 110 proximal to expandable reservoir 140. Passing between outer shaft 121 and shaft 110 is a wire or other translatable control rod, control wire 122. The distal end of control wire 122 is fixedly attached to valve 125. The proximal end of control wire 122 is operably connected to control 107 of handle 105. In some embodiments, control 107 comprises a control knob including a cam or other mechanism configured to allow an operator to cause control wire 122 to advance and/or retract (i.e. translate) to apply a force to control valve 125 (e.g. translate to open, close or otherwise modify an orifice of valve 125). Alternatively or additionally, control 107 can comprise an electronic switch used to transfer power through wire 122 (e.g. one or more electrically conductive conduits) to electrically control valve 125.

Figures 6A, 6B:
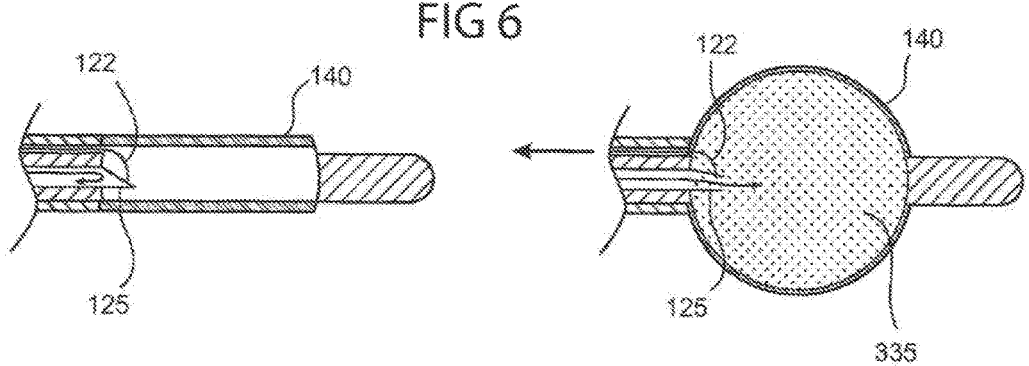
FIG. 6A is a side sectional view of the distal portion of the treatment device of FIG. 6, with a valve in a closed position, consistent with the present inventive concepts.
FIG. 6B is a side sectional view of the distal portion of the treatment device of FIG. 6, with a valve in an open position and an expandable reservoir in an expanded condition, consistent with the present inventive concepts.

Referring additionally to FIGS. 6A and 6B, a magnified view of the distal portion of device 100 of FIG. 6 is illustrated, with valve 125 in closed and open positions, respectively. In FIG. 6A, expandable reservoir 140 is shown in an unexpanded condition. Fluid can be introduced to fill lumen 111, without causing significant expansion of expandable reservoir 140, such as to enhance thermal priming of lumen 111 as described hereabove. In FIG. 6B, valve 125 is opened, such as via translation of control wire 122 as shown, and the fixed amount of ablative fluid 335 has been introduced into expandable reservoir 140, causing expandable reservoir 140 to radially expand (e.g. an expansion that causes expandable reservoir 140 to contact target tissue and deliver a pre-determined thermal dose of energy to the target tissue).

In some embodiments, a thermal priming procedure is performed upon device 100 prior to filling expandable reservoir 140 with a fixed amount of ablative fluid 335, such as a thermal priming procedure to warm or chill a portion of shaft 110 proximal to expandable reservoir 140. In some embodiments, a second thermal priming procedure is performed upon device 100, prior to a second filling of expandable reservoir 140 with a second fixed amount of ablative fluid 335. Thermal priming procedures can be performed repeatedly for additional sequential filling of expandable reservoir 140. In some embodiments, a neutralizing step is performed prior to and/or after tissue treatment, in which a neutralizing fluid is delivered to expandable reservoir 140 to cool and/or warm tissue, as has been described hereabove.

Referring now to FIG. 7, a schematic view of a tissue treatment system including a treatment device comprising a shaft with an internal coil is illustrated, consistent with the present inventive concepts. System 10 includes treatment device 100. Device 100 is shown in a side sectional view. Treatment device includes handle 105 and attachment port 106, which can be configured as described in reference to the similar components of FIG. 1 hereabove. System 10 includes EDU 330, which can be configured similar to EDU 300 of FIG. 1, and can include similar components, such as those shown in FIG. 7. A treatment element, expandable reservoir 140 is attached to the distal portion of shaft 110, and is fluidly connected to attachment port 106 via lumen 111. Expandable reservoir 140 is shown in its expanded condition, filled with fixed amount of ablative fluid 335. Shaft 110 includes a tip portion 112 distal to expandable reservoir 140, which can include a rapid exchange guidewire lumen, such as lumen 113 described in reference to FIG. 1 hereabove.

A reinforcing coil, coil 116 can be positioned on, in (i.e. in the wall of) and/or within shaft 110. Coil 116 can comprise a metal coil such as a stainless steel or nickel titanium alloy coil, or a non-metallic coil such as a coil made of one or more polymer materials. Coil 116 can be configured to prevent or resist the radial compacting of lumen 111, such as when a negative pressure is applied to lumen 111 (e.g. during a fluid evacuation procedure).

Figure 7A:
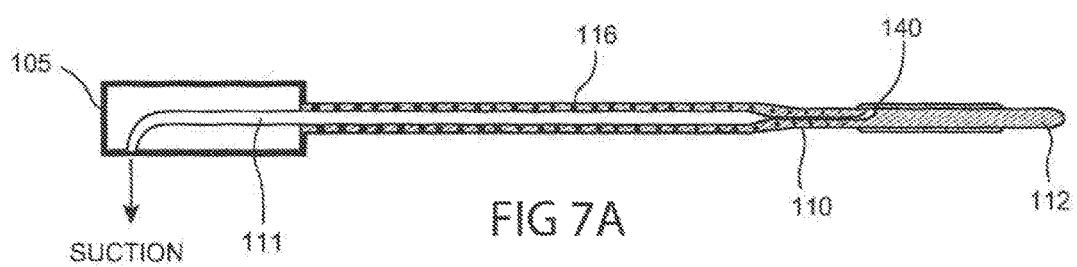
FIG. 7A is a side sectional view of the treatment device of FIG. 7 with a shaft in a partially compacted condition, consistent with the present inventive concepts.
Figure 7B:
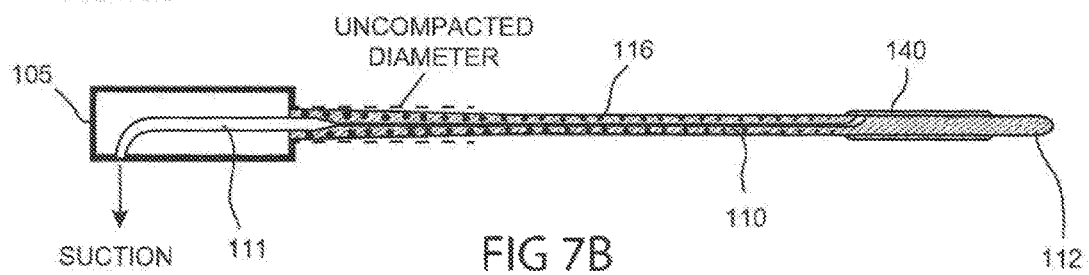
FIG. 7B is a side sectional view of the treatment device of FIG. 7 with a shaft in a more fully compacted condition, consistent with the present inventive concepts.

In some embodiments, a proximal portion of coil 116 can comprise a greater radial strength than a distal portion of coil 116, such as when the coil filament diameter is greater proximally than distally. In these embodiments, shaft 110 may be configured to radially compact distally prior to any significant radial compacting occurring proximally. In some embodiments, coil 116 is constructed and arranged to allow a continuous radial compacting of shaft 110 (e.g. when a negative pressure is applied to lumen 111) starting at a distal portion of shaft 110 and traveling proximally in a continuous manner. In this configuration, fluid is propelled (i.e. during the radial compacting of shaft 110) from the distal portion of shaft 110 to the proximal portion of shaft 110 avoiding fluid being trapped in a distal location. Referring additionally to FIGS. 7A and 7B, two sequential steps of radially compacting of shaft 110 are shown. In FIG. 7A, suction is applied to lumen 111 (e.g. causing a negative pressure within lumen 111), such as has been described hereabove. Expandable reservoir 140 is in a radially compacted state, and the distal portion of shaft 110 is radially compacted. In FIG. 7B, the suction has continuously been applied and/or increased, and a more proximal portion of shaft 110 is radially compacted. Application of the negative pressure can be used to evacuate fluids in a distal portion of shaft 110 prior to the evacuation of fluids in a more proximal portion of shaft 110, providing a more complete removal of fluids from shaft 110.

Figure 8:
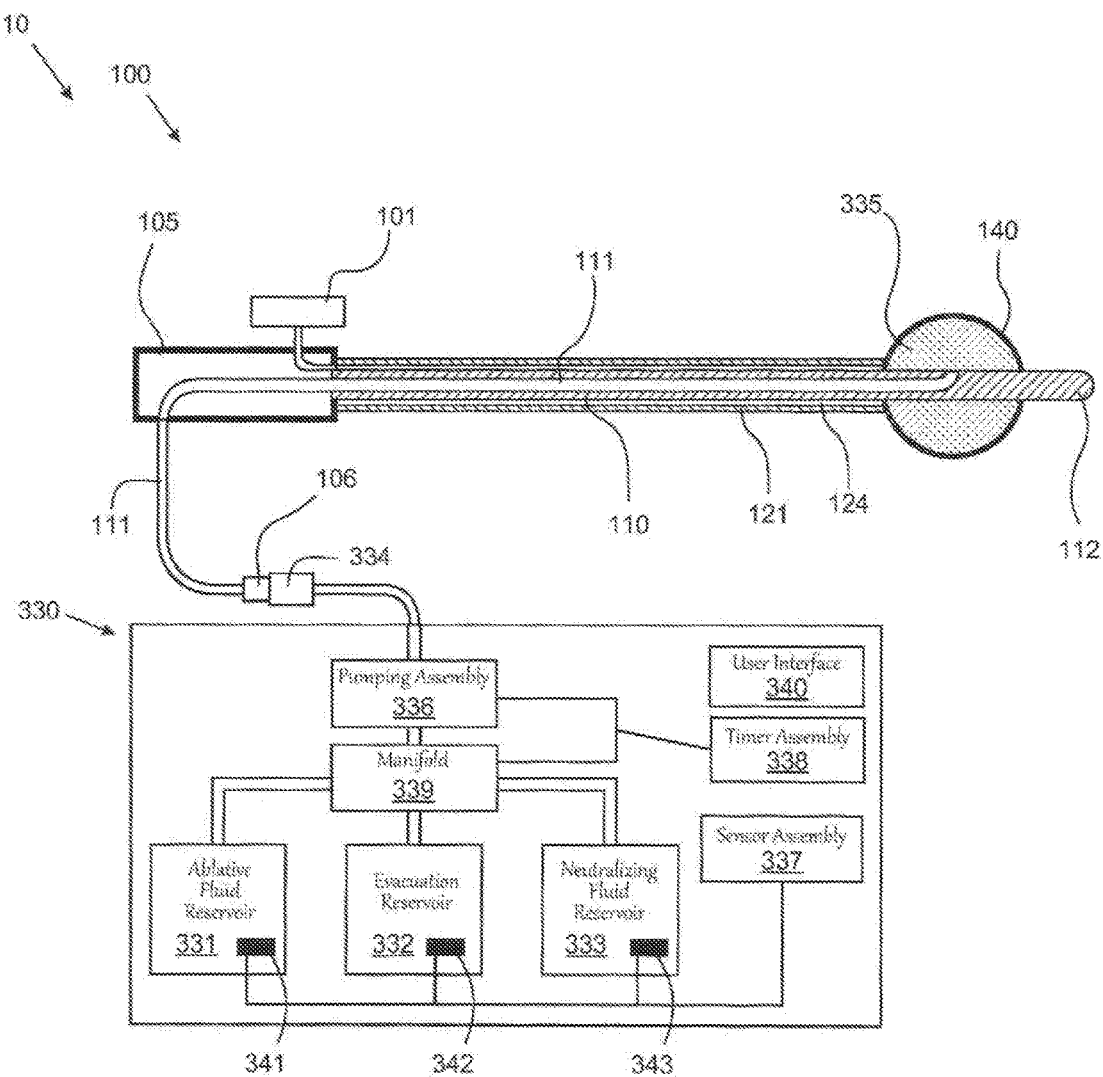
FIG. 8 is a schematic view of a tissue treatment system including a treatment device comprising a radially compactable shaft, consistent with the present inventive concepts.

Referring now to FIG. 8, a schematic view of a tissue treatment system including a treatment device comprising a radially compactable shaft is illustrated, consistent with the present inventive concepts. System 10 includes treatment device 100. Device 100 is shown in a side sectional view. Treatment device includes handle 105 and attachment port 106, which can be configured as described in reference to the similar components of FIG. 1 hereabove. System 10 includes EDU 330, which can be configured similar to EDU 300 of FIG. 1, and can include similar components, such as those shown in FIG. 8. A treatment element, expandable reservoir 140 is attached to the distal portion of shaft 110, and is fluidly connected to attachment port 106 via lumen 111. Expandable reservoir 140 is shown in its expanded condition, filled with fixed amount of ablative fluid 335. Shaft 110 includes a tip portion 112 distal to expandable reservoir 140, which can include a rapid exchange guidewire lumen, not shown but such as lumen 113 described in reference to FIG. 1 hereabove.

Figure 8A:
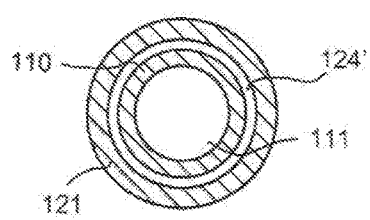
FIG. 8A is a cross sectional view of a shaft portion of one embodiment of the treatment device of FIG. 8, comprising an outer lumen surrounding a full circumferential portion of an inner shaft, consistent with the present inventive concepts.
Figure 8B:
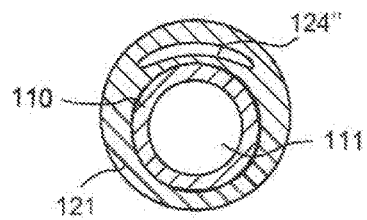
FIG. 8B is a cross sectional view of a shaft portion of another embodiment of the treatment device of FIG. 8, comprising an outer lumen surrounding a partial circumferential portion of an inner shaft, consistent with the present inventive concepts.
Figure 8C:
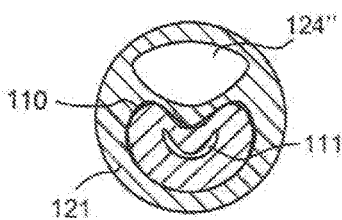
FIG. 8C is a cross sectional view of the shaft portion of FIG. 8B, after the inner shaft has been radially compacted, consistent with the present inventive concepts.

Treatment device 100 further includes an outer shaft 121 with an outer surface and surrounding the portion of shaft 110 proximal to expandable reservoir 140. Passing between outer shaft 121 and shaft 110 is a second fluid passageway of the present inventive concepts, lumen 124. Lumen 124 can be configured to completely surround shaft 110, such a lumen 124' shown in FIG. 8A, such that fluids entering lumen 124 completely surround shaft 110. Alternatively, lumen 124 can be positioned along a partial circumferential portion of shaft 110, such as lumen 124" as shown in FIG. 8B. One or more fluids can be introduced into lumen 124 of device 100, such as one or more warming, cooling and/or force applying fluids introduced into lumen 124. Lumen 124 is attached on its proximal end to pressure source 101, typically a syringe or other fluid delivery source and/or pumping assembly (e.g. configured for fluid delivery and/or extraction). In some embodiments, EDU 330 comprises pressure source 101, such as when pumping assembly 336 is configured to deliver one or more fluids into lumen 124. In some embodiments, the distal end of lumen 124 is sealed, such as at a location proximate but proximal to expandable reservoir 140. Fluids can be delivered into lumen 124 to warm or chill shaft 110, such as in a thermal priming procedure or to tend shaft 110 towards body temperature. Alternatively or additionally, fluids can be introduced into lumen 124 to act as an insulating layer between shaft 110 and neighboring tissue or a separate device. Alternatively or additionally, delivery of fluids into lumen 124 can be used to radially compact shaft 110 (e.g. shaft 110 comprises a compliant tube), such as to purge air or other fluids from lumen 111 of shaft 110 by applying a "squeezing" force to shaft 110 and lumen 111. Referring now to FIG. 8C, lumen 124" of FIG. 8C has been pressurized to radially compact shaft 110 and lumen 111, such as to perform a fluid evacuation procedure on lumen 111 as has been described hereabove.

In some embodiments, one or more valves are present within lumens 111, 124, 124' and/or 124", such as valve 125 described in reference to FIG. 6 hereabove.

Figure 9:
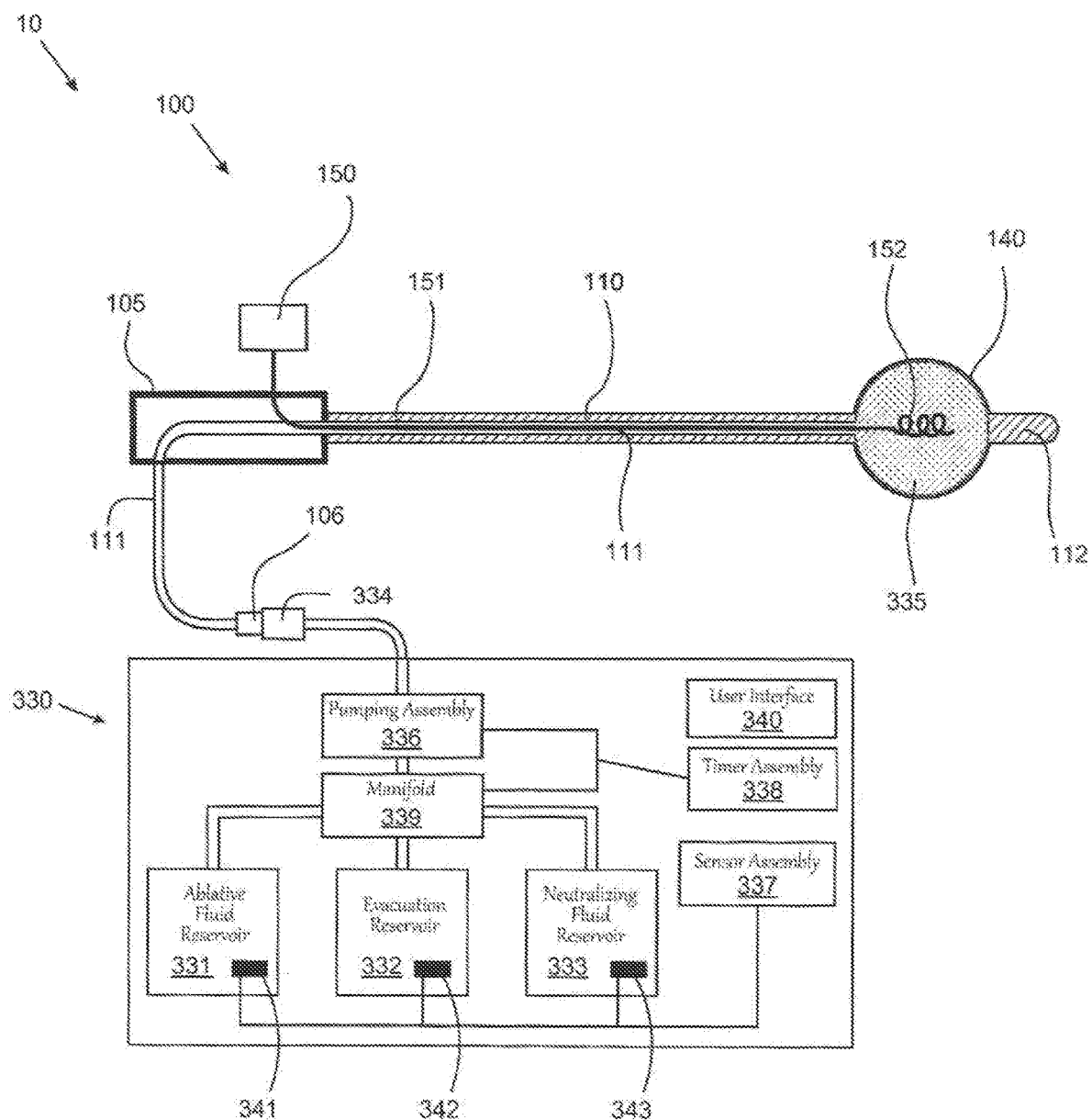
FIG. 9 is a schematic view of a tissue treatment system including a treatment device comprising an internal heating element, consistent with the present inventive concepts.

Referring now to FIG. 9, a schematic view of a tissue treatment system including a treatment device comprising an internal heating element is illustrated, consistent with the present inventive concepts. System 10 includes treatment device 100. Device 100 is shown in a side sectional view. Treatment device includes handle 105 and attachment port 106, which can be configured as described in reference to the similar components of FIG. 1 hereabove. System 10 includes EDU 330, which can be configured similar to EDU 300 of FIG. 1, and can include similar components, such as those shown in FIG. 9. A treatment element, expandable reservoir 140 is attached to the distal portion of shaft 110, and is fluidly connected to attachment port 106 via lumen 111. Expandable reservoir 140 is shown in its expanded condition, filled with fixed amount of ablative fluid 335. Shaft 110 includes a tip portion 112 distal to expandable reservoir 140, which can include a rapid exchange guidewire lumen, not shown but such as lumen 113 described in reference to FIG. 1 hereabove.

Device 100 of FIG. 9 includes one or more heating elements such as a heating wire, wire 151 and/or heating coil, coil 152. Wire 151 and/or heating coil 152 can each comprise a linear heating element and/or a coiled heating element. A heating assembly provides electrical energy to the heating elements, such as to provide local heating within device 100. Wire 151 is attached to a heating assembly 150, and heating coil 152 is attached to heating assembly 150 via wire 151. In some embodiments, EDU 330 comprises heating assembly 150. Coil 152 is positioned within expandable reservoir 140 such that system 10 can selectively heat fluid within expandable reservoir 140, such as fixed amount of ablative fluid 335. Wire 151 can also be configured as a heating element, such as a resistive heating element that generates heat energy as electrical current passes through wire 151. Wire 151 can be positioned to heat fluid within lumen 111 and/or heat shaft 110. Heating provided by wire 151 and/or coil 152 can be used to perform a thermal priming procedure or to bring expandable reservoir 140 and/or shaft 110 toward body temperature (e.g. when device 100 is configured as a cryogenic ablation device). Alternatively, wire 151 and/or coil 152 can be configured to provide a cooling function, such as when wire 151 and/or coil 152 comprise a peltier or other cooling component which removes heat when powered by electrical current.

In some embodiments, wire 151 and/or coil 152 are constructed and arranged to generate heat when exposed to electromagnetic energy such as electromagnetic energy selected from the group consisting of: microwave energy; laser energy such as 2 micron CW laser energy; and combinations of these. In some embodiments, wire 151 and/or coil 152 comprise an ultrasonic receiver constructed and arranged to produce heat when exposed to sound energy, such as sound energy provided by EDU 330.

Figure 10:
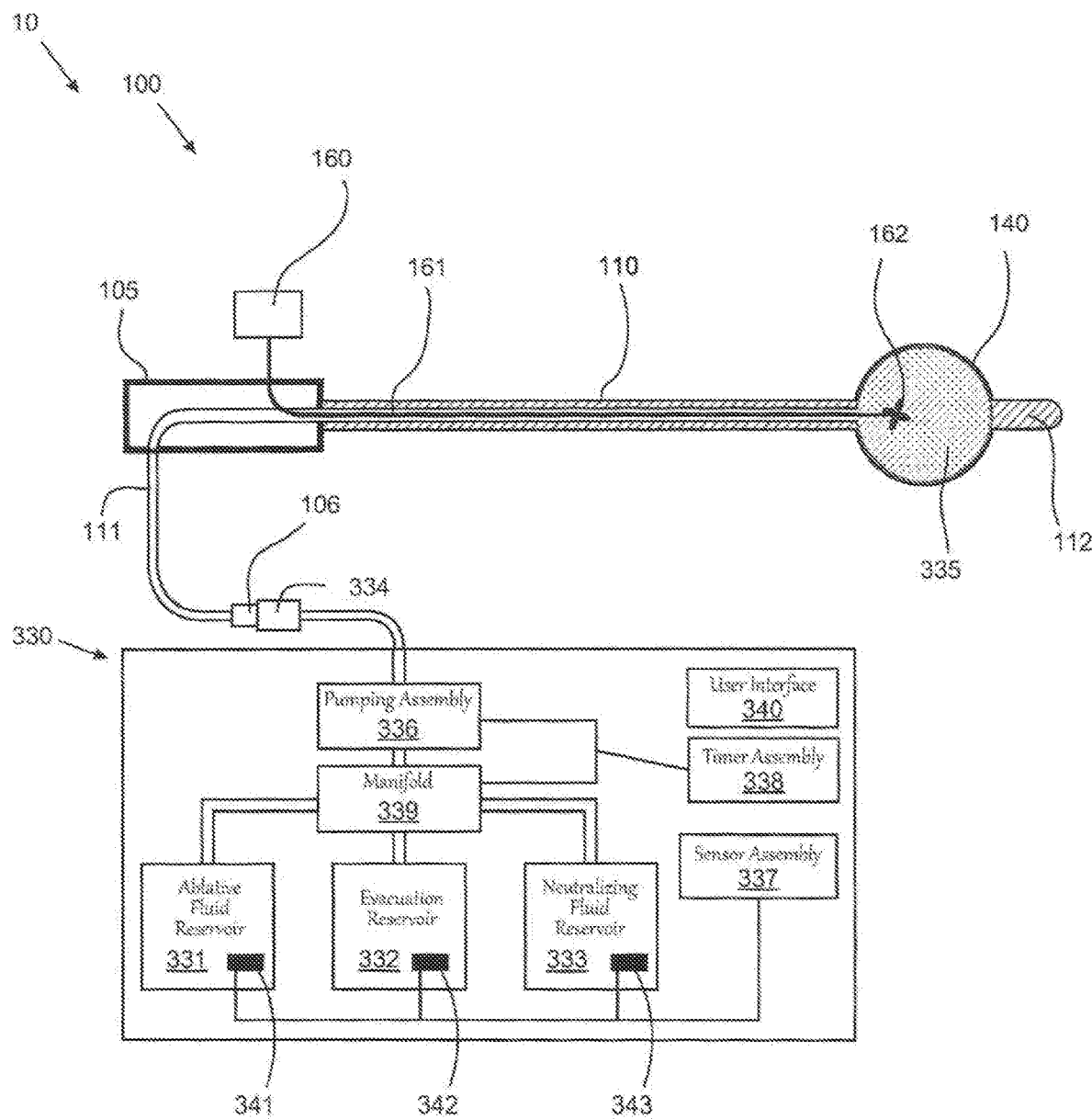
FIG. 10 is a schematic view of a tissue treatment system including a treatment device comprising an internal fluid mixing element, consistent with the present inventive concepts.

Referring now to FIG. 10, a schematic view of a tissue treatment system including a treatment device comprising an internal fluid mixing element is illustrated, consistent with the present inventive concepts. System 10 includes treatment device 100. Device 100 is shown in a side sectional view. Treatment device includes handle 105 and attachment port 106, which can be configured as described in reference to the similar components of FIG. 1 hereabove. System 10 includes EDU 330, which can be configured similar to EDU 300 of FIG. 1, and can include similar components, such as those shown in FIG. 10. A treatment element, expandable reservoir 140 is attached to the distal portion of shaft 110, and is fluidly connected to attachment port 106 via lumen 111. Expandable reservoir 140 is shown in its expanded condition, filled with fixed amount of ablative fluid 335. Shaft 110 includes a tip portion 112 distal to expandable reservoir 140, which can include a rapid exchange guidewire lumen, not shown but such as lumen 113 described in reference to FIG. 1 hereabove.

Device 100 of FIG. 10 includes one or more fluid mixing elements 162, such as a propeller, blade, stirring rod, rotary stirring rod, and/or other configuration which mixes fluid within expandable reservoir 140 when rotated. Mixing element 162 is operably attached to drive shaft 161, which in turn is operably attached to fluid mixing assembly 160 as shown. In some embodiments, EDU 330 comprises fluid mixing assembly 160. Fluid mixing assembly 160 is constructed and arranged to rotate drive shaft 161 at a fixed or variable rotational velocity, such as to cause constant, intermittent and/or variable mixing of fluid within expandable reservoir 140, such as to cause the majority of fluid in expandable reservoir 140 to tend to be at a similar temperature and/or to create uniform heating of target tissue by expandable reservoir 140. Fluid mixing element 162 can comprise a rod with a distally mounted agitator. Mixing element 162 can be configured to be advanced and/or retracted, such as to enhance mixing of fluid within expandable reservoir 140. EDU 330 can perform a fluid mixing function, such as by providing one or more fluids to expandable reservoir 140 in a pulsed manner, such as to agitate fluid within expandable reservoir 140. Alternatively or additionally, EDU 330 can be constructed and arranged to provide ultrasound waves to an ultrasound transducer-based mixing element 162 positioned in lumen 111 and/or expandable reservoir 140.

Figure 11:
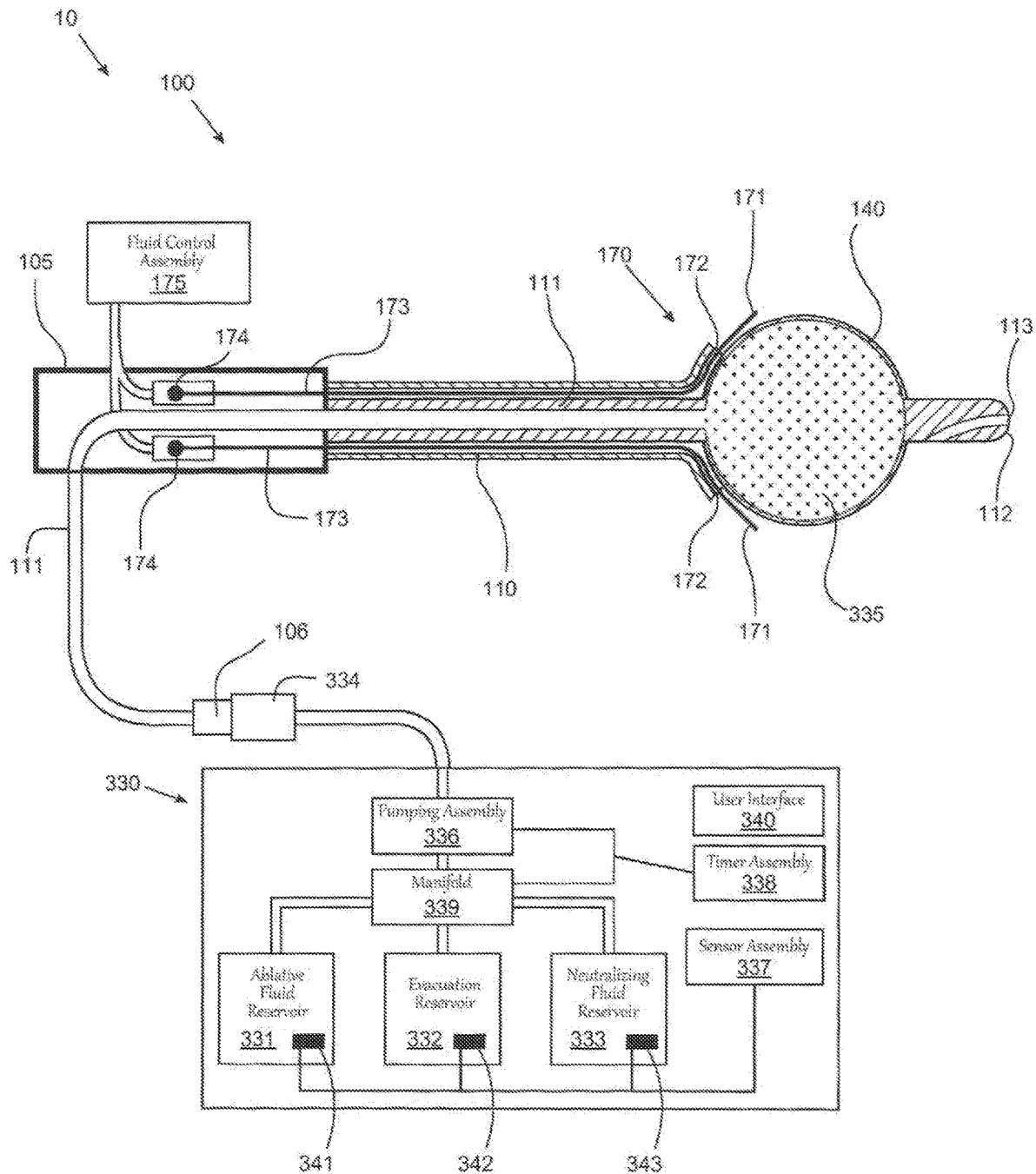
FIG. 11 is a schematic view of a tissue treatment system including a treatment device comprising a tissue expansion assembly, consistent with the present inventive concepts.

Referring now to FIG. 11, a schematic view of a tissue treatment system including a treatment device comprising a tissue expansion assembly is illustrated, consistent with the present inventive concepts. System 10 includes treatment device 100. Device 100 is shown in a side sectional view. Treatment device includes handle 105 and attachment port 106, which can be configured as described in reference to the similar components of FIG. 1 hereabove. System 10 includes EDU 330, which can be configured similar to EDU 300 of FIG. 1, and can include similar components, such as those shown in FIG. 10. A treatment element, expandable reservoir 140 is attached to the distal portion of shaft 110, and is fluidly connected to attachment port 106 via lumen 111. Expandable reservoir 140 is shown in its expanded condition, filled with fixed amount of ablative fluid 335. Shaft 110 includes a tip portion 112 distal to expandable reservoir 140, which can include a rapid exchange guidewire lumen, such as lumen 113 described in reference to FIG. 1 hereabove.

Device 100 of FIG. 10 further comprises a tissue expansion assembly 170 including one or more fluid delivery elements 171 advanceable from one or more surrounding ports 172, which can be mounted to a proximal portion of expandable reservoir 140 as shown. In some embodiments, tissue expansion assembly 170 is constructed and arranged as described in applicant's co-pending application International Patent Application Serial Number PCT/US2013/ 37485, entitled "Tissue Expansion Devices, System and Methods", filed Apr. 19, 2013, the contents of which is incorporated by reference in its entirety. In some embodiments, tissue expansion assembly 170 is constructed and arranged similar to expandable assembly 130 of FIG. 12 described herebelow.

Tissue expansion assembly 170 can comprise multiple fluid delivery elements 171 such as two, three or four fluid delivery elements 171 positioned with equal spacing (e.g. 180°, 120° or 90° spacing respectively) about a full circumference of expandable reservoir 140. Fluid delivery elements 171 can comprise a fluid delivery element selected from the group consisting of: a needle; a water jet; an iontophoretic element; and combinations thereof. Fluid delivery elements 171 are each fluidly attached to a separate fluid delivery passage, tubes 173. Each tube 173 is attached to control knob 174 which is configured to allow an operator to advance and retract each corresponding tube 173 and its attached fluid delivery element 171 (the two fluid delivery elements 171 of FIG. 11 are in the advanced position). In alternative embodiments, each fluid delivery element 171 is attached to a single fluid delivery passage (e.g. via a manifold not shown).

Each tube 173 can include a lumen to provide fluid to the attached fluid delivery element 171, and can also include a separate lumen configured to apply a vacuum or other negative pressure to port 172, such as to draw tissue toward port 172 when expandable reservoir 140 is in a radially compacted state and the associated fluid delivery element 171 is in a retracted state. Each tube 173 is fluidly attached to fluid control assembly 175, such that tissue expanding fluid can be delivered into submucosal or other tissue via tube 173 and its associated fluid delivery element 171. In some embodiments, fluid delivery element 171 comprises a needle such that advancement of each element 171 causes the needle to penetrate the tissue in proximity to each port 172, and subsequent injection of fluid through element 171 causes expansion of one or more layers of tissue proximate the penetration site. Treatment device 100 of FIG. 11 is configured to perform both target tissue treatment as well as tissue expansion. In some embodiments, expansions of one or more layers of tissue of multiple axial tissue segments are performed sequentially, followed by ablation of target tissue of similar multiple axial tissue segments (e.g. while insuring that only segments with expanded tissue are treated). In other embodiments, expansion of one or more layers of tissue of a single axial tissue segment is followed by ablation of target tissue of approximately that same axial tissue segment, after which one or more additional axial segments can have similarly sequenced tissue expansions and target tissue ablations performed.

Referring now to FIG. 12, a schematic view of a system for ablating or otherwise treating target tissue is illustrated, consistent with the present inventive concepts. System 10 is configured to treat target tissue TT, such as to treat one or more patient diseases or disorders selected from the group consisting of: diabetes; obesity or otherwise being overweight; hypercholesterolemia; exercise intolerance; psoriasis; and combinations of these. In the embodiment of FIG. 12, target tissue TT includes one or more tissue segments within a body lumen of a mammalian patient as has been described hereabove. In some embodiments, target tissue TT comprises a continuous or discontinuous circumferential segment of a duodenum, such as a volume of tissue comprising at least 50% of the duodenal mucosa, or at least 67% of the duodenal mucosa. In some embodiments, target tissue TT comprises a treatment portion comprising duodenal mucosal tissue and a safety-margin portion comprising at least an innermost layer of the duodenal submucosa. System 10 can be configured to treat the duodenal mucosa while avoiding damage to duodenal adventitial tissue, such as by avoiding damage to tissue beyond the mucosa, to tissue beyond the superficial submucosa and/or to tissue beyond the deep submucosa. System 10 can be constructed and arranged to deliver one or more fixed amount of ablative fluid to deliver one or thermal doses of energy to one or more portions of target tissue, such as fixed amount of ablative fluid 335 as described in reference to FIG. 1 hereabove.

System 10 can include one or more tissue treatment devices, such as first treatment device 100 and second treatment device 100' (collectively or singly, device 100). First treatment device 100 can be used in a first clinical procedure including treatment of target tissue, and second treatment device 100' can be used in a second clinical procedure including treatment of target tissue, as is described hereabove. In some embodiments, the second clinical procedure is performed at least twenty-four hours after the first clinical procedure. Target tissue treatments performed in the second clinical procedure can be constructed and arranged based on one or more outcomes of the first clinical procedure, also as is described hereabove. Additional treatment devices can be included, such as to perform a third or other subsequent clinical procedures including target tissue treatments.

First treatment device 100 and second treatment device 100' can be similar or dissimilar treatment devices, and can be constructed and arranged to perform similar or dissimilar treatments to similar or dissimilar volumes of tissue. Differences between first treatment device 100 and second treatment device 100' can include but are not limited to: type of ablative treatment provided such as type of energy delivered; type of non-ablative treatment provided; configuration of a treatment assembly or a treatment element included such as configuration of a treatment assembly or a treatment element included in the treatment device; length of the device; diameter of a portion of the device; and combinations of these. In some embodiments, first treatment device 100 comprises a first treatment element constructed and arranged to deliver a different form of energy than a second treatment element of second treatment device 100'. Alternatively or additionally, first treatment device 100 can comprise a first treatment element with a different geometry (e.g. different diameter, length and/or tissue contact surface area or shape), than a second treatment element of second treatment device 100'.

In some embodiments, system 10 can be constructed and arranged as is described in applicant's co-pending U.S. patent application Ser. No. 13/945,138, entitled "Devices and Methods for the Treatment of Tissue", filed Jul. 18, 2013, the contents of which is incorporated by reference in its entirety. In some embodiments, first treatment device 100 and/or second treatment device 100' can be constructed and arranged to ablate tissue, such as with an ablation treatment selected from the group consisting of: delivery of thermal energy from a balloon filled with fluid at an ablative temperature; RF energy ablation such as monopolar and/or bipolar RF energy ablation; delivery of an ablative fluid directly to tissue; cryogenic ablation; delivery of laser energy; delivery of sound energy such as subsonic sound energy or ultrasonic sound energy; plasma energy delivery; argon plasma coagulation; microwave energy delivery; delivery of non-laser light energy; and combinations of these. In some embodiments, first treatment device 100 and/or second treatment device 100' can be constructed and arranged to perform a non-ablative treatment of target tissue, such as with a non-ablative treatment selected from the group consisting of: mechanical removal of mucosal tissue; chemical, sclerosant or pharmaceutical injection into the submucosa; radioactive seed deposition; chemical spray such as an acid spray; pharmacologic administration such as drug delivery via an agent-eluting balloon; and combinations of these. First treatment device 100 and/or second treatment device 100' can be configured to resect tissue, such as to resect tissue selected from the group consisting of: plicae tissue; mucosal tissue; submucosal tissue; and combinations of these.

System 10 can include one or more body introduction devices, such as endoscope 350. Endoscope 350 can comprise a standard GI endoscope such as an endoscope with one or more working channels configured to slidingly receive first treatment device 100 (as shown) and/or second treatment device 100'.

System 10 can include energy delivery unit (EDU) 330, which can be operably attached to first treatment device 100 (as shown) and/or second treatment device 100'. EDU 330 can be configured to provide numerous forms of energy to one or more treatment elements of first treatment device 100 and/or second treatment device 100', such as an energy form selected from the group consisting of: RF energy; microwave energy; laser energy; sound energy such as subsonic sound energy or ultrasound energy; chemical energy; thermal energy such as heat energy or cryogenic energy; and combinations of these.

System 10 can include pumping assembly 336 which can provide and/or remove one or more fluids from one or more devices of system 10, such as first treatment device 100, second treatment device 100' and/or endoscope 350. Pumping assembly 336 can include one or more fluid reservoirs, such as fluid reservoir 333 shown, and/or it can receive or supply fluids to EDU 330. In some embodiments, pumping assembly 336 and/or EDU 330 recirculate one or more fluids through a device of system 10, such as to recirculate fluid through first treatment device 100, second treatment device 100' and/or endoscope 350.

System 10 can include motion transfer assembly 320, which can be constructed and arranged to rotate, translate and/or otherwise move one or more devices, assemblies and/or components of system 10, as is described in detail herebelow.

System 10 can include controller 310, comprising one or more algorithms 311, which can be constructed and arranged to automatically and/or manually control and/or monitor one or more devices, assemblies and/or components of system 10, as is described in detail herebelow.

Device 100 comprises a tissue treatment assembly, treatment assembly 140, which can be configured similar to expandable reservoir 140 of FIG. 1. Treatment assembly 140 can include one or more elements constructed and arranged to ablate or otherwise treat target tissue, such as treatment element 145 shown. Treatment element 145 can comprise one or more elements selected from the group consisting of: a bolus of ablative fluid, such as the fixed amount of ablative fluid 335 of FIG. 1; an electrical energy delivery element such as one or more electrodes constructed and arranged to deliver RF energy; a fluid delivery element such as a nozzle or permeable surface constructed and arranged to deliver ablative fluid directly to target tissue TT; a balloon such as a balloon constructed and arranged to receive an ablative fluid and deliver hot or cold thermal energy to ablate target tissue TT; a laser energy delivery element such as an optical fiber, a focusing lens and/or other optical component; a sound energy delivery element such as a piezo-based element configured to deliver ultrasonic and/or subsonic energy; a tissue abrading element; and combinations of these. Treatment element 145 can be positioned on, in, within and/or passing through one or more components of treatment assembly 140, such as a balloon, cage, spline or other component as are described in detail herein. In some embodiments, treatment assembly 140 and treatment element 145 are the same component, such as when treatment assembly 140 comprises a balloon constructed and arranged to receive hot or cold ablative fluid to treat target tissue. Treatment assembly 140 can comprise an energy distribution element, such as one or more optical components configured to rotate, translate and/or otherwise distribute laser or other light energy to target tissue. In some embodiments, treatment assembly 140 and/or treatment element 145 comprise an energy distribution element including a rotating element such a rotating mirror; a rotating prism and/or a rotating diffractive optic. In some embodiments, device 100 comprises one or more fibers that deliver laser or other light energy to a treatment element 145 comprising a balloon filled with light-scattering material.

In some embodiments, first treatment device 100 and/or second treatment device 100' delivers heat or thermal energy to tissue, such as when treatment assembly 140 and/or treatment element 145 comprises a balloon constructed and arranged to be filled with an ablative fluid comprising a hot or cold volume of fluid at a temperature sufficient to ablate tissue when the balloon contacts the tissue. The hot or cold volume of fluid can be provided to treatment assembly 140 and/or treatment element 145 via EDU 330 and/or pumping assembly 336. System 10 can be configured to deliver thermal energy to tissue as is described in applicant's co-pending International Application Serial Number PCT/US2013/28082, entitled "Heat Ablation Systems, Devices and Methods for the Treatment of Tissue", filed Feb. 27, 2013, the contents of which is incorporated herein by reference in its entirety.

In some embodiments, first treatment device 100 and/or second treatment device 100' delivers RF energy to tissue, such as when treatment element 145 comprises one or more electrodes constructed and arranged to receive RF energy provided by EDU 330. In these embodiments, the one or more electrodes can comprise one or more conductive dots positioned on an expandable element such as a balloon. In some embodiments, EDU 330 is configured to deliver RF energy to one or more electrodes of first treatment device 100 and/or second treatment device 100', such as in a monopolar mode through a grounding pad such as ground pad 70 and/or in a bipolar mode between two or more electrodes of first treatment device 100 or second treatment device 100'. System 10 can be configured to deliver RF energy to tissue as is described in applicant's co-pending International PCT Application Serial Number PCT/US2013/052786, entitled "Electrical Energy Ablation Systems, Devices and Methods for the Treatment of Tissue", filed Jul. 30, 2013, the contents of which is incorporated herein by reference in its entirety.

In some embodiments, first treatment device 100 and/or second treatment device 100' delivers ablative fluid directly to tissue, such as when treatment element 145 comprises one or more fluid delivery elements. In these embodiments, treatment element 145 can be constructed and arranged to ablate target tissue TT by delivering ablative fluid provided by EDU 330 and/or pumping assembly 336. Treatment element 145 can include one or more fluid delivery elements selected from the group consisting of: nozzle such as a nozzle configured to deliver a cone or other shaped spray of fluid; opening; hole; slit; permeable membrane; misting element; vaporizer; and combinations of these. Ablative fluid can comprise one or more liquids or gases that are delivered to target tissue TT at a temperature above or below a threshold that would ablate tissue. In some embodiments, the ablative fluid delivered by treatment element 145 comprises steam, such as steam at a temperature of 100° C. or above. In some embodiments, the ablative fluid delivered by treatment element 145 comprises a vaporized fluid at a temperature below 100° C., such as a vaporized fluid at a temperature between 70° C. and 90° C. In some embodiments, the ablative fluid delivered by treatment element 145 comprises a gas, such as a gas between 60° C. and 99° C., such as a gas delivered to tissue at a temperature between 70° C. and 90° C. In some embodiments, the ablative fluid delivered by treatment element 145 comprises a vaporized liquid, such as a vaporized liquid delivered to tissue at a temperature below 100° C., such as at a temperature between 70° C. and 90° C. Alternatively or additionally, an ablative fluid delivered by treatment element 145 can comprise one or more liquids or gases that cause tissue necrosis or otherwise treat target tissue TT as has been described hereabove, using one or more chemically active agents (e.g. ablation not primarily caused by delivery or removal of heat from tissue). In these embodiments, the agent can comprise an agent selected from the group consisting of: sclerotic agent; acid; base; saline; alcohol; carbon dioxide; nitrous oxide; nitrogen; acetic acid; glycerol; and combinations of these. In these embodiments, a counter-acting agent can be included, such as a counter-acting agent delivered by treatment device 100 or another device or component of system 10 that is used to neutralize, impede, reduce and/or limit tissue ablation caused by the delivery of a necrotic agent-based ablative fluid. The counter-acting agent can be delivered by treatment element 145 or another component. The counter-acting agent can comprise an agent selected from the group consisting of: anti-sclerotic agent; base; acid; buffer solution; saline; water; and combinations of these. System 10 can be configured to deliver ablative fluid directly to tissue as is described in applicant's co-pending International PCT Application Serial Number PCT/US2013/54219, entitled "Ablation Systems, Device and Methods for the Treatment of Tissue", filed Aug. 8, 2013, the contents of which are incorporated herein by reference in their entirety.

As shown in FIG. 12, first treatment device 100 includes coaxial shafts 110a and 110b. Shaft 110b has a tip portion 112. In some embodiments, tip portion 112 includes a bulbous element, ball 117. In these embodiments, ball 117 can be sized to fit through a working channel of endoscope 350, such as when ball 117 has a diameter less than 6 mm or less than 4 mm. Alternatively, ball 117 can have a larger diameter configured to assist in smoothly traversing plicae, such as a diameter of at least 8 mm. Shafts 110a and 110b are sized and configured such that shaft 110a slidingly receives shaft 110b, such that they can be advanced and/or retracted in unison or independently. Alternatively, first treatment device 100 can comprise a single shaft. In some embodiments, device 100 comprises a flexible portion (e.g. a portion of shafts 110a and 110b including tip portion 112) with a diameter less than 6 mm. In some embodiments, the flexible portion is configured to pass through a working channel of an endoscope with a diameter of less than or equal to 6.0 mm, 4.2 mm, 3.8 mm, 3.2 mm or 2.8 mm. In some embodiments, device 100 comprises a shaft length of 100 cm or longer, or otherwise comprises a length sufficient to be orally and/or nasally inserted into a patient, and subsequently advanced to reach the esophagus, stomach, duodenum and/or jejunum; and/or rectally inserted into a patient, and subsequently advanced to reach the terminal ileum of that patient. In FIG. 12, shafts 110a and 110b have been inserted through a working channel (e.g. a 6 mm working channel), lumen 351, of endoscope 350, typically a GI endoscope. Shafts 110a and/or 110b can be inserted over a standard interventional guidewire, such as guidewire 60 shown exiting tip portion 112 of shaft 110b. In an alternative embodiment, shafts 110a and 110b are positioned in a side-by-side configuration, such as to be placed in two separate lumens of endoscope 350 or in two other non-coaxial locations. In some embodiments, one or both of shafts 110a or 110b passes through a body lumen or other internal body location alongside endoscope 350 (i.e. not through lumen 351, traveling relatively parallel with but external to endoscope 350). Shaft 110a and/or 110b can include manipulation means configured to deflect and/or steer a distal portion of the shaft, such as via one or more proximal handle controlled pull wires that extend and are attached to the distal portion of the shaft (handle and pull wires not shown but well known to those of skill in the art), such as to deflect and/or steer treatment assembly 140 and/or expandable assembly 130 towards and/or away from tissue and/or assist in navigating treatment assembly 140 through tortuous anatomy.

Treatment assembly 140 can be positioned on shaft 110a as shown. A tissue treatment element, treatment element 145 is electrically, fluidly, mechanically and/or otherwise operably connected to conduit 141. Conduit 141 comprises one or more elongate filaments selected from the group consisting of: a wire such as one or more wires configured to deliver electrical or other power and/or transmit electrical or other data signals; an optical fiber such as one or more optical fibers configured to deliver power and/or transmit data signals; a tube such as a fluid delivery tube; a control rod such as an advanceable and/or retractable control rod; and combinations of these. Conduit 141 travels proximally through shaft 110a and operably attaches to EDU 330, pumping assembly 336, motion transfer assembly 320 and/or another component, assembly or device of system 10.

In some embodiments, conduit 141 comprises one or more fluid delivery tubes constructed and arranged to deliver and/or recirculate heated or chilled fluid into treatment assembly 140, such as heated or chilled fluid received from EDU 330 and/or pumping assembly 336 and delivered into treatment element 145, such as when treatment element 145 comprises a balloon or other fluid reservoir configured to receive ablative fluid at a temperature sufficient to ablate tissue when treatment element 145 contacts the tissue. Alternatively or additionally, conduit 141 can comprise one or more fluid delivery tubes constructed and arranged to deliver an ablative fluid to treatment assembly 140, such as ablative fluid provided by EDU 330 and/or pumping assembly 336 and delivered directly to target tissue TT by one or more treatment elements 145, such as when treatment element 145 comprises a fluid delivery element such as a nozzle. Conduit 141 can further comprise one or more insulating layers configured to prevent transfer of heat into and/or out of conduit 141. Conduit 141 can include a surrounding lumen which receives a circulating fluid configured to provide an insulating, warming and/or cooling effect on conduit 141 and/or any fluid contained within conduit 141. Conduit 141 and/or another fluid delivery tube of system 10 can comprise one or more elongate hollow tubes, such as a hollow tube positioned within shaft 110a. Alternatively, conduit 141 and/or another fluid delivery tube of system 10 can comprise a lumen within a shaft, such as a lumen within shaft 110a. In some embodiments, conduit 141 and/or another fluid delivery tube of system 10 comprises both a lumen and a hollow tube, such as when the lumen and hollow tube are fluidly connected in an end-to-end configuration. Conduit 141 typically attaches to EDU 330 and/or pumping assembly 336 with one or more operator attachable fluid connection ports, such as a fluid connection port included in a handle positioned on the proximal end of shaft 110a, handle not shown. Conduit 141 can comprise one or more fluid delivery tubes including one or more valves, not shown but such as a duck-bill or other valve used to regulate flow within conduit 141, such as to regulate flow pressure and/or direction.

In some embodiments, conduit 141 comprises one or more elongate filaments constructed and arranged to transmit energy and/or data. Conduit 141 can comprise one or more wires constructed and arranged to deliver RF energy to one or more electrode-type treatment elements 145, such as when the treatment elements 145 are configured to ablate target tissue TT in monopolar and/or bipolar modes as described herein. Conduit 141 can comprise one or more filaments constructed and arranged to deliver laser energy, such as one or more optical fibers constructed and arranged to deliver laser energy to one or more lenses or other optical component-type treatment elements 145, such as to ablate target tissue TT with laser or other light energy. Conduit 141 can comprise one or more wires or other energy transfer filaments constructed and arranged to allow a sound producing-type treatment element to ablate target tissue TT with sound energy such as ultrasonic or subsonic sound energy. Conduit 141 can comprise one or more wires or optical fibers configured to transmit information, such as information received from a sensor of system 10 as described herebelow.

In some embodiments, conduit 141 comprises one or more control rods constructed and arranged to cause one or more treatment elements 145 to rotate and/or translate, such as when conduit 141 is operably attached to motion transfer assembly 320, such as prior to, during and/or after delivery of energy to target tissue. In some embodiments, one or more treatment elements 145 comprise a surface configured to abrade or otherwise disrupt tissue as it is rotated and/or translated by movement of conduit 141. Alternatively or additionally, one or more treatment elements 145 can deliver energy and/or fluid to tissue, and movement of one or more control rods of conduit 141 changes the location of the tissue segment receiving the energy and/or fluid. Motion of one or more treatment elements 145 can be configured to treat a full circumferential (i.e. 360°) segment of tubular tissue, or a partial circumferential (e.g. 45°-350°) segment of tubular tissue. Motion of one or more treatment elements 145 can be configured to treat a particular axial length of tubular tissue, such as a length comprising at least 25% of the length of the duodenum, or at least 35% of the length of the duodenum, or at least 50% of the length of the duodenum, or at least 66% of the length of the duodenum; or at least 75% of the length of the duodenum.

Treatment assembly 140 can be radially expandable, similar to expandable assembly 130 described herebelow. System 10 can be configured to allow expansion of treatment assembly 140 to cause one or more treatment elements 145 to contact a tissue wall such as a duodenal wall, such as when one or more treatment elements 145 comprise a balloon configured to ablate tissue with a contained hot or cold fluid, or when one or more treatment elements 145 comprise an electrode configured to deliver RF energy to ablate tissue. Treatment assembly 140 can be configured to expand to a diameter less than the diameter of the target tissue TT, such as when a vacuum is applied to cause the target tissue TT diameter to decrease to make contact with one or more treatment elements 145, as has been described hereabove. System 10 can be configured to allow expansion of treatment assembly 140 to cause one or more treatment elements 145 to be positioned at a fixed distance from the luminal wall of tubular tissue, such as a positioning at a fixed distance of at least 250 microns, at least 500 microns, or at least 1 mm from a tissue wall, such as when one or more treatment elements 145 are configured to deliver ablative fluid to the target tissue TT and/or to deliver light energy to the target tissue TT. In addition to treating target tissue TT, treatment assembly 140 and/or one or more treatment elements 145 can be configured in one or more various forms to modify, manipulate, measure and/or diagnose target tissue TT and/or other tubular or non-tubular tissue.

In some embodiments, treatment element 145 can be further configured to extract fluids, such as to extract previously administered ablative fluids and/or insufflation fluids from a body lumen. Fluid extraction can be performed prior to, during and/or after treatment of target tissue TT.

EDU 330 and/or pumping assembly 336 can comprise multiple heat or cold sources used to modify the temperature of one or more fluids provided by and/or passing through EDU 330 and/or pumping assembly 336. The heat or cold sources can be at a fixed temperature or they can be variable. In some embodiments, a first heat or cold source is at a fixed temperature and a second heat or cold source is at a variable temperature.

In some embodiments, a cooling fluid is delivered, prior to, during and/or after the treatment of target tissue TT, such as to precisely control target tissue ablation and avoid ablation of non-target tissue. The cooling fluid can be provided by EDU 330 and/or pumping assembly 336, and it can be delivered to tissue, such as target or non-target tissue, and/or it can be delivered to a component of system 10 such as to reduce the temperature of a component of treatment assembly 140. Treatment element 145 and/or another component of system 10 can be constructed and arranged to deliver the cooling fluid to one or more tissue surfaces, such as a cooling fluid delivered to treatment element 145 via conduit 141 and configured to reduce the temperature of one or more volumes of tissue. The ablation provided by system 10 can comprise a non-desiccating or a desiccating ablation. In some embodiments, a non-desiccating ablation is performed for a first portion of target tissue TT such as in a first tissue treatment, and a desiccating ablation is performed for a second portion of target tissue TT such as in a second tissue treatment. Non-desiccating ablations can be performed to treat over-lapping portions of target tissue TT, and/or to avoid creation of tissue debris if desired. Desiccating ablations can be performed to achieve a higher thermal gradient, to remove excess tissue, and/or to ablate rapidly if desired.

EDU 330 and/or pumping assembly 336 can be configured to deliver a hot fluid to pre-heat one or more components of system 10. In some embodiments, the one or more components include conduit 141; a fluid delivery tube such as a tube within shaft 110a, a fluid delivery lumen such as a lumen within shaft 110a; shaft 110b; treatment element 145; and combinations of these. System 10 can be configured to pre-heat one or more components by circulating or recirculating hot fluid, such as a hot liquid or gas. In some embodiments, treatment assembly 140 contains and/or treatment element 145 delivers a hot fluid, and one or more components of system 10 are pre-treated with a hot gas. Alternatively or additionally, system 10 can comprise one or more insulators surrounding one or more conduits, lumens and/or shafts of treatment device 100 and/or system 10, such as an insulator surrounding conduit 141 and configured to prevent transfer of heat across (e.g. into or out of) conduit 141.

System 10 can be configured to maintain target tissue TT or other tissue below a threshold or within a temperature range, such as in a closed-loop configuration through the use of one or more sensors such as sensor 149 of treatment assembly 140 or sensor 139 of expandable assembly 130, each described in detail herebelow. In some embodiments, tissue temperature is maintained below 100° C., such as between 60° C. and 90° C., such as between 65° C. and 85° C. In some embodiments, system 10 is configured to maintain the temperature of target tissue TT at a setpoint temperature. The setpoint temperature can vary over time. System 10 can be configured to deliver energy at a level that increases and/or decreases over time. In some embodiments, treatment element 145 is constructed and arranged to cause the temperature of at least a portion of target tissue TT to rapidly rise to a setpoint (e.g. a setpoint between 60° C. and 75° C.). After the target tissue TT reaches the setpoint temperature, system 10 can deliver energy or otherwise treat the target tissue TT to maintain the setpoint temperature for an extended time period.

In some embodiments, EDU 330 and/or pumping assembly 336 is configured to heat or chill one or more fluids, such as one or more ablative fluids provided by ablative fluid reservoir 331, or other fluids. In some embodiments, treatment assembly 140 is configured to heat or chill one or more fluids. Applicable heating and cooling elements include but are not limited to heat exchangers, heating coils, peltier components, refrigeration assemblies, gas expansion coolers, and the like. Heating and cooling can be applied to a source of fluid (e.g. fluid reservoir 333), or to fluid that is withdrawn from device 100 (e.g. a recirculating fluid and/or a body extracted fluid such as recovered, previously delivered, ablative or insufflating fluid). EDU 330 and/or pumping assembly 336 can include one or more pumps configured to deliver and/or extract fluid at a particular flow rate, pressure, or other fluid delivery parameter. System 10 can be configured to deliver fluid at a sufficiently high temperature to ablate target tissue TT, after which a cooling fluid is delivered to removal thermal energy from target tissue TT and/or other tissue, such as cooling fluid delivered for a time period of at least 2 seconds, at least 5 seconds, at least 10 seconds or at least 20 seconds.

In some embodiments, treatment device 100 further includes a radially expandable assembly, expandable assembly 130, mounted to shaft 110b. In some embodiments, treatment device 100 comprises a single shaft, and both treatment assembly 140 and expandable assembly 130 are mounted to that single shaft. Expandable assembly 130 can be configured in one or more various forms to treat, modify, manipulate, measure and/or diagnose target tissue TT and/or other tubular tissue. Expandable assembly 130 can comprise one or more expandable elements 131, such as one or more expandable elements selected from the group consisting of: an inflatable balloon; a radially expandable stent or cage; an array of splines; one or more radially deployable arms; a spiral or other helical structure; a furlable structure such as a furlable sheet; an unfurlable structure such as an unfurlable sheet; a foldable structure such as a foldable sheet; an unfoldable structure such as an unfoldable sheet; and combinations of these. In some embodiments, expandable assembly 130 is inflatable (e.g. an inflatable balloon), and inflation fluid can be delivered into expandable assembly 130 via an inflation tube 136. Inflation tube 136 can comprise a lumen of shaft 110b (or a tube within shaft 110b) that travels proximally through shaft 110b and shaft 110a, such as to receive inflation fluid delivered by pumping assembly 336. Expandable assembly 130 can be positioned distal to treatment assembly 140 as shown in FIG. 12, or alternatively, expandable assembly 130 can be positioned proximal to treatment assembly 140, such as when treatment assembly 140 is mounted to shaft 110b and expandable assembly 130 is mounted to shaft 110a.

Expandable assembly 130 can be configured to seal a body lumen location, such as to create a full or partial occlusive barrier at a location within the duodenum or other location in the GI tract. System 10 can be configured to cause a fluid or other seal comprising an occlusive barrier selected from the group consisting of: a pressure seal; a cryogenically applied seal such as an ice ball seal; a vacuum seal; a full circumferential seal; a partial circumferential seal; and combinations of these. In some embodiments, treatment element 145 treats a portion of target tissue TT located proximal or distal to the occlusive barrier. System 10 can include multiple expandable assemblies configured to seal a body lumen location, such as first expandable assembly which provides a seal at a proximal end of a segment of tubular tissue, and a second expandable assembly which provides a seal at a distal end of the tubular tissue segment. In some embodiments, treatment element 145 treats a portion of target tissue TT located between the two sealed locations, such as between two locations of the duodenum, each duodenal location sealed by an expandable component or assembly of device 100. One or more expandable assemblies can be configured to occlude a first location of a body lumen, followed by subsequent occlusions of one or more different locations within the body lumen. System 10 can be configured to apply a vacuum between two occlusive elements, such as a vacuum applied by one or more treatment elements 145, via one or more functional elements 138 and/or 148 (attached to expandable assembly 130 and treatment assembly 140, respectively, each functional element described in detail herebelow) and/or by another device or component of system 10. Applied vacuum can be used to modify (e.g. change the shape of) the tubular tissue between the two occlusive elements and/or to increase the sealing force and/or the circumferentiality of the seal. In some embodiments, system 10 is configured to deploy a detached-balloon configured to occlude a body lumen, where the detached-balloon can later be punctured or otherwise deflated for physiologic removal by the GI tract. Deployed balloons or other occlusive elements of system 10 can be positioned to protect tissue, such as to protect the ampulla of Vater and/or the pylorus from adverse effects that can be caused by treatment of target tissue TT by treatment element 145.

In some embodiments, in addition to expandable assembly 130, treatment assembly 140 can be radially expandable and/or include one or more radially expandable elements, such as those described hereabove in reference to expandable assembly 130. In some embodiments, treatment assembly 140 is configured to radially expand and cause treatment element 145 to move closer to and/or become in contact with target tissue TT. Expansion of treatment assembly 140 can occur prior to, during and/or after treatment of target tissue TT by treatment element 145. Treatment element 145 can be mounted on, within and/or inside of an expandable assembly, such as on, within and/or inside of an expandable balloon.

In some embodiments, expandable assembly 130 and/or treatment assembly 140 comprise a length of at least 10 mm, such as a length between 10 mm and 40 mm, a length between 15 mm and 30 mm, or a length between 20 mm and 25 mm. In some embodiments, expandable assembly 130 and/or treatment assembly 140 comprise a length less than or equal to 15 mm, such as when configured to treat curvilinear portions of the GI tract. Multiple assemblies positioned on shafts 110a and/or 110b (e.g. between two and twenty treatments and/or expandable assemblies), such as expandable assembly 130 and treatment assembly 140, can be separated along a shaft by a distance less than or equal to 25 mm, such as a distance less than or equal to 20 mm. This separation distance can comprise the distance between a distal end of a tissue contacting portion of a first expandable element, and the neighboring proximal end of a tissue contacting portion of a second expandable element. In some embodiments, expandable assembly 130 comprises a length, and the separation distance between expandable assembly 130 and treatment assembly 140 is less than or equal to the expandable assembly 130 length. In these embodiments, treatment assembly 140 can comprise a similar length to that of expandable assembly 130, such as when both expandable assembly 130 and treatment assembly 140 comprise an ablation element as is described herebelow.

Expandable assembly 130 can include one or more fluid delivery elements, such as fluid delivery element 132 and/or fluid delivery element 135. Fluid delivery elements 132 and 135 are connected to one or more fluid delivery tubes (e.g. independent fluid delivery tubes), not shown but traveling proximally within shafts 110b and/or 110a and fluidly connected to EDU 330 and/or pumping assembly 336, such as via one or more ports on a handle of treatment device 100. Fluid delivery elements 132 and/or 135 can be rotatable, advanceable and/or retractable, such as via one or more control shafts, not shown but operably connected to motion transfer assembly 320. Fluid delivery elements 132 and/or 135 can comprise a nozzle or other fluid delivery element as described herein. Fluid delivery element 132 can be oriented such that fluid delivered through fluid delivery element 132 is directed toward one or more device 100 components or assemblies, such as toward treatment assembly 140 and treatment element 145 as shown in FIG. 12. Fluid delivery element 132 can be used to perform various functions such as the washing or removing of material from a device 100 component, or to cool or warm the temperature of a device 100 component. Fluid delivery element 135 can be directed toward or otherwise deliver fluid to tissue proximate device 100. Fluid delivery element 135 can have its distal end positioned within tissue (e.g. after an advancement), as shown in FIG. 12, such as to deliver fluid to one or more internal tissue layers. Alternatively, fluid delivery element 135 can have its distal end positioned in a body lumen, such as to deliver fluid to at least initially contact a tissue surface such as the wall of the duodenum. Fluid delivery element 135 can be configured to deliver a fluid to expand tissue. Alternatively or additionally, a separate submucosal or other tissue expansion device can be included, such as tissue expansion device 200. Fluid delivery element 135 and/or tissue expansion device 200 can be constructed and arranged to expand tissue as is described in applicant's co-pending International PCT Application Serial Number PCT/US2013/37485, entitled "Tissue Expansion Devices, Systems and Methods", filed Apr. 19, 2013, the contents of which is incorporated herein by reference in its entirety. Fluid delivery element 135 can be configured to deliver a cooling or warming fluid to tissue, and/or deliver a fluid configured to counter-act a chemically caused ablation, as has been described hereabove. System 10 can include one or more fluids or other material to expand one or more layers of tissue, such as when tissue expansion device 200 includes an injectable tissue-expanding material, such as a non-energy absorbing material and/or an energy-absorbing material such as water or saline.

Expandable assembly 130 and/or treatment assembly 140 can be configured to expand to a diameter of at least 10 mm, such as a diameter of at least 15 mm, at least 20 mm, at least 25 mm, at least 30 mm, or at least 40 mm. In some embodiments, expandable assembly 130 and/or treatment assembly 140 can expand to a diameter between 15 mm and 32 mm. In some embodiments, expandable assembly 130 and/or treatment assembly 140 have their diameter controlled by a component of system 10 (e.g. controller 310, EDU 330 and/or pumping assembly 336), such as to control the diameter to at least 10 mm, at least 15 mm, at least 20 mm, at least 25 mm, at least 30 mm, or at least 40 mm, or to control the diameter to a diameter between 15 mm and 32 mm. Expandable assembly 130 and/or treatment assembly 140 can be resiliently biased, such as in a radially expanded or radially compacted state. Expandable assembly 130 and/or treatment assembly 140 can be expanded and/or compacted by a control shaft. Expandable assembly 130 and/or treatment assembly 140 can be configured to achieve a round or non-round shape (e.g. a football shape) when expanded. Expandable assembly 130 and/or treatment assembly 140 can approximate a tubular shape when expanded, such as a relatively constant diameter or varying diameter tube shape. Expandable assembly 130 and/or treatment assembly 140 can be configured to un-fold to a radially expanded state, or to fold to a radially compacted state.

Expandable assembly 130 can comprise at least one functional element 138, and treatment assembly 140 can comprise at least one functional element 148. Functional elements 138 and/or 148 can be elements selected from the group consisting of: an ablation element such as one or more electrodes configured to deliver electrical energy such as radiofrequency (RF) energy; a sensor; a transducer; a fluid delivery element such as a needle, a fluid jet, a permeable membrane and/or an exit port; a heating element; a cooling element; and combinations of these.

In some embodiments, expandable assembly 130 is configured to ablate tissue, such as via functional element 138. Functional element 138 of expandable assembly 130 can comprise one or more ablation elements, such as those described in applicant's co-pending U.S. patent application Ser. No. 13/945,138, entitled "Devices and Methods for the Treatment of Tissue", filed Jul. 18, 2013, the contents of which is incorporated herein by reference in its entirety. In some embodiments, functional element 138 comprises an ablation element selected from the group consisting of: an RF energy delivery element such as one or more electrodes, each comprising one or more elongate conductors; an ultrasonic transducer such as one or more piezo crystals configured to ablate tissue; a laser energy delivery element such as one or more optical fibers and/or laser diodes; a heat delivery element such as a hot fluid filled balloon; a rotating ablation element; a circumferential array of ablation elements; and combinations of these. In these embodiments, either or both expandable assembly 130 or treatment assembly 140 can be used to ablate target tissue TT. EDU 330 or another component of system 10 can be configured to deliver RF or other energy to functional element 138. System 10 can include ground pad 70, such as a standard RF energy delivery ground pad typically placed on the patient's back, such that EDU 330 can supply RF energy to functional element 138 and/or any other electrodes of system 10 in monopolar, bipolar and/or combined monopolar-bipolar energy delivery modes.

In some embodiments, expandable assembly 130 is configured to perform at least one non-ablative function. Expandable assembly 130 can be configured to occlude or partially occlude a lumen surrounded by tissue (as described hereabove), such as a lumen of the GI tract to be occluded during an insufflation procedure. Expandable assembly 130 can be configured to manipulate tissue, such as to linearize and/or distend GI tissue by frictionally engaging (e.g. when expanded) and applying forces to the tissue (e.g. by advancing and/or retracting shaft 110*b*). In some embodiments, one or more expandable assemblies 130 can perform a function selected from the group consisting of: linearizing curvilinear tissue; distending tissue; expanding tissue; occluding a body lumen; and combinations of these. Expandable assembly 130 can be configured to test and/or diagnose tissue, such as when expandable assembly 130 is used to measure a diameter of tubular tissue into which it has been inserted. Diameter measurements can be performed in various ways, including but not limited to: injection of a radiopaque fluid into expandable assembly 130 and fluoroscopic measurement of the injected fluid; controlled inflation of expandable assembly 130 to a pressure whose level corresponds to a luminal diameter; and combinations of these. In some embodiments, device 100 includes an expandable assembly that can be expanded with one or more control rods (not shown), such as to perform a diametric measurement of tubular tissue by precision measurement of control rod advancement (e.g. when control rod position correlates to expandable assembly diameter). Alternatively or additionally, tubular tissue diameter can be determined by measuring the diameter of an expandable assembly when it initially, circumferentially contacts the wall of tubular tissue (e.g. when a specific radial force is achieved and/or when contact is observed such as using fluoroscopy or ultrasound visualization devices). In some embodiments, system 10 includes a separate device, such as a balloon catheter, used to perform a diameter measurement. One or more energy delivery or other ablation parameters can be adjusted based on the measured diameter of target tissue TT and/or a target tissue segment.

In some embodiments, expandable assembly 130 is configured to expand or otherwise modify one or more layers of tissue, such as when fluid delivery element 135 and/or functional element 138 comprises a needle, water jet and/or iontophoretic fluid delivery element configured to expand submucosal tissue of the GI tract, as has been described hereabove. Alternatively or additionally, system 10 can include a separate tissue expansion device, tissue expansion device 200. Tissue expansion device 200 can comprise a reservoir or control means for delivering a pre-determined amount of fluid to tissue, such as a volume of fluid of at least 1 ml, or a volume of fluid between 2 ml and 5 ml. Tissue expansion device 200 can be configured to inject fluid into multiple injection sites (e.g. simultaneously or sequentially), such as a set of multiple injection sites selected from the group consisting of: at least 3 injection sites along a circumference of tubular tissue, a first circumferential injection site separated from a second circumferential injection site by approximately 1 cm, or between 0.5 cm to 5 cm, or between 1 cm and 3 cm, or between 1 cm and 2 cm; two or more injection sites that are axially and/or radially spaced; two or more injections sites that are separated based on the diameter of the tubular tissue into which they are injected; and combinations of these. Fluid can be injected with the assistance of one or more vacuum applying elements positioned on or near fluid delivery elements 132 and/or 135, these one or more elements configured to apply negative pressure proximate the injection site. Injected fluid can comprise a material selected from the group consisting of: water; saline; gel; and combinations of these. In some embodiments, injected fluid comprises a protein hydrogel.

Tissue expansion can greatly alleviate the need for precision of treatment, such as precision of delivery of energy and/or precision of delivery of an ablative fluid, due to the increased size (e.g. increased depth) of the target tissue TT including an associated safety-margin of tissue to which treatment causes no significant adverse event (e.g. an expanded submucosal layer prior to a mucosal layer ablation).

In some embodiments, expandable assembly 130 and/or treatment assembly 140 comprise a shape that can be adjusted by an operator, such as via a control rod manipulatable at a proximal handle and/or by motion transfer assembly 320. In some embodiments, the shape of the arrangement of one or more treatment elements 145 can be operator modified by adjusting the shape of treatment assembly 140.

Treatment element 145 can be configured to treat various thicknesses of GI tissue, such as at least the innermost 500 microns of duodenal tissue, or at least the innermost 1 mm of duodenal tissue. In some embodiments, treatment element 145 can be configured to ablate or otherwise treat a thickness of at least 600 microns, at least 1 mm or at least 1.25 mm, such as when treating the mucosa of the stomach. Treatment element 145 can be configured to treat a volume of tissue comprising a surface area and a depth, where the ratio of magnitude of the depth to the magnitude of the surface area is less than or equal to 1 to 100 (e.g. less than 1%), or less than or equal to 1 to 1000 (e.g. less than 0.1%). In some embodiments, expandable assembly 130 and/or treatment assembly 140 are configured to be in a relatively rigid state, such as during treatment of target tissue TT.

Treatment element 145 and/or other treatment elements of the present inventive concepts can be arranged in an array of elements, such as a circumferential or linear array of elements. The circumferential array can comprise a partial circumferential array of treatment elements 145, such as an array covering approximately 45° to 300° of circumferential area. Partial circumferential arrays of treatment elements 145 can treat a first target tissue segment and a second target tissue segment in two sequential steps, where the array is rotated between treatments (e.g. energy deliveries). The circumferential array can comprise a full 360° array of treatment elements 145, such that a full circumferential volume of target tissue TT can be treated in single or multiple treatments (e.g. energy deliveries) that do not require repositioning of treatment assembly 140. In some embodiments, less than 360° of tubular tissue is treated, such as by treating a circumferential portion of tissue comprising less than or equal to a 350°, or between 300° and 350°, such as to prevent a full circumferential scar from being created.

Two or more treatment elements 145 can be arranged in a helical array. In some embodiments, at least three, four or five treatment elements independently treat target tissue, in similar or dissimilar treatments (e.g. similar or dissimilar amounts of energy, provided simultaneously and/or sequentially by EDU 330).

In some embodiments, EDU 330 and/or another device or component of system 10 provides electrical or other energy to a component of treatment device 100, such as electrical energy provided to a heating coil in a distal portion of device 100, now shown but typically connected to one or more wires traveling proximally through shaft 110a. EDU 330 and/or another device or component of system 10 can provide energy such as electrical energy to one or more of functional element 138 and/or functional element 148 such as when either comprises a transducer or other powered component.

Treatment element 145 can comprise one or more treatment elements configured to treat substantially the entire length of the duodenum simultaneously and/or without having to reposition treatment device 100, such as when treatment element 145 comprises an array of treatment elements positioned along substantially the entire length of the target tissue, or when treatment element 145 comprises at least one treatment element configured to rotate and/or translate along substantially the entire length of target tissue. Treatment element 145 and/or other tissue treatment elements of the present inventive concepts can be configured to treat at least 25% of the entire length of the duodenum simultaneously and/or without having to reposition treatment device 100. Treatment element 145 and/or other ablation elements of the present inventive concepts can be configured to treat a first portion of target tissue TT followed by a second portion of target issue TT. The first and second treated tissue segments can be overlapping and they can have non-parallel central axes (e.g. tissue segments in a curved portion of the duodenum). Three or more target tissue segments can be treated, such as to cumulatively ablate at least 25% or at least 50% of the duodenal mucosa.

In some embodiments, expandable assembly 130 and/or treatment assembly 140 comprise inflatable or otherwise expandable balloons, such as one or more of: a compliant balloon; a non-compliant balloon; a balloon with a pressure threshold; a balloon with compliant and non-compliant portions; a balloon with a fluid entry port; a balloon with a fluid exit port; and combinations of these. In some embodiments, expandable assembly 130 and/or treatment assembly 140 comprise a balloon which is fluidly attached to an inflation tube, such as inflation tube 136 which travels proximally through shaft 110a and/or 110b and is attached to an inflation port, not shown but typically attached to a handle on the proximal end of treatment device 100.

In some embodiments, functional element 138 of expandable assembly 130 comprises an abrasive element configured for abrading target tissue, such as an abrasive element attached to a balloon or expandable cage.

Shafts 110a and 110b can include one or more lumens passing therethrough, and can comprise wires and/or optical fibers for transfer of data and/or energy such as RF energy to functional element 138 and/or 148. Shafts 110b and/or 110a can comprise one or more shafts, such as one or more concentric shafts configured to deliver and/or recirculate hot and/or cold fluid through expandable assembly 130 and/or treatment assembly 140, respectively. In some embodiments, a heated fluid is used to pre-heat one or more treatment device 100 components and/or to deliver a bolus of hot fluid energy, each as described in applicant's co-pending International Application Serial Number PCT/US2013/28082, entitled "Heat Ablation Systems, Devices and Methods for the Treatment of Tissue", filed Feb. 27, 2013, the contents of which is incorporated herein by reference in its entirety. Device 100 can comprise multiple expandable assemblies 130, such as a first expandable assembly positioned proximal to treatment assembly 140 (not shown) and a second expandable assembly positioned distal to treatment assembly 140 (expandable assembly 130 as shown in FIG. 12).

Treatment assembly 140 and/or expandable assembly 130 can be configured to ablate tissue or otherwise perform a function while positioned in a curved segment of the GI tract, such as is described in reference to FIGS. 4 and 6 hereabove.

System 10 can be configured to ablate or otherwise treat target tissue TT, such as duodenal mucosal tissue, while avoiding damaging non-target tissue, such as the GI adventitia. Target tissue TT can include at least a portion of safety-margin tissue comprising tissue whose ablation causes minimal or no adverse effect to the patient, such as sub-mucosal tissue of the GI tract. Target tissue TT can comprise one or more portions of tissue that are treated simultaneously or sequentially. In some embodiments, the target tissue TT comprises the majority of the length of the duodenal mucosa, such as at least 25% or at least 50% of the duodenal mucosa. In some embodiments, the target tissue TT comprises at least 90% of the duodenal mucosa, or at least 95% of the duodenal mucosa. In some embodiments, the target tissue TT includes the full mucosal thickness of at least a portion of duodenal tissue, as well as at least the innermost 100 microns of submucosal duodenal tissue, or at least the innermost 200 microns of submucosal duodenal tissue. The target tissue TT can include at least one of ileal mucosal tissue or gastric mucosal tissue.

Endoscope 350 can be a standard endoscope, such as a standard GI endoscope, or a customized endoscope, such as an endoscope including sensor 353 configured to provide information related to the tissue treatment of the present inventive concepts. Endoscope 350 can include camera 352, such as a visible light, ultrasound and/or other visualization device used by the operator of system 10 prior to, during and/or after the treatment of target tissue TT, such as during insertion and/or removal of endoscope 350 and/or shafts 110a and 110b of treatment device 100. Camera 352 can provide direct visualization of internal body spaces and tissue, such as the internal organs of the GI tract. Endoscope 350 can be coupled with or otherwise include a guidewire, e.g. guidewire 60, such as to allow insertion of endoscope 350 into the jejunum and/or advancement of treatment device 100.

System 10 can be constructed and arranged to perform insufflation of a body lumen, such as insufflation of a segment of the GI tract. The body lumen can be pressurized, such as by using one or more standard insufflation techniques. Insufflation fluid can be introduced through second lumen 354 of endoscope 350. Second lumen 354 travels proximally and connects to a source of insufflation liquid and/or gas, such as pumping assembly 336, and typically a source of air, carbon dioxide, water and/or saline. Alternatively or additionally, insufflation fluid can be delivered by treatment device 100, such as through shaft 110a and/or 110b, and/or through a port in expandable assembly 130 and/or treatment assembly 140, such as when functional elements 138 and/or 148, respectively, comprise a fluid delivery port attached to a source of insufflation liquid and/or gas (e.g. provided by pumping assembly 336). Alternatively or additionally, a separate device configured to be inserted through endoscope 350 and/or to be positioned alongside endoscope 350, can have one or more lumens configured to deliver the insufflation fluid. System 10 can include one or more occlusive elements and/or devices, such as expandable assembly 130, treatment assembly 140 and/or another expandable device configured to radially expand such as to fully or partially occlude a body lumen, such that insufflation pressure can be achieved and/or maintained over time (e.g. reduce or prevent undesired migration of insufflation fluid). The one or more occlusive elements and/or devices can be positioned proximal to and/or distal to the luminal segment to be insufflated.

Pumping assembly 336 can be configured to remove fluid from a body lumen such as a segment of the GI tract. Removed fluids include but are not limited to: delivered ablative fluid; condensate of delivered ablative fluid; insufflation fluids; excess bodily fluids; chyme; digestive fluids; gas; and combinations of these. Fluids can be removed prior to, during and/or after treatment of target tissue TT by treatment element 145. Pumping assembly 336 can be configured to apply a vacuum, such as to remove fluid via at least one treatment element 145, an outflow drain, or other fluid extraction port of system 10. In some embodiments, extracted fluids are recycled, such as for subsequent delivery by at least one treatment element 145 to target tissue TT.

Pumping assembly 336 and/or EDU 330 can be configured to deliver one or more gases (e.g. carbon dioxide, nitrogen, nitrous oxide and/or air) to at least one treatment element 145 or another gas delivering component of system 10. In some embodiments, at least one treatment element 145 comprises a gas jet nozzle configured to deliver gas to target tissue, such as a gas than has been processed to remove moisture or otherwise be dry (e.g. less than the dew point of air, or at a relative humidity less than 20% or less than 10%). In some embodiments, system 10 is configured to deliver gas to cause agitation of an ablative fluid previously delivered within a body lumen. System 10 can be configured to deliver dry or other gas to move ablative fluid in a body lumen. The delivered gas can comprise a cooling gas, such as a gas below 37° C., a gas between 0° C. and 7° C. such as a gas between 2° C. and 7° C., and/or a gas at approximately 4° C. System 10 can deliver cooling gas for a time period of at least 10 seconds, at least 20 seconds or at least 30 seconds. In some embodiments, system 10 delivers cooling gas at a temperature less than 0° C. for a time period less than or equal to 20 seconds, less than or equal to 10 seconds, or less than or equal to 5 seconds. In some embodiments, system 10 is configured to deliver gas at a temperature at or above 42° C., such as to remove moisture or otherwise dry a tissue wall of the GI tract. System 10 can be configured to deliver carbon dioxide gas.

Functional element 138 and/or functional element 148 can comprise a sensor. In some embodiments, functional element 138, functional element 148, sensor 353 and/or another sensor of system 10, such as sensor 139 positioned on expandable assembly 130 and/or sensor 149 positioned on treatment assembly 140, can comprise a sensor selected from the group consisting of: temperature sensors such as thermocouples, thermistors, resistance temperature detectors and optical temperature sensors; strain gauges; impedance sensors such as tissue impedance sensors; pressure sensors; blood sensors; optical sensors such as light sensors; sound sensors such as ultrasound sensors; electromagnetic sensors such as electromagnetic field sensors; visual sensors; and combinations of these. The sensors can be configured to provide information to one or more components of system 10, such as to controller 310 and/or EDU 330, such as to monitor the treatment of target tissue TT and/or to treat target tissue TT in a closed loop configuration. Energy delivery from EDU 330 can be initiated, stopped and/or modified based on one or more sensor readings. Algorithm 311 of controller 310 and/or EDU 330 can be configured to determine one or more treatment parameters. In some embodiments, algorithm 311 processes one or more sensor signals to modify an amount of ablative fluid delivered, rate of ablative fluid delivery, energy delivered, power of energy delivered, voltage of energy delivered, current of energy delivered and/or temperature of ablative fluid or energy delivered. Alternatively or additionally, algorithm 311 can comprise an algorithm configured to determine an energy delivery zone parameter such as an energy delivery zone parameter selected from the group consisting of: anatomical location of an energy delivery zone; size of energy delivery zone; percentage of energy delivery zone to receive energy; type of energy to be delivered to an energy delivery zone; amount of energy to be delivered to an energy delivery zone; and combinations of these. Information regarding the energy delivery zone parameter can be provided to an operator of system 10. This information can be employed to set an energy delivery zone parameter, assist the operator in determining the completion status of the procedure (e.g. determining when the procedure is sufficiently complete) and/or to advise the operator to continue to complete a pre-specified area or volume of target tissue. The total area of treatment or number of energy delivery zones or number of treatments during a particular procedure (any of which can be employed in algorithm 311) can be defined by patient clinical or demographic data, as described herein.

Sensor 149 of treatment assembly 140 can comprise a gravimetric sensor. In these embodiments, sensor 149 can comprise an accelerometer or other sensor configured to provide a signal representing the orientation of treatment assembly 140 and/or treatment element 145 as it relates to the force of earth's gravity. In embodiments in which treatment element 145 delivers ablative fluid to target tissue TT, the signal provided by sensor 149 can provide information for manual and/or automated control of ablative fluid delivery direction. In some embodiments, gravimetric orientation of device 100 is provided to an operator, such as via a screen on controller 310. In some embodiments, the signal from sensor 149 is recorded by controller 310, such as to adjust a spray pattern delivered by treatment assembly 140 and/or treatment element 145. Based on a signal from sensor 149, treatment element 145 and/or shaft 110a can be positioned to deliver ablative fluid in upward and/or side-ways (i.e. horizontal) directions, such as to allow delivered fluid to flow across the walls of a lumen in a downward direction. Controller 310 can be configured to adjust the flow pattern of ablative fluid delivery by adjusting the rotation and/or translation of treatment assembly 140 (e.g. by creating an asymmetric movement). Controller 310 can be configured to adjust the flow pattern of ablative fluid delivery by adjusting which of multiple treatment elements 145 deliver ablative fluid (e.g. by turning on one or more electronic fluid valves) or by adjusting a nozzle direction or nozzle flow path geometry of treatment element 145 (e.g. when treatment element 145 comprises a rotatable nozzle and/or a nozzle with an adjustable orifice). In some embodiments, controller 310 utilizes a signal from sensor 149 to manipulate one or more treatment elements 145 to deliver fluid in a relatively upward direction. In some embodiments, system 10 includes a fluid removal element, such as a treatment element 145 configured to remove fluid by an outflow drain, and the fluid removal element is gravimetrically oriented by a signal provided by sensor 149.

Sensors 139 and/or 149 can comprise a chemical detection sensor, such as a chemical detection sensor to confirm proper apposition of expandable assembly 130 and/or treatment assembly 140. In this configuration, a chemical sensor such as a carbon dioxide sensor can be placed distal to expandable assembly 130 and/or treatment assembly 140, and a fluid such as carbon dioxide gas can be introduced proximal to the expandable assembly 130 and/or treatment assembly 140. Detection of the introduced fluid by sensor 139 and/or 149 can indicate inadequate apposition of expandable assembly 130 and/or treatment assembly 140, respectively. Readjustment to achieve sufficient apposition can prevent inadequate treatment of target tissue TT (e.g. inadequate transfer of energy) and/or prevent inadequate measurement, modification, manipulation and/or diagnosis of target tissue TT.

Functional element 138, functional element 148, sensor 139, sensor 149, sensor 353 and/or another sensor of system 10 can be a sensor configured to provide information related to the tissue treatment performed by treatment assembly 140 and/or expandable assembly 130, such as a visual sensor mounted to treatment assembly 140 and/or expandable assembly 130 that is configured to differentiate tissue types that are proximate treatment assembly 140 and/or expandable assembly 130. In some embodiments, system 10 is constructed and arranged to differentiate mucosal and submucosal tissue, such as to adjust one or more treatment parameters (e.g. to stop treatment and/or modify the temperature of treatment) based on the differentiation. Applicable visible sensors include but are not limited to: visible light camera; infrared camera; CT Scanner; MRI; and combinations of these. In some embodiments, energy provided by EDU 330 is based on one or more signals from the visible sensor, such as a sensor providing a signal correlating to tissue color wherein the energy delivered is modified based on a tissue color change. Sensors 149 and 139 can comprise a sensor configured to provide information related to the tissue treatment performed by treatment assembly 140 and/or expandable assembly 130, respectively, such as a temperature sensor configured to monitor the temperature of treatment provided by treatment assembly 140 and/or expandable assembly 130 and/or tissue proximate treatment assembly 140 and/or expandable assembly 130. Sensors 149 and/or 139 can comprise multiple temperature sensors, such as multiple temperature sensors positioned on treatment assembly 140 and/or expandable assembly 130, respectively, with a spacing of at least one sensor per square centimeter. Energy delivered by EDU 330 can be based on signals recorded by the multiple temperature sensors.

Functional element 138 and/or functional element 148 can comprise a transducer. In these and other embodiments, functional element 138, functional element 148, and/or another transducer of system 10 can be a transducer selected from the group consisting of: a heat generating element; a drug delivery element such as an iontophoretic drug delivery element; a magnetic field generator; an ultrasound wave generator such as a piezo crystal; a light producing element such as a visible and/or infrared light emitting diode; and combinations of these.

In some embodiments, EDU 330 and/or another device of component of system 10 is configured to deliver a visualizable material, such as a visualizable material delivered to one or more treatment elements 145. In some embodiments, visualizable material is delivered by treatment element 145 onto and/or beneath the surface of tissue, to assist in the treatment of target tissue TT, such as to assess the status of tissue ablation. In some embodiments, the visualizable material is selected from the group consisting of: radiopaque agent; ultrasonically visible material; magnetically visible material; and combinations of these. An imaging device of system 10, such as imaging device 410 described hereinbelow, can be used to create an image of the visualizable material during and/or after delivery of the visualizable material.

In some embodiments, EDU 330 or another device of component of system 10 is configured to deliver abrasive particles, such as abrasive particles delivered to one or more treatment elements 145. In some embodiments, visualizable material is also delivered by EDU 330 to assist in the treatment of tissue, such as to improve ablation caused by a mechanical abrasion treatment.

In some embodiments, EDU 330 is configured to deliver at least RF energy, and system 10 includes ground pad 70 configured to be attached to the patient (e.g. on the back of the patient), such that RF energy can be delivered in monopolar delivery mode to one or more electrode-based treatment elements 145 of treatment device 100 or to one or more electrodes of another treatment device of system 10 (e.g. second treatment device 100'). Alternatively or additionally, EDU 330 can be configured to deliver energy in a bipolar RF mode, such as bipolar energy delivered between any two electrode-based treatment elements 145 of treatment device 100 or between any other two electrodes of another treatment device of system 10. Alternatively or additionally, EDU 330 can be configured to deliver energy in a combined monopolar-bipolar mode.

EDU 330 can be configured to deliver RF and/or other forms of energy to one or more treatment elements 145 of treatment assembly 140 and/or a treatment element expandable assembly 130. In some embodiments, EDU 330 delivers energy selected from the group consisting of: RF energy; microwave energy; plasma energy; ultrasound energy; light energy; and combinations of these. Energy can be continuous and/or pulsed, and can be delivered in a closed-loop fashion as described hereabove. Energy delivery parameters such as power, voltage, current and frequency can be held relatively constant or they can be varied by EDU 330. Energy delivery can be varied from a first tissue location (e.g. a first portion of target tissue TT) to a second location (e.g. a second portion of target tissue TT), such as a decrease in energy from a first treated location to a second treated location when the second treated location is thinner than the first treated location. Alternatively or additionally, energy delivery can be varied during a single application of energy to a single tissue location, such as by adjusting one or more energy delivery parameters during a continuous energy delivery. Alternatively or additionally, one or more energy delivery parameters can be varied between a first treatment of target tissue and a second treatment of target tissue, for example a first treatment performed during a first clinical procedure and a second treatment performed during a second clinical procedure, such as when the second treatment is performed at least twenty-four hours after the first treatment.

Pumping assembly 336 and/or EDU 330 typically include one or more fluid pumps, such as one or more peristaltic, displacement and/or other fluid pumps; as well as one or more heat exchangers and/or other fluid heating elements internal and/or external to device 100. Pumping assembly 336 and/or EDU 330 can be configured to rapidly deliver and/or withdraw fluid to and/or from treatment assembly 140 and/or expandable assembly 130 via one or more fluid transport means. Fluid transport means can include a pump configured to deliver fluid at a flow rate of at least 50 ml/min and/or a pump and/or vacuum source configured to remove fluid at a flow rate of at least 50 ml/min. In some embodiments, system 10 is configured to deliver fluid, such as a liquid, at a flow rate of at least 500 ml/min, or at least 750 ml/min. A pump and/or vacuum source can be configured to continuously exchange hot fluid and/or to perform a negative pressure priming event to remove fluid from one or more fluid pathways of device 100. Pumping assembly 336, EDU 330, first treatment device 100 and or second treatment device 100' can include one or more valves in the fluid delivery and/or fluid withdrawal pathways or one or more other valves in the fluid pathway within treatment assembly 140 and/or expandable assembly 130. Valves can be configured to control entry of fluid into an area and/or to maintain pressure of fluid within an area. Valves can be used to transition from a heating fluid, such as a fluid of 90° C. maintained in a treatment assembly for approximately 12 seconds, to a cooling fluid, such as a fluid between 4° C. and 10° C. maintained in the assembly element for approximately 30 to 60 seconds. Typical valves include but are not limited to: duck-bill valves; slit valves; electronically activated valves; pressure relief valves; and combinations of these. Pumping assembly 336 and/or EDU 330 can be configured to rapidly inflate and/or deflate treatment assembly 140 and/or expandable assembly 130. Pumping assembly 336 and/or EDU 330 can be configured to purge the fluid pathways of first treatment device 100 and/or second treatment device 100' with a gas such as air, such as to remove cold and/or hot fluid from the devices and/or to remove gas bubbles from the devices.

EDU 330, treatment element 145 and/or other components of system 10 can be configured to treat target tissue TT with a non-desiccating ablation, such as by avoiding tissue temperatures above 100° C., avoiding the creation of steam, or otherwise avoiding deleterious desiccation of tissue. System 10 can be configured to minimize heat production in the outermost 50% of a mucosal layer, such as to ablate the outermost 50% of the mucosal layer via thermal conduction. System 10 can be configured to minimize heat production in the outermost 80% of a mucosal layer, such as to ablate the outermost 80% of the mucosal layer via thermal conduction. System 10 can be configured to maximize the flow of electrical current, such as through the innermost 50% of a mucosal layer, or through the innermost 20% of a mucosal layer. In some embodiments, system 10 can be configured to avoid detachment of tissue particles.

EDU 330, treatment element 145 and/or other components of system 10 can be configured to treat target tissue TT such that the temperature of at least a portion of the target tissue TT rises rapidly, such as at a rate of greater than or equal to 17.5° C. per second. Treatment can be delivered to cause the temperature of at least a portion of the target tissue TT to reach a setpoint temperature between 60° C. and 90° C., such as a setpoint temperature between 65° C. and 85° C. System 10 can be configured to cause the target tissue TT to elevate to a setpoint temperature and maintain that setpoint temperature, such as by maintaining the setpoint temperature for a time period between 2 and 40 seconds. In these embodiments, the setpoint temperature can be between 60° C. and 90° C., such as a setpoint temperature between 65° C. and 85° C. that is maintained for between 5 and 15 seconds. In some embodiments, after a setpoint temperature is achieved and/or maintained, the treatment can be adjusted (e.g. by adjusting energy delivery from EDU 330) such that tissue temperature decreases over time, such as to match a tissue response of the target tissue TT.

Controller 310 can include a graphical user interface configured to allow one or more operators of system 10 to perform one or more functions such as entering of one or more system input parameters and visualizing and/or recording of one or more system output parameters. Controller 310 can include one or more user input components (e.g. touch screens, keyboards, joysticks, electronic mice and the like), and one or more user output components (e.g. video displays; liquid crystal displays; alphanumeric displays; audio devices such as speakers; lights such as light emitting diodes; tactile alerts such as assemblies including a vibrating mechanism; and the like). Examples of system input parameters include but are not limited to: temperature of ablative fluid to be delivered such as temperature of fluid to be delivered to a nozzle or to an expandable reservoir such as a balloon; type of ablative fluid to be delivered; rate of ablative fluid to be delivered; volume of ablative fluid to be delivered; type of energy to be delivered such as RF energy, thermal energy and/or mechanical energy; quantity of energy to be delivered such as a cumulative number of joules of energy to be delivered and/or peak amount of energy to be delivered; types and levels of combinations of energies to be delivered; energy delivery duration; pulse width modulation percentage of energy delivered; temperature of a cooling fluid to be delivered; temperature of a priming fluid to be delivered; flow rate of a fluid to be delivered; volume of a fluid to be delivered; number of reciprocating motions for an energy delivery element to transverse; temperature for a treatment assembly such as target temperature and/or maximum temperature; insufflation pressure; insufflation duration; and combinations of these. System input parameters can include information based on patient anatomy and/or conditions such as pre-procedural and/or peri-procedural parameters selected from the group consisting of: mucosal density and/or thickness; mucosal "lift" off of submucosa after a submucosal injection; longitudinal location of target tissue within the GI tract; and combinations of these. Examples of system output parameters include but are not limited to: temperature information such as tissue and/or treatment assembly temperature information; pressure information such as balloon pressure information and/or insufflation pressure information; force information such as level of force applied to tissue information; patient information such as patient physiologic information recorded by one or more sensors; and combinations of these.

Controller 310 and/or one or more other components of system 10 can include an electronics module, such as an electronics module including a processor, memory, software, and the like. Controller 310 is typically configured to allow an operator to initiate, modify and cease treatment of target tissue TT by the various components of system 10, such as by controlling EDU 330 and/or pumping assembly 336. Controller 310 can be configured to modify one or more tissue treatment parameters, such as a parameter selected from the group consisting of: temperature of an ablative fluid to be delivered directly to tissue or to an expandable reservoir such as a balloon; type of ablative fluid to be delivered; rate of ablative fluid to be delivered; volume of ablative fluid to be delivered; pulse width modulation on-time and/or off-time; a time division multiplexing parameter; and combinations of these. Controller 310 can be configured for manual control, so that the operator first initiates the tissue treatment, then allows the treatment element 145 and/or another associated treatment element to treat the target tissue TT for some time period, after which the operator terminates the treatment.

Controller 310 and EDU 330 can be configured to treat target tissue TT in constant, varied, continuous and discontinuous energy delivery or other treatment delivery profiles. Pulse width modulation and/or time division multiplexing (TDM) can be incorporated to achieve precision of an ablative treatment, such as to ensure ablation of target tissue TT while leaving non-target tissue intact.

In some embodiments, where system 10 is further configured to perform hot fluid ablation, controller 310 can be configured to adjust the temperature, flow rate and/or pressure of fluid delivered to an expandable reservoir, such as when treatment assembly 140 and/or expandable assembly 130 comprise a balloon. Controller 310 can be configured to initiate insufflation and/or to adjust insufflation pressure. Controller 310 can be configured to deliver energy or otherwise treat target tissue in a closed-loop fashion, such as by modifying one or more tissue treatment parameters based on signals from one or more sensors of system 10, such as those described hereabove. Controller 310 can be programmable such as to allow an operator to store predetermined system settings for future use.

Controller 310 can comprise an impedance monitoring assembly, such as an impedance monitoring assembly that receives impedance information from one or both of sensor 139 of expandable assembly 130 and/or sensor 149 of treatment assembly 140. EDU 330 can deliver RF energy to one or more electrode-based treatment elements of system 10 based on the impedance determined by the impedance monitoring assembly.

Numerous embodiments of the systems, methods and devices for treating target tissue TT described hereabove include controlling and/or monitoring the change in target tissue temperature to cause its ablation, such as a temperature increase above 43° C., typically above 60° C., 70° C. or 80° C., to ablate at least a portion of the target tissue TT. One or more cooling fluids can be delivered to limit or otherwise control ablation, such as to prevent damage to non-target tissue, such as the duodenal adventitia. Pumping assembly 336 can be configured to deliver a fluid to tissue and/or a component and/or assembly of system 10, such as to warm and/or cool the tissue, component and/or assembly. Pumping assembly 336 can be configured to deliver a cooling fluid to a luminal wall such as the duodenal wall, such as prior to a delivery of energy, during a delivery of energy and/or after a delivery of energy. In some embodiments, a chilled fluid is used to cool tissue prior to, during and/or after a high temperature ablation of tissue. System 10 can be configured to deliver a fluid at a temperature below 37° C. or below 20° C. The chilled fluid can be delivered at a temperature between 0° C. and 7° C., and in some embodiments, the chilled fluid is delivered at a temperature less than 0° C. System 10 to can be configured to deliver chilled fluid at multiple temperatures to target tissue TT and/or other tissue. System 10 can be configured to deliver a first chilled fluid at a first temperature for a first time period, followed by a second chilled fluid delivered at a second temperature for a second time period. The first and second chilled fluids can be similar or dissimilar fluids, such as similar or dissimilar liquids and/or gases. In some embodiments, the first chilled fluid is colder than the second chilled fluid, such as a first chilled fluid delivered at approximately 4° C. for a time period of approximately 5 seconds, followed by fluid delivered at a higher temperature (e.g. a temperature between 10° C. and 37° C.) for a time period of at least 5 seconds. The chilled fluid can be delivered between treatment of a first portion of target tissue and a second portion of target tissue (e.g. to the same or different tissue), such as to remove residual heat remaining after the first treatment. The cooling fluid can be delivered through functional element 138 of expandable assembly 130 and/or functional element 148 of treatment assembly 140, such as when functional elements 138 and/or 148 comprises a fluid delivery element such as a nozzle, an exit hole, a slit, or a permeable membrane. The cooling fluid can be supplied to a location within expandable assembly 130 and/or treatment assembly 140, such as when expandable assembly 130 and/or treatment assembly 140 comprises a balloon or other expandable reservoir configured to contact tissue. Alternatively or additionally, pumping assembly 336 can be fluidly attached to another component of treatment device 100 and/or system 10, the attached component not shown but configured to deliver fluid to tissue and/or a component of system 10 such as to add and/or absorb heat. Pumping assembly 336 can comprise a cryogenic source used to deliver fluids at low temperatures, such as temperatures below 0° C. Typical fluids delivered include but are not limited to: liquids such as water and/or saline; gases such as carbon dioxide, nitrogen, nitrous oxide and/or air; and combinations of these.

Pumping assembly 336 can include a desiccant and/or drying assembly configured to dehydrate or otherwise remove moisture from one or more delivered gases prior to their delivery. In some embodiments, fluid provided to one or more treatment elements 145 has its temperature modified by a component in a distal portion of device 100, such as a heating or cooling element integral or proximal to treatment element 145 (e.g. a peltier cooling element, an expanded gas cooling assembly, or a heating coil integral to treatment element 145). Alternatively or additionally, system 10 can include a component configured to directly contact tissue in order to cool or warm tissue. In some embodiments, radially expandable assembly 130, functional element 138 and/or functional element 148 can be configured to contact tissue and remove and/or add heat from the contacted tissue.

System 10 can include a motion control mechanism, such as motion transfer assembly 320. Motion transfer assembly 320 can be configured to rotate, translate and/or otherwise move a component of system 10, such as to move one or more of treatment assembly 140, treatment element 145 and/or expandable assembly 130. In some embodiments, motion transfer assembly 320 is configured to rotate and/or axially translate shafts 110a and/or 110b such that treatment assembly 140 and/or expandable assembly 130, respectively, are rotated and/or translated. Motion transfer assembly 320 can be configured to rotate treatment assembly 140 and/or expandable assembly 130 independently or in unison. Motion transfer assembly 320 can be configured to translate treatment assembly 140 as treatment is applied to a portion of target tissue TT. In some embodiments, contiguous tissue segments are treated by device 100 continuously as motion transfer assembly 320 causes treatment assembly 140 to translate at a rate of at least 10 cm per minute, or at a rate of least 20 cm per minute. In some embodiments, treatment assembly 140 is manually translated, such as at a rate of at least 10 cm per minute, or at least 20 cm per minute. Motion transfer assembly 320 can be configured to translate treatment assembly 140 between a first tissue treatment and a second tissue treatment. Motion transfer assembly 320 can include one or more rotational and/or linear drive assemblies, such as those including rotational motors, magnetic drives, lead screw and/or other linear actuators, and the like which are operably connected to shaft 110a and/or 110b. Shafts 110a and/or 110b are constructed with sufficient column strength and/or torque transfer properties to sufficiently rotate and/or translate treatment assembly 140 and/or expandable assembly 130, respectively. Motion transfer assembly 320 can be in communication with controller 310, such as to activate, adjust and/or otherwise control motion transfer assembly 320 and thus the motion of treatment assembly 140 and/or expandable assembly 130. Motion transfer assembly 320 can be manually driven and/or automatically (e.g. motor) driven. Alternatively or additionally, motion transfer assembly 320 can be used to advance and/or retract treatment assembly 140 and/or expandable assembly 130 from a first position to treat a first portion of target tissue, to a second position to treat a second portion of target tissue. In this embodiment, repositioning of treatment assembly 140 and/or expandable assembly 130 can be configured to provide overlapping treatment, such as the overlapping treatment described in reference to FIG. 4 hereabove.

In some embodiments, system 10, first treatment device 100 and/or second treatment device 100' are constructed and arranged to perform a fractional treatment of tissue, such as is described hereabove in reference to FIG. 1. First treatment device 100 and/or second treatment device 100' can be constructed and arranged to treat target tissue with a fractional delivery of RF energy, such as monopolar and/or bipolar RF energy delivered from an array of electrodes positioned on an expandable element. In some embodiments, first treatment device 100 and/or second treatment device 100' are configured as a laser or other light energy delivery device constructed and arranged to provide a fractional energy delivery to target tissue. In some embodiments, first treatment device 100 and/or second treatment device 100' are configured to vaporize at least a portion of target tissue.

As described hereabove, system 10 can include one or more additional treatment devices, such as second treatment device 100'. Second treatment device 100' and/or other treatment devices of the present inventive concepts can be configured to treat target tissue TT in the same clinical procedure, or in a clinical procedure performed at least twenty-four hours after the first clinical procedure. Second treatment device 100' can be of similar or dissimilar construction to treatment device 100. In some embodiments, second treatment device 100' comprises an expandable assembly with a different diameter than expandable assembly 130 of device 100. In some embodiments, second treatment device 100' comprises a treatment element with a different construction and arrangement than treatment element 145 of treatment device 100. In some embodiments, second treatment device 100' comprises a device selected from the group consisting of: hot fluid filled balloon device; RF energy delivery device; vapor ablation device; cryogenic ablation device; laser ablation device; ultrasound ablation device; mechanical abrasion device; and combinations of these. Second treatment device 100' can comprise at least one ablation element selected from the group consisting of: an RF energy delivery element such as one or more electrodes, each comprising one or more elongate conductors; an ultrasonic transducer such as one or more piezo crystals configured to ablate tissue; a laser energy delivery element such as one or more optical fibers and/or laser diodes; a heat delivery element such as a hot fluid filled balloon; a rotating ablation element; a circumferential array of ablation elements; and combinations of these.

System 10 can further include one or more imaging devices, such as imaging device 410. Imaging device 410 can be configured to be inserted into the patient and can comprise a visual light camera; an ultrasound imager; an optical coherence domain reflectometry (OCDR) imager; and/or an optical coherence tomography (OCT) imager, such as when integral to, attached to, contained within and/or proximate to shaft 110*a* and/or 110*b*. Imaging device 410 can be inserted through a separate working channel of endoscope 350, lumen not shown. In one embodiment, imaging device 410 is an ultrasound transducer connected to a shaft, not shown but surrounded by shaft 110*a* and typically rotated and/or translated to create a multi-dimensional image of the area surrounding imaging device 410. Alternatively or additionally, imaging device 410 can be external to the patient, such as an imaging device selected from the group consisting of: an X-ray; a fluoroscope; an ultrasound image; an MRI; a PET Scanner; a near-infrared imaging camera; a fluorescence imaging camera; and combinations of these. Image and other information provided by imaging device 410 can be provided to an operator of system 10 and/or used by a component of system 10, such as controller 310, to automatically or semi-automatically adjust one or more system parameters such as one or more energy delivery parameters.

System 10 can further include protective element 191, configured to be positioned proximate tissue to prevent damage to certain tissue during tissue ablative fluid delivery, other energy delivery and/or other tissue treatment event. Protective element 191 can comprise an element selected from the group consisting of: a deployable and/or recoverable cap and/or covering; an advanceable and/or retractable protective sheath; and combinations of these. Protective element 191 can be delivered with endoscope 350 and/or another elongate device such that protective element 191 can be placed over or otherwise positioned to protect non-target tissue, such as tissue selected from the group consisting of: ampulla of Vater; bile duct; pancreas; pylorus; muscularis externae; serosa; and combinations of these. In some embodiments, protective element 191 is placed prior to treatment of at least a portion of target tissue TT, and removed in the same clinical procedure. In other embodiments, protective element 191 is implanted in a first clinical procedure, and removed in a second clinical procedure, such as a second clinical procedure as described herein. System 10 can be configured to identify non-target tissue, such as via a camera used to identify the ampulla of Vater.

System 10 can be configured to prevent excessive distension of the duodenum such as distension that could cause tearing of the serosa. In some embodiments, system 10 is configured such that all tissue contacting components and/or fluids delivered by system 10 maintain forces applied on a GI wall below 1.0 psi, such as less than 0.5 psi, or less than 0.3 psi. System 10 can be configured to avoid or otherwise minimize damage to the muscularis layer of the GI tract, such as by controlling pressure of target tissue treatment (e.g. via controlling expansion force of treatment assembly 140 and or expandable assembly 130) and/or by otherwise minimizing trauma imparted on any tissue by one or more components of system 10.

System 10 can further include one or more pharmaceutical and/or other agents 420, such as an agent configured for systemic and/or local delivery to a patient. Agents 420 can be delivered pre-procedurally, peri-procedurally and/or post-procedurally. Agents 420 can comprise one or more imaging agents, such an imaging agent used with imaging device 410. Agents 420 can be one or more pharmaceutical or agents configured to improve healing, such as agents selected from the group consisting of: antibiotics; steroids; mucosal cytoprotective agents such as sucralfate, proton pump inhibitors and/or other acid blocking drugs; and combinations of these. Alternative or in addition to agents 420, pre-procedural and/or post-procedural diets can be employed, as described herein. For example, pre-procedural diets can include food intake that is low in carbohydrates and/or low in calories, and post-procedural diets can include food intake that comprise a total liquid diet and/or a diet that is low in calories and/or low in carbohydrates.

In some embodiments, system 10 does not include a chronically implanted component and/or device, only body inserted devices that are removed at the end of the clinical procedure or shortly thereafter, such as devices removed within 8 hours of insertion, within 24 hours of insertion and/or within one week of insertion. In an alternative embodiment, implant 192 can be included. Implant 192 can comprise at least one of: a stent; a sleeve; and/or a drug delivery device such as a coated stent, a coated sleeve and/or an implanted pump. Implant 192 can be inserted into the patient and remain implanted for a period of at least one month, at least 6 months or at least 1 year. In some embodiments, a first clinical procedure is performed treating target tissue, and a subsequent second clinical procedure is performed, as is described herein. In these two clinical procedure embodiments, a device can be implanted in the first clinical procedure, and removed in the second clinical procedure.

System 10 can include sizing device 430 which is constructed and arranged to be placed into one or more locations of the gastrointestinal tract or other internal location of the patient and measure the size or other geometric parameter of tissue. In some embodiments, sizing device 430 comprises a balloon, expandable cage or other sizing element constructed and arranged to measure the inner surface diameter of a tubular tissue such as duodenal and/or jejunal tissue. A diameter measurement can be performed by inflating a balloon of sizing device 430 to a predetermined pressure and performing a visualization procedure to determine balloon diameter. Alternatively or additionally, a balloon can be filled with a fluid and one or more of fluid volume or fluid pressure is measured to determine balloon diameter and subsequently diameter of tubular tissue proximate the balloon. In some embodiments, subsequent selection (e.g. size selection) and/or expansion diameter (e.g. sized for apposition) of treatment assembly 140 can be determined using these tissue geometry measurements. Alternatively or additionally, an expandable element such as a balloon or cage can comprise two or more electrodes configured to provide a tissue impedance measurement whose value can be correlated to a level of apposition of the expandable element, and whose expanded diameter (e.g. visually measured) subsequently correlated to a diameter of tubular tissue proximate the expandable element. In some embodiments, treatment assembly 140 and/or expandable assembly 130 comprises sizing device 430, such as when treatment assembly 140 and/or expandable assembly 130 comprise a balloon or other sizing element used to measure a diameter of the inner surface of tubular tissue.

System 10 can be constructed and arranged to control one or more system parameters, such as controlling one or more system parameters prior to, during or after the delivery of a thermal dose, during a priming procedure, during a sizing procedure and/or during a tissue expansion procedure. System 10 can be constructed and arranged to control a system parameter selected from the group consisting of: a priming procedure parameter such as priming temperature or priming duration; target tissue treatment parameter such as target tissue temperature or target tissue treatment duration; fluid flow rate such as treatment fluid flow rate; a pressure parameter such as a treatment element pressure maintained during treatment of target tissue; a treatment element diameter such as a treatment element diameter maintained during treatment of target tissue; and combinations thereof. System 10 can be constructed and arranged to control the size of an expandable reservoir, such as by controlling the diameter of treatment assembly 140 and/or another expandable reservoir as described herein. In some embodiments, a user of system 10 selects a size of an expandable reservoir, such as by selecting the size from a range of available sizes of treatment assembly 140 provided to the user in a kit.

Any of the components of system 10 can include a coating, such as a lubricious coating. In some embodiments, treatment elements 145 and/or radially expandable elements such as balloons include a lubricious or other material property modifying coating. In some embodiments, a radially expandable treatment assembly 140 and/or expandable assembly 130 comprise a hydrophilic coating, for example configured to disperse or otherwise move an ablative fluid.

Each of the components and/or devices of system 10 can be removably attached to another component, particularly treatment device 100, controller 310, EDU 330, motion transfer assembly 320, pumping assembly 336, ground pad 70, endoscope 350 and/or second treatment device 100'. Typical attachment means include but are not limited to mechanical or electromechanical connectors providing an electrical, optical and/or fluidic connection between the attached components.

While the preferred embodiments of the devices and methods have been described in reference to the environment in which they were developed, they are merely illustrative of the principles of the present inventive concepts. Modification or combinations of the above-described assemblies, other embodiments, configurations, and methods for carrying out the invention, and variations of aspects of the invention that are obvious to those of skill in the art are intended to be within the scope of the claims. In addition, where this application has listed the steps of a method or procedure in a specific order, it may be possible, or even expedient in certain circumstances, to change the order in which some steps are performed, and it is intended that the particular steps of the method or procedure claim set forth herebelow not be construed as being order-specific unless such order specificity is expressly stated in the claim.

What is claimed is:

1. A system for treating a patient comprising:
an elongate shaft comprising a distal portion, a proximal portion, and a single fluid exchange lumen therebetween having a single lumen attachment port, wherein the elongate shaft is constructed and arranged to be introduced into a duodenum of the patient;
an expandable reservoir positioned on the elongate shaft distal portion, wherein the expandable reservoir is constructed and arranged to receive a fixed amount of an ablative fluid from the single fluid exchange lumen and to deliver first and second thermal doses of energy to first and second portions of target tissue comprising duodenal mucosa, wherein the expandable reservoir has a tubular or round shape with a relatively uniform diameter configured to contact a wall of the patient's duodenum when expanded;
a fluid delivery assembly comprising a pumping assembly, a manifold, and a single manifold attachment port connecting the pumping assembly to the expandable reservoir via the single lumen attachment port and the single fluid exchange lumen; and an energy delivery unit (EDU) including an ablative fluid reservoir and an evacuation reservoir which are fluidly connected to the manifold and the pumping assembly, wherein the ablative fluid reservoir and the evacuation reservoir are separate from each other;

a timer assembly, wherein the timer assembly is configured to control the manifold to selectively (1) deliver the ablative fluid from the ablative fluid reservoir sequentially through the pumping assembly, the single manifold attachment port, the single lumen attachment port, and the single fluid exchange lumen to the expandable reservoir and (2) remove the ablative fluid from the expandable reservoir sequentially through the single fluid exchange lumen, the single lumen attachment port, the single manifold attachment port, and the pumping assembly to the evacuation reservoir;

wherein the ablative fluid reservoir is configured to provide at least first and second fixed amounts of the ablative fluid to the fluid delivery assembly and the evacuation reservoir is configured to receive the at least first and second fixed amounts of the ablative fluid from the fluid delivery assembly; and wherein the first and second fixed amounts of the ablative fluid may be delivered to and removed from the expandable reservoir to sequentially deliver the first and second thermal doses of energy to the first and second portions of target tissue comprising the duodenal mucosa.

2. The system according to claim 1, wherein the system is constructed and arranged to maintain the expandable reservoir in contact with the first and second portions of target tissue for less than a maximum time period while the first fixed amount of ablative fluid is maintained within the expandable reservoir.

3. The system according to claim 2, wherein the maximum time period comprises a time period less than or equal to 10 seconds.

4. The system according to claim 3, wherein the maximum time period comprises a time period less than or equal to 6 seconds.

5. The system according to claim 1, wherein the system is constructed and arranged to maintain the expandable reservoir in contact with the first and second portions of target tissue for a pre-determined time period while the first fixed amount of ablative fluid is maintained within the expandable reservoir.

6. The system according to claim 5, wherein the pre-determined time period comprises a period of at least 0.5 seconds and no more than 10 seconds.

7. The system according to claim 1, wherein the system is constructed and arranged to (1) stop delivery of the first fixed amount of ablative fluid to the expandable reservoir or (2) stop the delivery of the first and second thermal doses of energy from the expandable reservoir by removing the first fixed amount of ablative fluid from the expandable reservoir to the evacuation reservoir.

8. The system according to claim 7, wherein the energy delivery unit (EDU) further includes a neutralizing fluid reservoir, and the system is constructed and arranged to deliver a neutralizing fluid from the neutralizing fluid reservoir into the expandable reservoir to reduce effects of the first thermal dose of energy.

9. The system according to claim 8, wherein the system is constructed and arranged to remove a majority of the first fixed amount of ablative fluid prior to delivering the neutralizing fluid into the expandable reservoir.

10. The system according to claim 1, wherein the system is constructed and arranged to deliver a cooling fluid to the expandable reservoir.

11. The system according to claim 10, wherein the cooling fluid comprises a fixed amount of cooling fluid.

12. The system according to claim 10, wherein the system is configured to deliver the cooling fluid at a temperature less than 37° C.

13. The system according to claim 1, wherein the elongate shaft comprises a length of at least 100 cm.

14. The system according to claim 1, wherein the elongate shaft is constructed and arranged to be advanced through a body lumen over a guidewire.

15. The system according to claim 1, wherein the elongate shaft comprises an insulating element.

16. The system according to claim 1, wherein the single fluid exchange lumen comprises a valve.

17. The system according to claim 16, wherein the valve is constructed and arranged to close when a pressure of the ablative fluid in the single fluid exchange lumen is below a first threshold pressure.

18. The system according to claim 1, wherein the expandable reservoir comprises a wall thickness of less than or equal to 0.002".

19. The system according to claim 1, wherein the expandable reservoir comprises an expanded diameter of at least 22 mm.

20. The system according to claim 1, wherein the expandable reservoir comprises a cylindrical portion with the relatively uniform diameter.

21. The system according to claim 1, wherein the fluid delivery assembly is constructed and arranged to provide the ablative fluid to the expandable reservoir at a flow rate of at least 2000 ml/min.

22. The system according to claim 1, wherein the fluid delivery assembly comprises a syringe.

23. The system according to claim 1, wherein the timer assembly is further configured to control the pumping assembly.

* * * * *